(12) United States Patent
Jiang et al.

(10) Patent No.: US 8,933,195 B2
(45) Date of Patent: Jan. 13, 2015

(54) HISTONE DEACETYLASE INHIBITORS AND SYNTHETIC METHOD THEREOF AND USE THEREOF IN MANUFACTURE OF MEDICAMENTS

(75) Inventors: Sheng Jiang, Nanjing (CN); Shang Li, Nanjing (CN); Zhiyi Yao, Nanjing (CN); Yiwu Yao, Nanjing (CN); Feng Zhang, Nanjing (CN); Yang Chao, Nanjing (CN); Hai Ye, Nanjing (CN); Min Chen, Nanjing (CN)

(73) Assignees: Nanjing Yoko Biomedical R & D Ltd., Nanjing, Jiangsu (CN); Nanjing Xingang Medical Co., Ltd., Nanjing, Jiangsu (CN); Nanjing Yoko Pharmaceutical Co., Ltd., Nanjing, Jiangsu (CN)

( * ) Notice: Subject to any disclaimer, the term of this patent is extended or adjusted under 35 U.S.C. 154(b) by 0 days.

(21) Appl. No.: 13/980,308

(22) PCT Filed: Feb. 23, 2012

(86) PCT No.: PCT/CN2012/071515
§ 371 (c)(1),
(2), (4) Date: Jul. 17, 2013

(87) PCT Pub. No.: WO2013/071715
PCT Pub. Date: May 23, 2013

(65) Prior Publication Data
US 2014/0243501 A1    Aug. 28, 2014

(30) Foreign Application Priority Data

Nov. 17, 2011 (CN) .......................... 2011 1 0364545

(51) Int. Cl.
*C07K 5/097* (2006.01)
*C07F 7/10* (2006.01)
*C07F 7/18* (2006.01)
*A61K 38/06* (2006.01)

(52) U.S. Cl.
CPC .................. *C07K 5/0821* (2013.01); *C07F 7/10* (2013.01); *C07F 7/1852* (2013.01); *C07F 7/1856* (2013.01); *A61K 38/06* (2013.01)
USPC .......................................................... 530/321

(58) Field of Classification Search
CPC ...................................................... C07K 5/0821
See application file for complete search history.

(56) References Cited

FOREIGN PATENT DOCUMENTS

WO    WO 2011/150283 A1 * 12/2011

OTHER PUBLICATIONS

Guan et al. "Clinical development of histone deacetylase inhibitor romidepsin" Drug Discoveries & Therapeutics. 2010; 4(6):388-391.*

* cited by examiner

*Primary Examiner* — Christina Bradley
(74) *Attorney, Agent, or Firm* — CBM Patent Consulting, LLC

(57) ABSTRACT

The invention provides histone deacetylase (HDAC) inhibitors shown as Formula I, where $R_1$ to $R_8$ are as defined in the specification. The invention also provides methods for synthesis of these compounds and applications of these compounds in preparing pharmaceuticals for preventing or treating mammal diseases related to the dysregulation of HDAC.

2 Claims, No Drawings

HISTONE DEACETYLASE INHIBITORS AND SYNTHETIC METHOD THEREOF AND USE THEREOF IN MANUFACTURE OF MEDICAMENTS

TECHNICAL FIELD OF THE INVENTION

The invention belongs to the field of pharmaceutical chemistry, and in particular relates to histone deacetylase inhibitors, and synthesis methods and pharmaceutical applications of these compounds.

BACKGROUND OF THE INVENTION

HDACs are a group of enzymes for regulating a series of biological effects including chromatin recombination, transcription activation or inhibition, cell cycle, cell differentiation, cell apoptosis and so on by inducing histone deacetylation at the level of cell chromatin, and are in particular related to gene transcription expression regulation after cell activation. HDAC inhibitors (HDACIs) are compounds for inhibiting the activity of the HDACs.

Histone acetylation plays a very important role in DNA transcription, replication and repair processes of the chromosomes. The HDAC inhibitors have been used as mood stabilizers and antiepileptic drugs in the past. In recent years, people begin to pay attention to the targeted therapy of the HDAC inhibitors on neurodegenerative diseases. Histone acetylation and deacetylation of chromatin are one of the key links for regulating the gene expression, and abnormal gene expression is the molecular biology basis of tumors and some genetic and metabolic diseases. The histone acetylation degree is coordinated and controlled by histone acetylase (HAT) and HDAC. Experiments prove that the HDAC inhibitors will improve the level of the chromatin histone acetylation, resulting in specific expression of gene activation, correspondingly causing terminal differentiation of cells or apoptosis of cancer cells. Therefore, HDAC has become one of the hottest targets at present in the field of research and development of tumor chemotherapeutics.

At present, it has been known that HDACs have 18 different subtypes and include four categories according to the germ line: I (HDAC1, 2, 3, 8), II (HDAC4, 5, 6, 7, 9, 10), III (SIRT1-SIRT7) and IV (HDAC11), wherein I, II and IV are classical families and are $Zn^{2+}$-dependent HDACs. Most of HDAC inhibitors in the current clinical research can inhibit several subtypes of HDACs, and these subtypes often belong to the $Zn^{2+}$-dependent HDAC family.

The HDAC inhibitors can inhibit the activity of HDACs in cells, so that the degree of the histone acetylation in the cells increases and the expression of genes (such as p21 and p53) improves, so the tumor cells are inhibited to proliferate and induced for differentiation and apoptosis. The HDAC inhibitors usually comprise three parts of a zinc ion binding region, a linkage region and a surface recognition region. The direct action of the inhibitor with zinc ions is indispensable to the inhibition of the activity. The HDAC inhibitors mainly include the following four categories: (1) short-chain fatty acids, such as butyric acid, phenylbutyric acid and salt compounds thereof; (2) compounds of hydroximic acids, such as suberoylanilide hydroxamic acid (SAHA) and trichostatin A (TSA), which are the most widely studied; (3) compounds of cyclic tetrapeptides, compounds of cyclopeptides are inhibitors with the most complex structure, the amino acid large cyclo in the molecule of inhibitors of cyclopeptides is used as the hydrophobic surface recognition region, the alkyl chain is used as the linkage region, the alkyl chain end is linked with a zinc ion binding group, such as trapoxin, HC-toxon, Apicidin, FK228 and Largazole; (4) compounds of benzamides, the activity of such compounds of benzamides is lower than that of compounds of hydroximic acids and compounds of cyclopeptides, but the compounds of benzamides have higher selectivity on the HDAC of the I category, such as MS-275, Cl-994 etc. In 2006, American Food and Drug Administration (FDA) approved the suberoylanilide hydroxamic acid (SAHA) of Merck Co., Ltd. to come into the market as vorinostat (Zolinza), the suberoylanilide hydroxamic acid is used for treating CTCL and is the first HDAC inhibitor antitumor drug available in the market.

FK228 (romidepsin) is bicyclic tetrapeptide separated from the broth medium of chrombacterium violaceum. FK228 has a specific bicyclic structure, and a bicyclolactone structure is formed of four amino acid residues (L-Val, L-2-amino-2-butylenoic acid, D-Cys and D-Val) and (3S, 4R-3-hydroxy-7-mercapto-4-heptenoic acid) through a disulfide bond. FK228 has similar selectivity on HDAC1 and HDAC2. The results of the computer simulation show that the thiol group of FK228 may be bonded with $Zn^{2+}$ through one water molecule. American FDA approved the cyclopeptide FK228 to come into the market as a drug for injection istodax (romidepsinon) on Nov. 6, 2009, it is also used for treating CTCL and becomes the second HDAC inhibitor available in the market following Zolinza, and the researches thereof for treating chronic lymphocytic leukemia, acute myeloid leukemia and other solid tumor are in the clinical stage.

Since the diseases, in particular cancers, related to the dysregulation of HDAC are high in morbidity and poor in prognosis, and the existing pharmaceuticals are dubious in curative effects and has much toxic or side effects, novel high-efficiency and low-toxicity HDAC inhibitors are required, and therefore the invention is designed for this purpose.

Content of the Invention

The invention provides HDAC inhibitors of cyclopeptides, which are used for overcoming the defects that the existing pharmaceuticals are dubious in curative effects and has much toxic or side effects. The invention also provides preparation methods and pharmaceutical applications of the HDAC inhibitors of cyclopeptides.

First of all, the invention provides a cyclopeptide compound with a chemical structure shown as Formula I, and pharmaceutically acceptable salt, isomer, racemate, prodrug or solvate thereof.

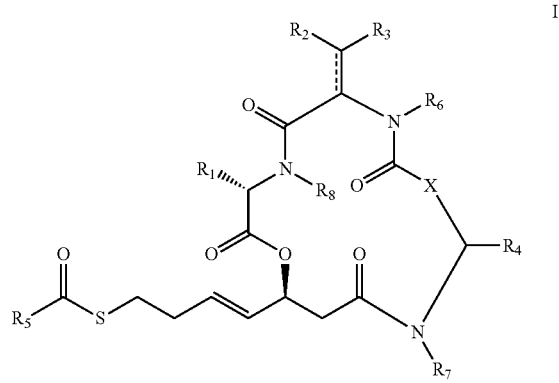

I

Where,
$R_1$ group is hydrogen, $C_{1-12}$ alkyl, $—CH_2—O—(C_{1-12}$ alkyl), $—CH_2—NH—(C_{1-12}$ alkyl), $—CH_2—S—(C_{1-12}$ alkyl), $C_{6-12}$ aryl, heteroaryl, —$CH_2$—($C_{6-12}$ aryl) or —$CH_2$-heteroaryl; the $C_{6-12}$ aryl, heteroaryl, —$CH_2$—$C_{6-12}$ aryl and —$CH_2$-heteroaryl may contain one or more substituents which may be halogen, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl or phenyl;

$R_2$ and $R_3$ groups are independently selected from hydrogen, $C_{1-12}$ alkyl, —O—($C_{1-12}$ alkyl), —NH—($C_{1-12}$ alkyl), —S—($C_{1-12}$ alkyl), $C_{6-12}$ aryl or heteroaryl;

$R_4$ group is hydrogen, $C_{1-12}$ alkyl, —O—($C_{1-12}$ alkyl), —NH—($C_{1-12}$ alkyl), —S—($C_{1-12}$ alkyl), $C_{6-12}$ aryl or heteroaryl;

$R_5$ group is hydrogen, $C_{1-12}$ alkyl, $C_{3-12}$ cycloalkyl, —O—($C_{1-12}$ alkyl), —NH—($C_{1-12}$ alkyl) or —S—($C_{1-12}$ alkyl);

$R_6$, $R_7$ and $R_8$ groups are independently selected from hydrogen, $C_{1-12}$ alkyl or t-butyloxycarboryl;

═══ represents a single bond or a double-bond;

X is

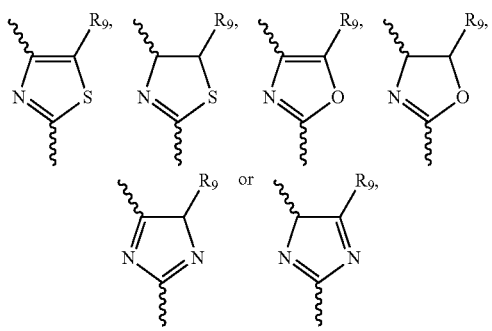

where $R_9$ group is hydrogen, $C_{1-12}$ alkyl, —O—($C_{1-12}$ alkyl), —NH—($C_{1-12}$ alkyl), —S—($C_{1-12}$ alkyl), $C_{6-12}$ aryl, heteroaryl, halogen, amino, hydroxy, nitro, cyano or carboxyl;

Or, X is a benzene ring which may contain one or more substituents, the substituent may be halogen, amino, hydroxy, nitro, cyano, $C_{1-12}$ alkyl, $C_{1-12}$ alkoxy, amino $C_{1-12}$ alkyl, acyl, acyloxy, thio $C_{1-12}$ alkyl, carboxyl, phenyl or heterocyclic substituent.

Further, in the above cyclic peptide compound,
$R_2$ is H,
═══ part is a double-bond,
$R_4$ is hydrogen or $C_{1-12}$ alkyl.

Further, in the above cyclic peptide compound,
$R_3$ is hydrogen or $C_{1-12}$ alkyl,
$R_5$ is hydrogen, $C_{1-12}$ alkyl or $C_{3-12}$ cycloalkyl,
$R_6$, $R_7$ and $R_8$ groups are independently selected from hydrogen.

Further, in the above cyclic peptide compound,
$R_3$ is methyl,
$R_6$, $R_7$ and $R_8$ groups are all hydrogen,
X is

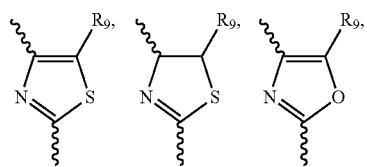

and

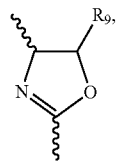

where $R_9$ group is hydrogen.

Further, the compound is selected from:

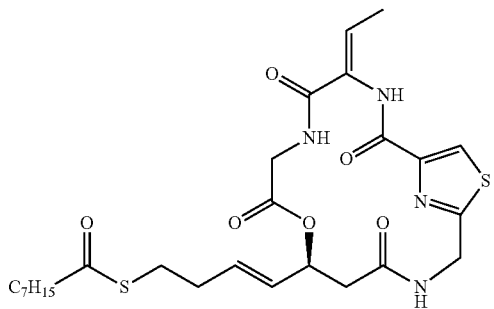

1-1

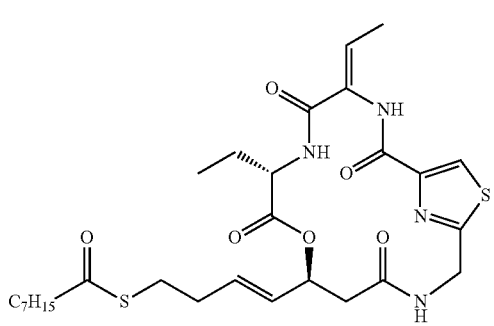

1-2

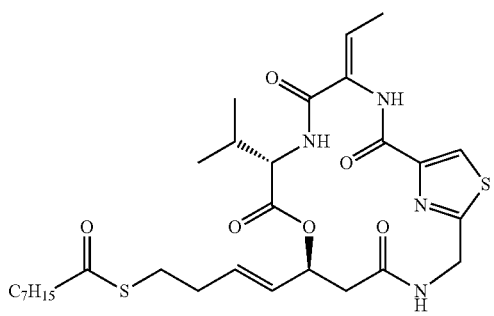

1-3

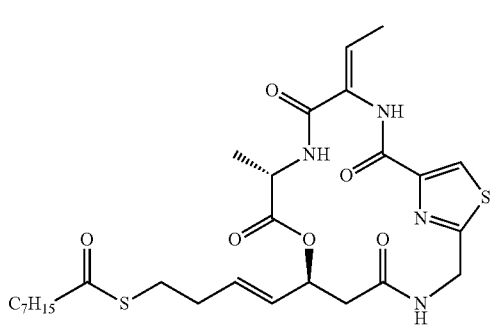

1-4

US 8,933,195 B2
5
-continued
1-5
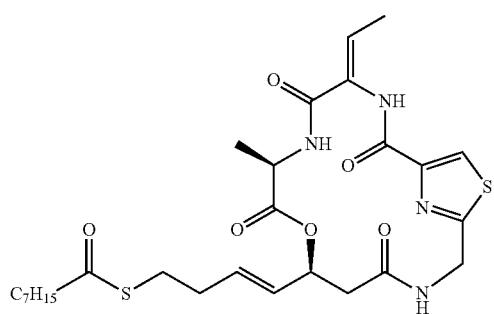
1-6
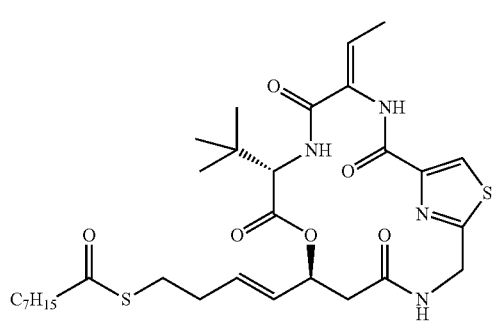
1-7
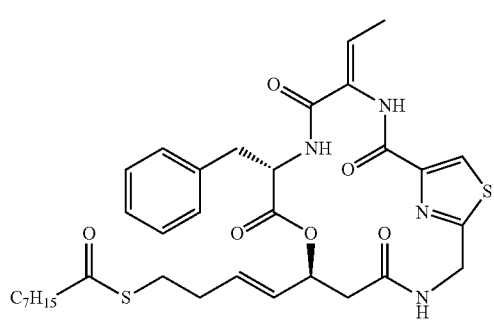
1-8
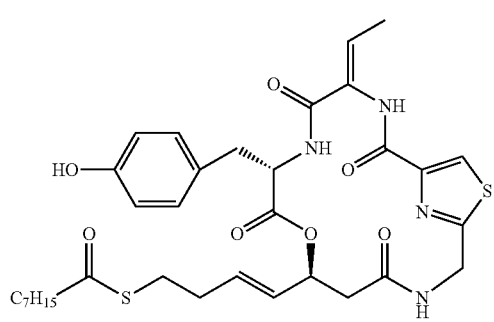
1-9
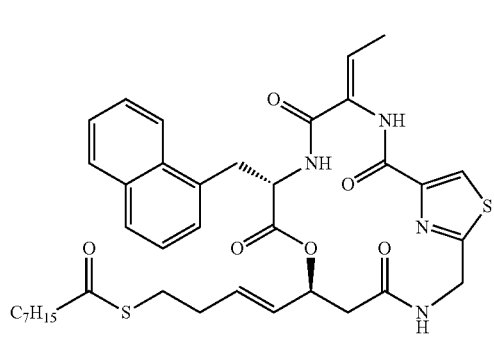
6
-continued
1-10
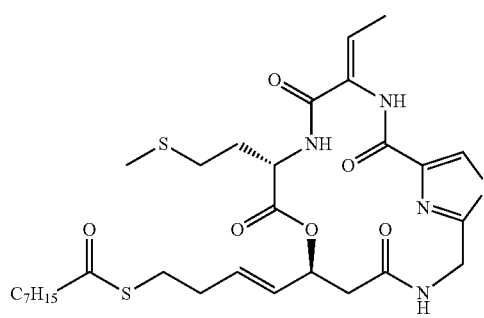
1-11
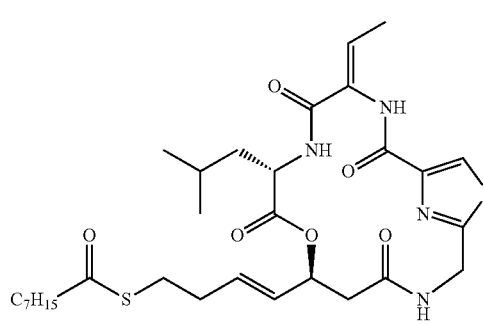
1-12
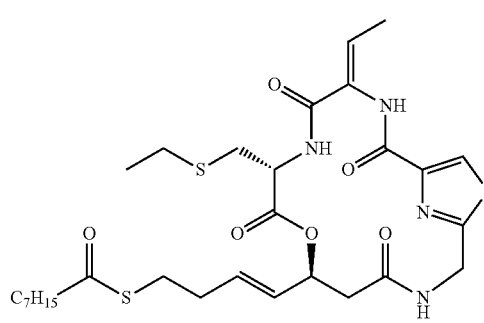
2-1
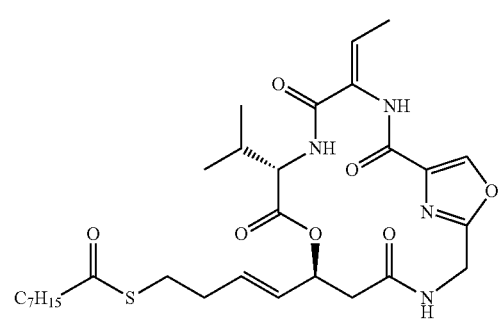
2-2
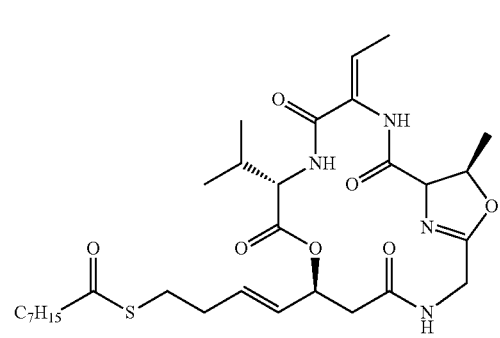

-continued
2-3
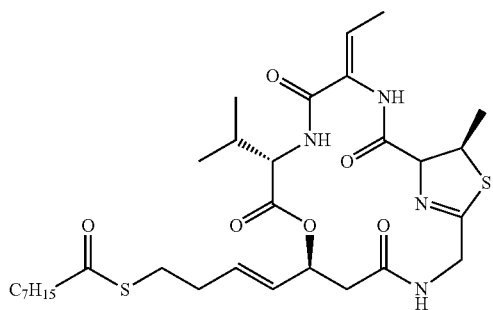
2-4
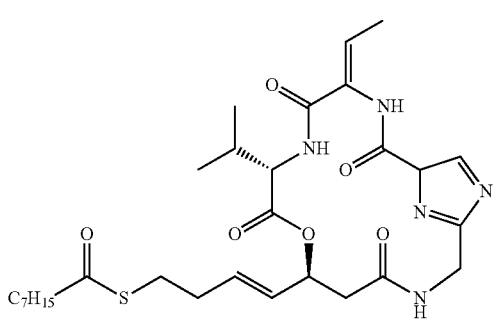
2-5
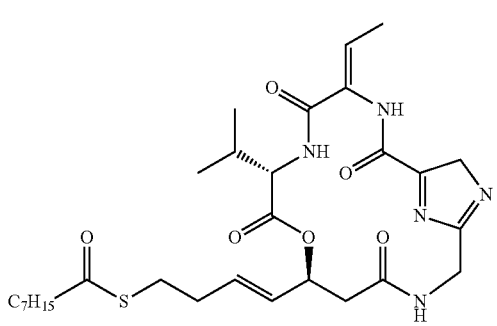
2-6
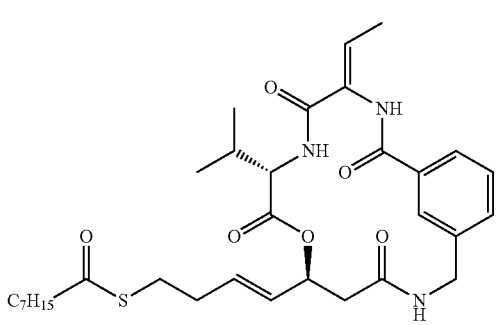
2-7
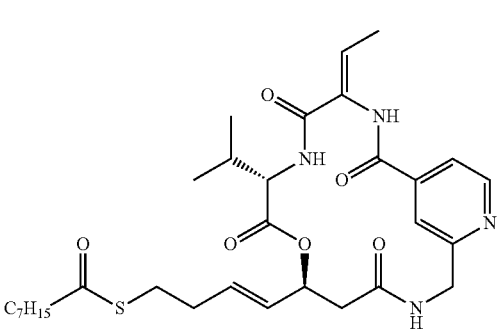
-continued
3-1
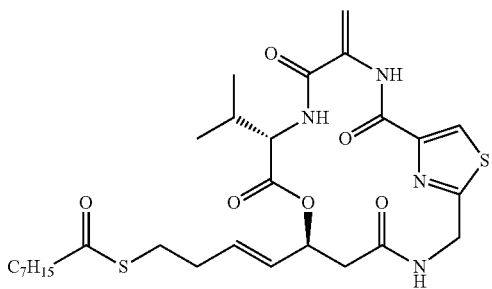
3-2
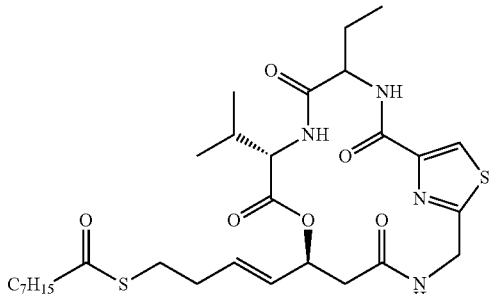
3-3
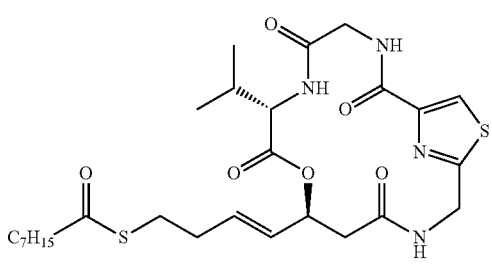
4-1
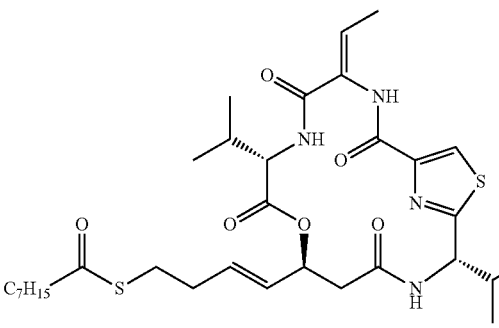
4-2
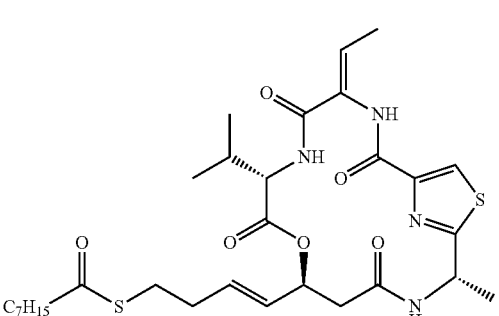

4-3
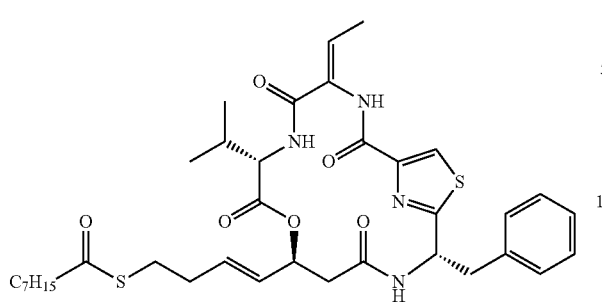
4-4
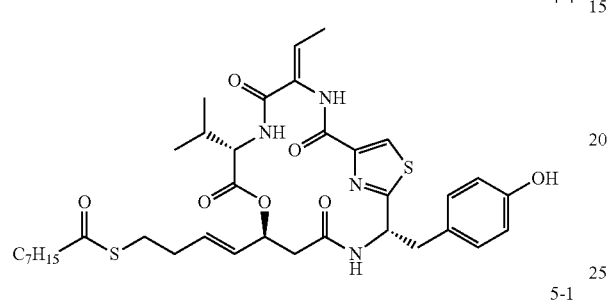
5-1
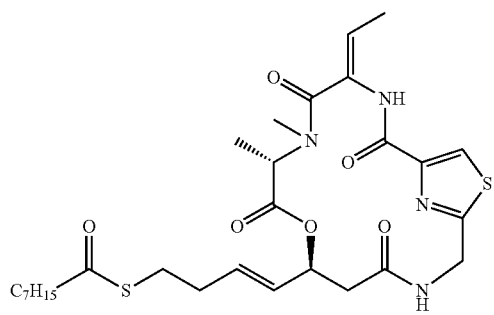
5-2
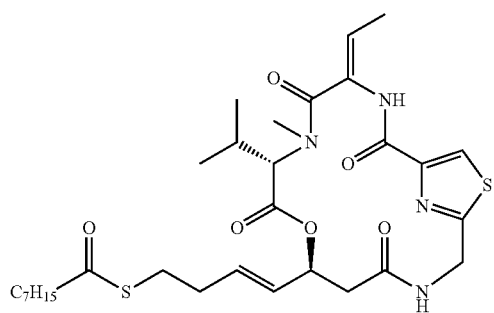
6-1
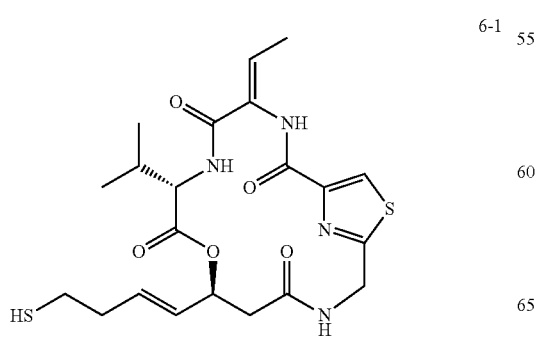
6-2
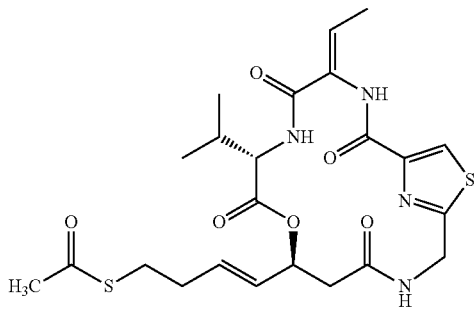
6-3
6-4
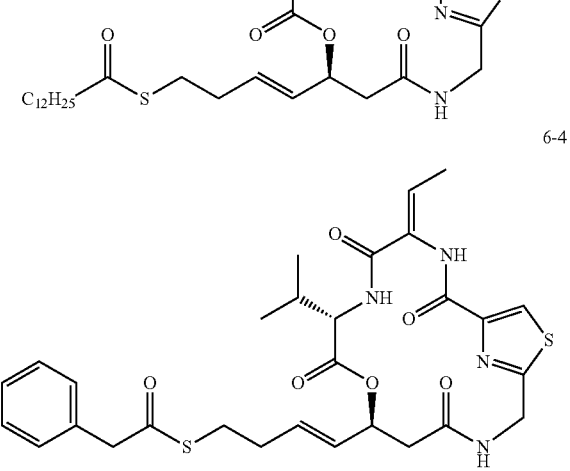
6-5
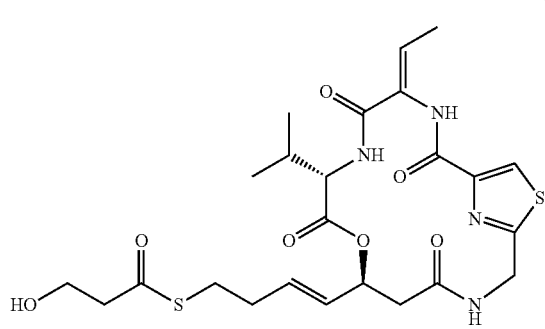
6-6
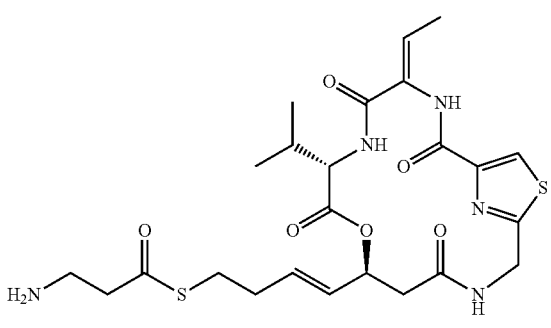

The invention further provides a method for preparing the cyclic peptide compound as shown in Formula I, comprising the steps as follows:

(1) The condensation of compounds of Formulae II and III with organic alkali under a condensation agent affords the compound of Formula IV. The reaction process is shown as follows:

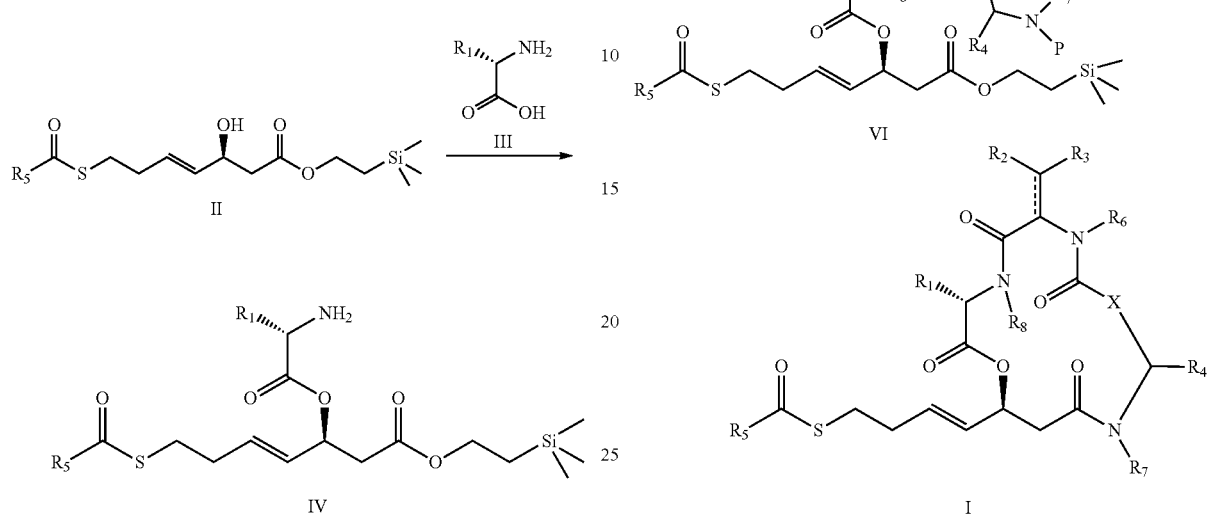

(2) The condensation of compounds of Formulae IV and V with organic alkali under a condensation agent affords the compound of Formula VI. The reaction process is shown as follows:

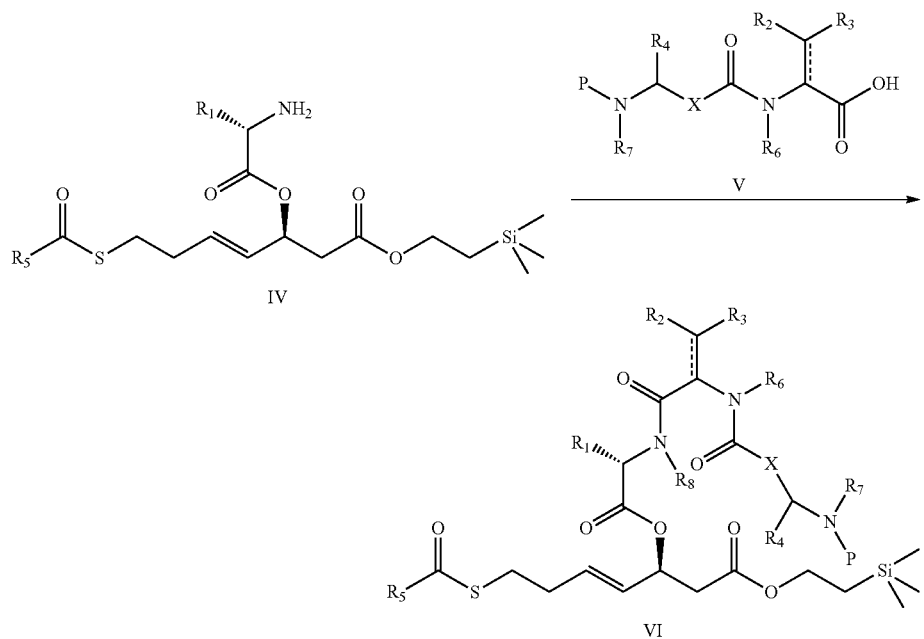

(3) The amino protecting group P in the compound of Formula VI is removed, and then the intramolecular cyclization of the compound under a condensation agent and organic alkali affords the compound of Formula I. The reaction process is shown as follows:

Where,
$R_1$, $R_2$, $R_3$, $R_4$, $R_5$, $R_6$, $R_7$ and $R_8$ are the same as those in claim 1;
P is an amino protecting group.

Further, the condensation agent may be DCC, EDC, HATU, HOAt, HOBt, DEAD, HBTU or PyBOP; the organic alkali is selected from imidazole, triethylamine, diisopropylethylamine, piperidine, lutidine, LiHMDS, NaHMDS, KHMDS, N-methylmorpholine, DABCO or pyridine; and the amino protecting group P is selected from Boc, Cbz, Bn, Fmoc, Alloc, Tos, Tfa, Trt or Bn.

The invention also provides a method for preparing a compound of Formula II, comprising the steps as follows:

(1) L-malic acid is methyl esterified and then reacts with sodium borohydride and acetum to obtain compound a, and then compound a reacts with tert-butyldimethylsilyl chloride and organic alkali (wherein, OCH₃ is substituted by trimethylsilyl ester protecting group) to obtain compound b. The reaction process is shown as follows:

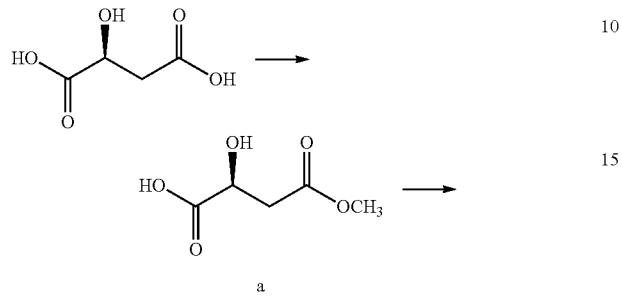

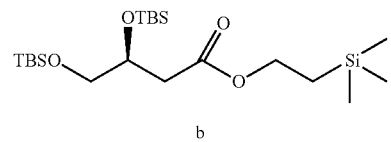

(2) Compound b reacts with camphorsulfonic acid to obtain compound c, compound c is then oxidized to obtain aldehyde and compound d, the aldehyde and compound d react with organic alkali to obtain compound e. The reaction process is shown as follows:

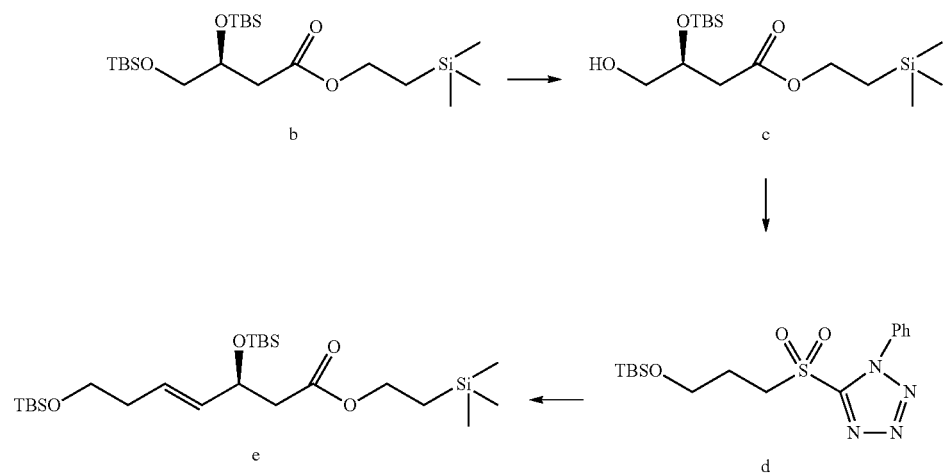

(3) Compound e reacts with camphorsulfonic acid to obtain compound f, then compound f, substituted thioacid and triphenylphosphine react with a condensation agent to obtain compound g, and compound g reacts with camphorsulfonic acid to obtain the compound of Formula II.

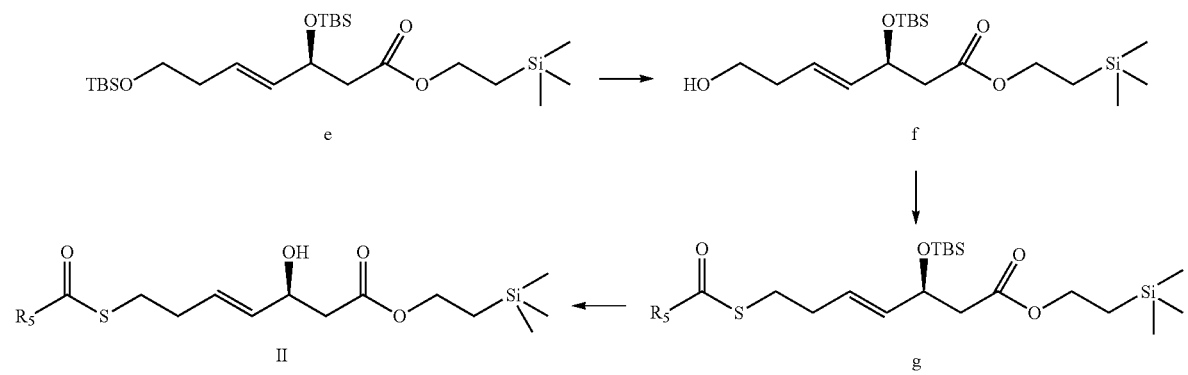

In the above synthesis process, the indispensable organic solvents may be selected from dichloromethane, tetrahydrofuran (THF), dimethylformamide (DMF), ethylene glycol dimethyl ether, 1,2-dichloroethane, dimethyl phthalate (DMP), methanol, ethanol, petroleum ether, n-hexane or diethyl ether; the indispensable inorganic alkali may be selected from sodium hydroxide, lithium hydroxide, potassium carbonate, sodium carbonate, sodium bicarbonate or calcium carbonate; and the indispensable acid may be selected from trifluoroacetic acid, hydrochloric acid, sulfuric acid or nitric acid. The oxidants may be Dess-Martin oxidants, Swern oxidants, m-chloroperbenzoic acid, pyridinium dichromate (PDC) or pyridinium chlorochromate (PCC).

The invention also provides applications of the above compounds in preparing pharmaceuticals for preventing or treating mammal diseases related to the dysregulation of HDAC.

Further, the mammal diseases related to the dysregulation of HDAC include cancers, neurodegenerative diseases, malaria and diabetes.

Further, the mammal diseases related to the dysregulation of HDAC include lymphoma, lung cancers, gastric cancers, pancreatic cancers, breast cancers, prostate cancers, leukemia, cervical cancers and colon cancers.

It should be noted that, the related terms, such as "alkyl", "aryl", "heteroaryl", "halogen" and "acyl", used in the text almost have the same general meanings as these terms in the field.

For example, the term "alkyl" refers to straight chain or branched chain. $C_{1-n}$ alkyl represents saturated aliphatic hydrocarbon of 1 to n carbon atoms, including straight chain or branched chain, for example, "$C_{1-12}$ alkyl" refers that the group is alkyl and there are 1 to 12 carbon atoms on the carbon chain of alkyl. It should be noted that, when there is no special restriction to the number of carbon atoms, the number of carbon atoms only refers to the number of carbon atoms on the specified alkyl part and does not include the number of carbon atoms on the substituent of alkyl.

Those of ordinary skill in the art should know meanings of the following terms or abbreviations.

The term "pharmaceutically acceptable salt" refers to salt that is applicable to be in contact with tissues of mammals, in particular human beings, without excessive toxicity, stimulation or anaphylaxis in a rational medical judgment range, and is proportional to a rational risk-benefit ratio, for instance, amine, carboxylic acid and pharmaceutically acceptable salt of other types of compounds are well-known in the field.

The term "isomer" refers to two or more compounds with same molecular composition and different structures and properties.

The term "racemate" refers to an equimolar mixture of chiral molecules with optical activity and enantiomers of the chiral molecules, the mixture is formed by equivalently mixing molecules with same optical activity capability and opposite optical activity direction, and the racemate is optically inactive as its optical activities counteract with each other due to molecular interactions.

The term "solvate" refers to a mixture of compounds and solvents, for example, crystal is a solvate.

The term "prodrug" refers to compounds for generating parent compounds with the above chemical formulae by hydrolyzing in blood and quickly transforming in vivo.

Substances corresponding to the English abbreviations used in Claims or Specification are respectively:

DCC (N,N'-dicyclohexylcarbodiimide, Cas No.: 538-75-0), EDCl [1-ethyl-(3-dimethylaminopropyl) carbodiimide hydrochloride, Cas No.: 25952-53-8], HATU (Cas No.: 148893-10-1), HOAt (Cas No.: 39968-33-7), HOBt (1-hydroxy-benzo-triazole, Cas No.: 2592-95-2), DEAD (diethyl azodicarboxylate, Cas No.: 1972-28-7), HBTU (Cas No.: 94790-37-1), PyBOP (benzotriazole-1-yl-oxytripyrrolidinophosphonium hexafluorophosphate, Cas No.: 132705-51-2), DIPEA (N,N-diisopropylethylamine, CAS No.: 7087-68-5); LiHMDS [lithium bis(trimethylsilyl)amide], NaHMDS (sodium Hexamethyldisilazide), KHMDS (potassium bis(trimethylsilyl)amide), DABCO (1,4-diazabicyclo[2.2.2]octane). The amino protecting group P is selected from Boc (t-butyloxycarboryl), Cbz (benzyloxycarbonyl), Bn (benzyl), Fmoc (fluorenylmethoxy carbony), Alloc (propoxycarbonyl), TOS (Tosyl), TFA (trifluoroacetic acid) or Trt (triphenylmethyl).

DETAILED DESCRIPTION OF THE INVENTION

In order to better explain the technical contents of the invention, the invention will be further illustrated below with specific embodiments.

It should be noted that, in the following embodiments, common after-treatment methods are as follows: at the end of the reaction, a proper amount of water is added to the reaction liquid, organic phases and water phases are separated, and the organic phases are combined; if necessary, the organic phases are dried with 5% HCl solution and/or saturated $NaSO_4$ in turn. After filtered, the organic phases are evaporated in vacuum to obtain a crude product. The crude product is separated and purified by column chromatography to obtain a final product.

Embodiment 1

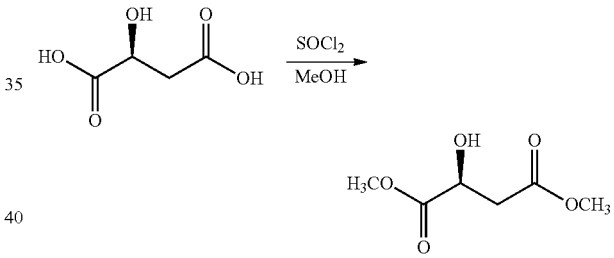

Thionylchloride (21.8 mL) is slowly and dropwise added to the solution of L-malic acid (10 g, 74.6 mmol) in methanol (50 mL) at 0, after the thionylchloride is completely added, the mixture is stirred overnight at room temperature, or refluxed for 4 h. The methanol is directly concentrated from the reaction liquid, washed with saturated NaHCO3 and saturated NaCl in turn, dried with anhydrous NaSO4, filtered, and evaporated in vacuum. The product is directly used in the next reaction to obtain 11.49 g of the crude product with the yield of 95%.

Embodiment 2

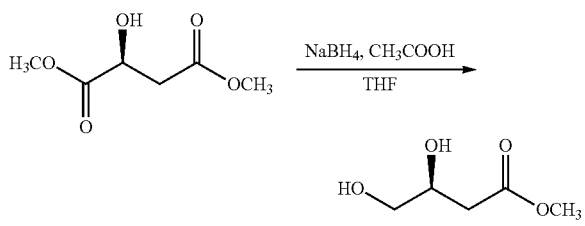

Aceticacid (2.01 mL, 35.1 mmol) is dissolved into 5 mL of tetrahydrofuran (THF) under argon at 0 in the absence of water and oxygen, the mixture is slowly and dropwise added to the solution of NaBH4 in THF (20 mL), one drop every two seconds on average. After the mixture is completely added, the mixture reacts with NaBH4 in the THF solution for 1 h. Dimethyl malate (5 g, 30.5 mmol) is dissolved into 10 mL of THF, and the mixture is added dropwise to a reaction flask and then stirred overnight at room temperature. Methanol is quenched, diatomite is filtered, and the filtrate is evaporated in vacuum and directly purified by column chromatography (petroleumether:ethyl acetate=1:1 to ethyl acetate only) to obtain 3.03 g of diol with the yield of 74%.

Embodiment 3

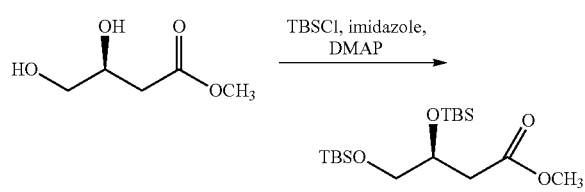

Raw material (5 g, 37.3 mmol), dimethylamino-pyridine (DMAP) (0.5 g, 0.41 mmol) and imidazole (8.6 g, 126.3 mmol) are dissolved into 100 mL of dichloromethane to prepare a solution. The solution of tert-butyldimethylsilyl chlide (TBDMSCl) (11.2 g, 74.6 mmol) in dichloromethane (10 mL) is slowly and dropwise added to the solution under ice bath. After the dichloromethane solution is completely added, the mixture is stirred overnight at room temperature. The reaction liquid is washed with water and saturated brine in turn. The organic layers are dried with anhydrous sodium sulfate, the solvent is distilled, and the residue is purified by silica-gel column chromatography to obtain 9.2 g of colorless oil with the yield of 89%.

Embodiment 4

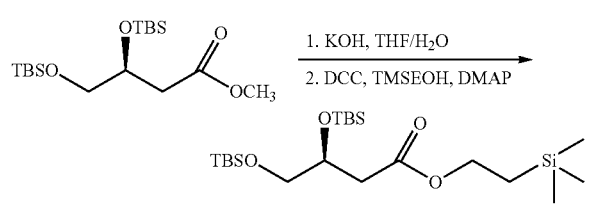

Raw material (5.43 g, 15.0 mmol) is dissolved into 75 mL of tetrahydrofuran. The solution of potassium hydroxide (KOH) (0.84 g, 15.0 mmol) in water (5 mL) is slowly and dropwise added into the tetrahydrofuran under ice bath. After the solution is completely added, the mixture is stirred for 1 h at room temperature. The Ph value of the reaction liquid is adjusted with diluted hydrochloric acid to 3, and then 100 mL of ethyl acetate is added to the reaction liquid. Organic phases are washed with water and saturated brine in turn. The organic layers are dried with anhydrous sodium sulfate, the solvent is evaporated, and the residue is purified by silica-gel column chromatography to obtain 4.96 g of colorless oil with the yield of 95%.

The compound (3.48 g, 10.0 mmol) obtained in the last step, DCC (0.5 g, 10 mmol) and TMSEOH (8.6 g, 10 mmol) are dissolved into 100 mL of dichloromethane with stirring at room temperature under argon to prepare a solution. The solution of TBDMSCl (11.2 g, 74.6 mmol) in dichloromethane (10 mL) is slowly and dropwise added into the solution under ice bath. After the solution of TBDMSCl in dichloromethane is completely added, the mixture is stirred overnight at room temperature. The reaction liquid is washed with water and saturated brine in turn. The organic layers are dried with anhydrous sodium sulfate, the solvent is evaporated, and the residue is purified by silica-gel column chromatography to obtain 9.2 g of colorless oil with the yield of 89%.

Embodiment 5

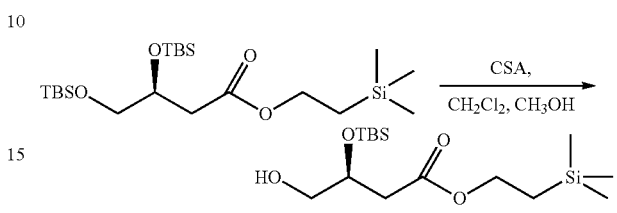

Raw material (9.2 g, 20.5 mmol) is dissolved into 50 mL of 50% methanol/dichloromethane solution and cooled to below −10. 0.96 g of camphorsulfonic acid is dissolved into 0.5 mL of methanol, and the mixture is added to a reaction flask, kept at −10° C., and stirred for 8 h. The mixture is quenched with 5 mL of saturated sodium bicarbonate, the organic solvent is distilled, and the residue is extracted with dichloromethane three times, washed with water and saturated brine in turn, dried with anhydrous sodium sulfate, concentrated, and purified by column chromatography (petroleum ether:ethyl acetate=10:1) to obtain 5.5 g of colorless oil with the yield of 82%.

Embodiment 6

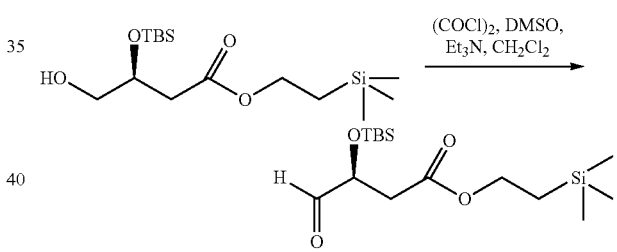

3 mL of dried DMSO is slowly and dropwsie added to 1.8 mL of solution of redistilled oxalyl chloride in dichloromethane under argon at −78° C. and stirred for 30 min. The dichloromethane solution, in which the raw material (3.5 g, 10.5 mmol) is dissolved, is slowly and dropwise added to a reaction flask. The mixture is stirred for 1 h, and then 12 mL of dried triethylamine is slowly and dropwise added into the mixture, warmed to room temperature, and kept in reaction for 1 h. The mixture is quenched with saturated ammonium chloride and washed with saturated brine. The organic layers are collected, dried with anhydrous sodium sulfate, and concentrated to obtain 3.32 g of flavescent oil with the yield of 95%.

Embodiment 7

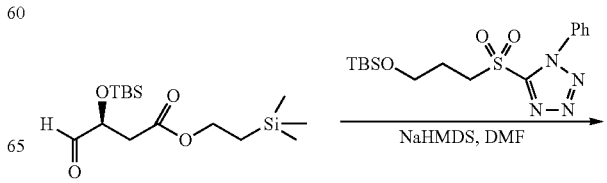

-continued

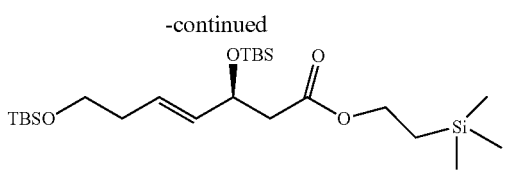

Raw material (3.5 g, 10.5 mmol) and tetrazole compound (4.02 g, 10.5 mmol) are dissolved into 50 mL of tetrahydrofuran under argon and cooled to −78° C. The solution (5.4 mL, 10.8 mmol) of 2M NaHMDS in THF is slowly and dropwise added to the mixture for reaction for 1 h, and the mixture is quenched with saturated ammonium chloride and extracted with ethyl acetate three times. The organic layers are dried with sewage sodium sulfate, concentrated and purified by column chromatography (5% ethyl acetate/petroleum ether) to obtain 3.68 g of colorless oil with the yield of 72%.

Embodiment 8

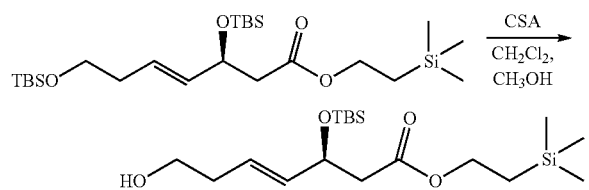

3.68 g of raw material is dissolved into 45 mL of dichloromethane solution and cooled to −10° C. 0.36 g of camphorsulfonic acid is dissolved into 5 mL of methanol, added to a reaction flask, and stirred for 8 h. The mixture is quenched with 5 mL of saturated sodium bicarbonate, and the organic solvent is distilled. Water is added into the residue and the water phase is extracted with dichloromethane three times. The organic layers are collected, dried with anhydrous sodium sulfate, concentrated, and purified by column chromatography (15% ethyl acetate/petroleum ether) to obtain 1.95 g of colorless oil with the yield of 70%.

Embodiment 9

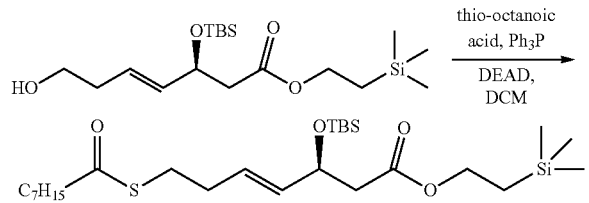

DEAD (3.74 mL, 8.23 mmol) is added dropwise to the solution of triphenylphosphine (2.16 g, 8.23 mmol) in dichloromethane under argon and ice bath and stirred for 15 min. Raw material (1.95 g, 5.20 mmol) and thio-n-octanoic acid (1.32 g, 8.23 mmol) are added to a reaction flask in turn, and stirred overnight at room temperature. The mixture is washed with saturated sodium bicarbonate solution and saturated brine in turn. The organic layers are collected, dried with anhydrous sodium sulfate, concentrated, and purified by column chromatography (10% ethyl acetate/petroleum ether) to obtain 2 g of colorless oil with the yield of 74%.

Embodiment 10

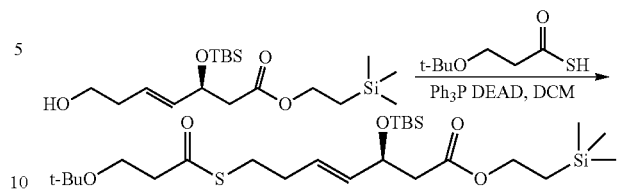

DEAD (3.74 mL, 8.23 mmol) is added dropwise to the solution of triphenylphosphine (2.16 g, 8.23 mmol) in dichloromethane under argon and ice bath and stirred for 15 min. Raw material (1.95 g, 5.20 mmol) and protective 3-thiohydracrylic acid (1.33 g, 8.23 mmol) are added to a reaction flask in turn, and stirred overnight at room temperature. The mixture is washed with saturated sodium bicarbonate solution and saturated brine in turn. The organic layers are collected, dried with anhydrous sodium sulfate, concentrated, and purified by column chromatography (10% ethyl acetate/petroleum ether) to obtain 3.46 g of colorless oil with the yield of 81%.

Embodiment 11

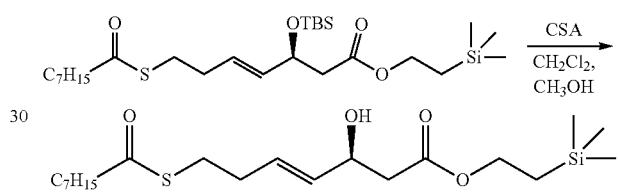

Raw material (2 g, 3.87 mmol) is dissolved into the solution of 50% methanol/dichloromethane (20 mL) and cooled to 0° C. 0.91 g of camphorsulfonic acid is dissolved into 1 mL of methanol, added to a reaction flask, and stirred overnight. The mixture is quenched with 5 mL of saturated sodium bicarbonate, and the organic solvent is distilled. Water is added into the mixture and the water phase is extracted with dichloromethane three times. The organic layers are collected, dried with anhydrous sodium sulfate, concentrated, and purified by column chromatography (20% ethyl acetate/petroleum ether) to obtain 1.12 g of colorless oil with the yield of 71%.

Embodiment 12

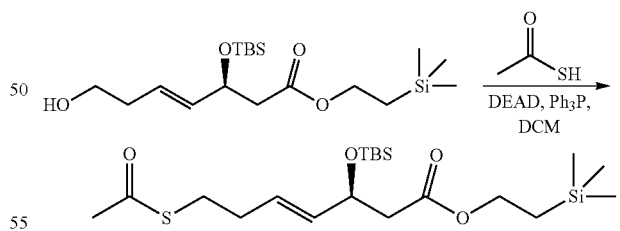

DEAD (1.12 mL, 2.74 mmol) is added dropwise to the solution of triphenylphosphine (0.65 g, 2.74 mmol) in dichloromethane under argon and ice bath, and stirred for 15 min. Raw material (0.585 g, 1.56 mmol) and thioacetic acid (0.4 g, 2.74 mmol) are added to a reaction flask in turn, and stirred overnight at room temperature. The mixture is washed with saturated sodium bicarbonate solution and saturated brine in turn. The organic layers are collected, dried with anhydrous sodium sulfate, concentrated, and purified by column chromatography (10% ethyl acetate/petroleum ether) to obtain 0.948 g of colorless oil with the yield of 80%.

Embodiment 13

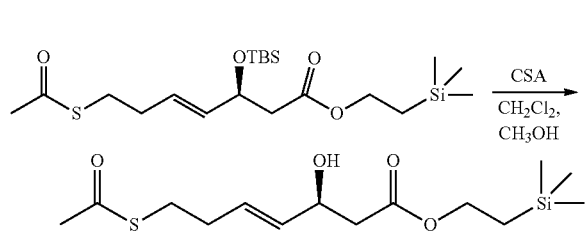

Raw material (0.839 g, 1.94 mmol) is dissolved into the solution of 50% methanol/dichloromethane (10 mL), and cooled to 0. 0.455 g of camphorsulfonic acid is dissolved into 1 mL of methanol, added to a reaction flask, and stirred overnight. The mixture is quenched with 5 mL of saturated sodium bicarbonate, and the organic solvent is distilled. Water is added into the mixture and the water phase is extracted with dichloromethane three times. The organic layers are collected, dried with anhydrous sodium sulfate, concentrated, and purified by column chromatography (20% ethyl acetate/petroleum ether) to obtain 0.481 g of colorless oil with the yield of 78%.

Embodiment 14

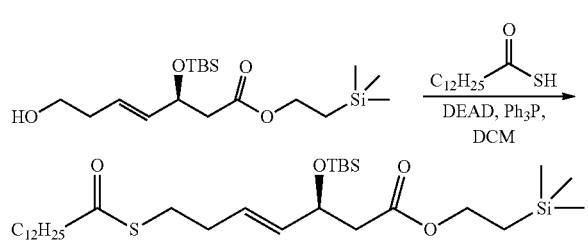

DEAD (1.35 mL, 3.29 mmol) is added dropwise to the solution of triphenylphosphine (0.78 g, 3.29 mmol) in dichloromethane under argon and ice bath, and stirred for 15 min. Raw material (1.102 g, 1.88 mmol) and thioacetic acid (0.758 g, 3.29 mmol) are added to a reaction flask in turn, and stirred overnight at room temperature. The mixture is washed with saturated sodium bicarbonate solution and saturated brine in turn. The organic layers are collected, dried with anhydrous sodium sulfate, concentrated, and purified by column chromatography (10% ethyl acetate/petroleum ether) to obtain 1.312 g of colorless oil with the yield of 68%.

Embodiment 15

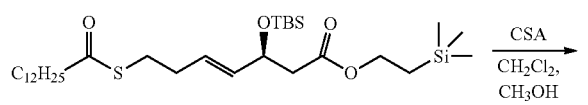

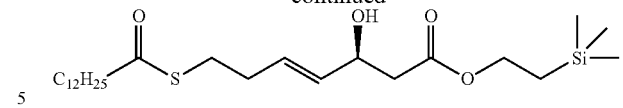

Raw material (1.172 g, 2 mmol) is dissolved into the solution of 50% methanol/dichloromethane (10 mL), and cooled to 0° C. 0.52 g of camphorsulfonic acid is dissolved into 1 mL of methanol, added to a reaction flask, and stirred overnight. The mixture is quenched with 5 mL of saturated sodium bicarbonate, and the organic solvent is distilled. Water is added into the mixture and the water phase is extracted with dichloromethane three times. The organic layers are collected, dried with anhydrous sodium sulfate, concentrated, and purified by column chromatography (20% ethyl acetate/petroleum ether) to obtain 0.766 g of colorless oil with the yield of 81%.

Embodiment 16

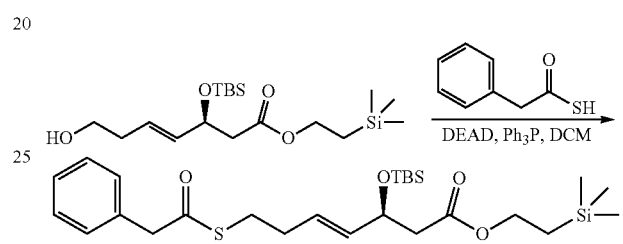

DEAD (0.81 mL, 1.97 mmol) is added dropwise to the solution of triphenylphosphine (0.81 mL, 1.97 mmol) in dichloromethane under argon and ice bath, and stirred for 15 min. Raw material (0.66 g, 1.13 mmol) and thiobisphenylacetic acid (0.3 g, 1.97 mmol) are added to a reaction flask in turn, and stirred overnight at room temperature. The mixture is washed with saturated sodium bicarbonate solution and saturated brine in turn. The organic layers are collected, dried with anhydrous sodium sulfate, concentrated, and purified by column chromatography (10% ethyl acetate/petroleum ether) to obtain 0.611 g of colorless oil with the yield of 61%.

Embodiment 17

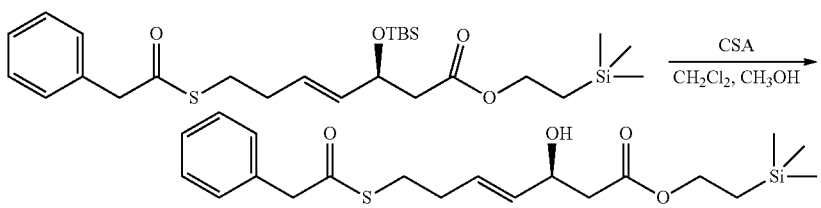

Raw material (0.61 g, 1.2 mmol) is dissolved into the solution of 50% methanol/dichloromethane (7 mL), and cooled to 0° C. 0.3 g of camphorsulfonic acid is dissolved into 1 mL of methanol, added to a reaction flask, and stirred overnight. The mixture is quenched with 5 mL of saturated sodium bicarbonate, and the organic solvent is distilled. Water is added into the mixture and the water phase is extracted with dichloromethane three times. The organic layers are collected, dried with anhydrous sodium sulfate, concentrated, and purified by column chromatography (20% ethyl acetate/petroleum ether) to obtain 0.412 g of colorless oil with the yield of 87%.

Embodiment 18

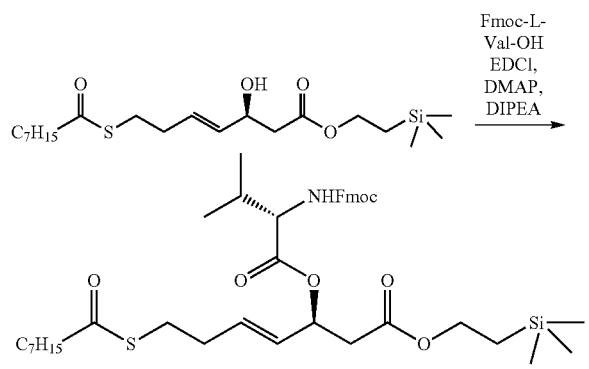

Fmoc-L-Val-OH (2.376 g, 7 mmol), EDCl (1.342 g, 7 mmol), DMAP (0.057 g, 0.468 mmol) and DIPEA (1.2 mL, 7 mmol) are in turn added to the solution of raw material (0.942 g, 2.34 mmol) in dichloromethane under argon at 0, and stirred overnight at room temperature. The saturated NaHCO3 solution is extracted with ethyl acetate three times, and organic phases are combined, washed with saturated NaCl, dried with anhydrous Na2SO4, filtered, evaporated in vacuum, and purified by column chromatography (ethyl acetate:petroleum ether=20:1 to 10:1) to obtain 1.45 g of clear liquid with the yield of 86%.

Embodiment 19

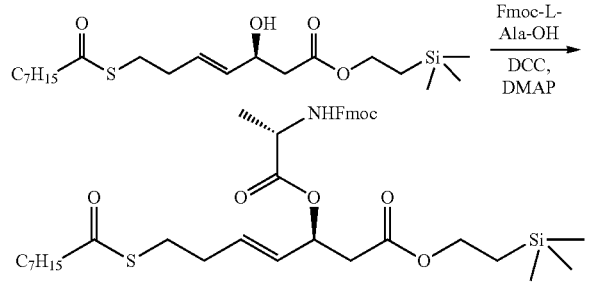

Fmoc-L-Val-OH (0.363 g, 1.17 mmol), DCC (0.241 g, 1.17 mmol) and DMAP (0.014 g, 0.12 mmol) are in turn added to the solution of raw material (0.235 g, 0.58 mmol) in dichloromethane under argon at 0, and stirred overnight at room temperature. The mixture is filtered, evaporated in vacuum, and purified by column chromatography (petroleum ether: ethyl acetate=20:1 to 10:1) to obtain 0.328 g of clear liquid with the yield of 81%.

Embodiment 20

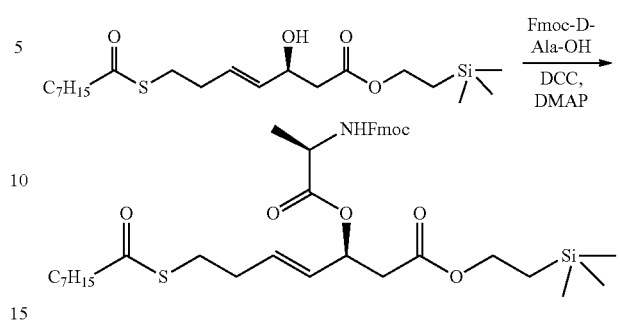

Fmoc-D-Ala-OH (0.392 g, 1.26 mmol), DCC (0.260 g, 1.26 mmol) and DMAP (0.016 g, 0.13 mmol) are in turn added to the solution of raw material (0.255 g, 0.63 mmol) in dichloromethane under argon at 0, and stirred overnight at room temperature. The mixture is filtered, evaporated in vacuum, and purified by column chromatography (petroleum ether:ethyl acetate=20:1 to 10:1) to obtain 0.378 g of clear liquid with the yield of 86%.

Embodiment 21

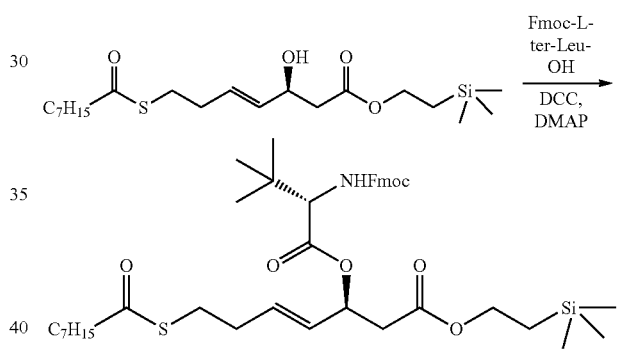

Fmoc-L-ter-Leu-OH (0.265 g, 0.75 mmol), DCC (0.155 g, 0.75 mmol) and DMAP (0.013 g, 0.1 mmol) are in turn added to the solution of raw material (0.198 g, 0.5 mmol) in dichloromethane under argon at 0, and stirred overnight at room temperature. The mixture is filtered, evaporated in vacuum, and purified by column chromatography (petroleum ether: ethyl acetate=20:1 to 10:1) to obtain 0.209 g of clear liquid with the yield of 57%.

Embodiment 22

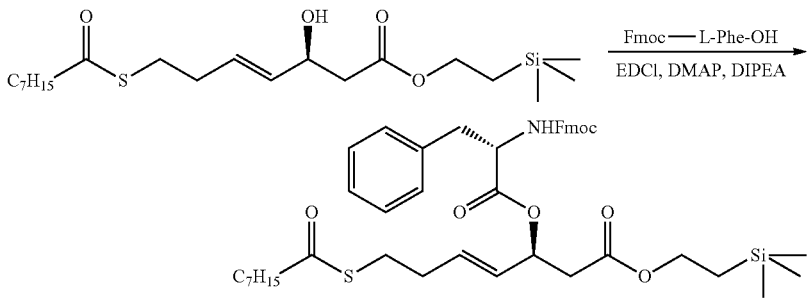

Fmoc-L-Phe-OH (0.728, 1.88 mmol), EDCl (0.36 g, 1.88 mmol), DMAP (0.015 g, 0.126 mmol) and DIPEA (0.3 mL, 1.88 mmol) are in turn added to the solution of raw material (0.25 g, 0.63 mmol) in dichloromethane under argon at 0, and stirred overnight at room temperature. The saturated NaHCO3 solution is extracted with ethyl acetate three times, and the organic phases are combined, washed with saturated NaCl, dried with anhydrous Na2SO4, filtered, evaporated in vacuum, and purified by column chromatography (petroleum ether:ethyl acetate=20:1 to 10:1) to obtain 0.35 g of clear liquid with the yield of 72%.

Embodiment 23

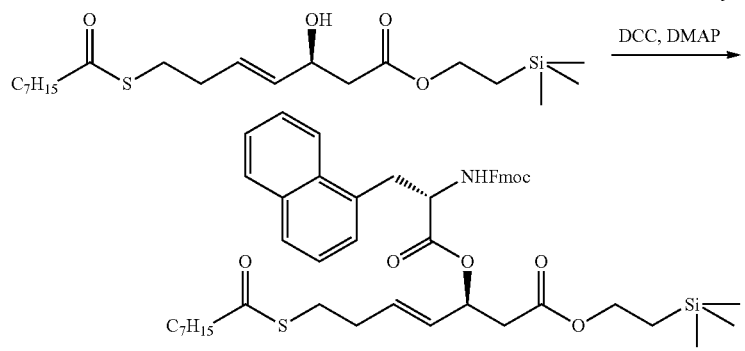

Fmoc-3-(1-naphthyl)-L-alanine (0.596 g, 1.3 mmol), DCC (0.268 g, 1.3 mmol) and DMAP (0.016 g, 0.13 mmol) are in turn added to the solution of raw material (0.26 g, 0.646 mmol) in dichloromethane under argon at 0° C. and stirred overnight at room temperature. The mixture is filtered, evaporated in vacuum, and purified by column chromatography (petroleum ether:ethyl acetate=20:1 to 10:1) to obtain 0.397 g of clear liquid with the yield of 75%.

Embodiment 24

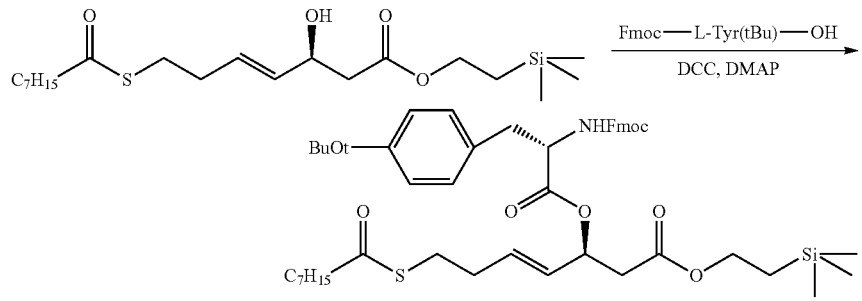

Fmoc-L-Tyr(tBu)-OH (0.516 g, 1.12 mmol), DCC (0.231 g, 1.12 mmol) and DMAP (0.014 g, 0.112 mmol) are in turn added to the solution of raw material (0.226 g, 0.56 mmol) in dichloromethane under argon at 0° C. and stirred overnight at room temperature. The mixture is filtered, evaporated in vacuum, and purified by column chromatography (petroleum ether:ethyl acetate=20:1 to 10:1) to obtain 0.355 g of clear liquid with the yield of 75%.

Embodiment 25

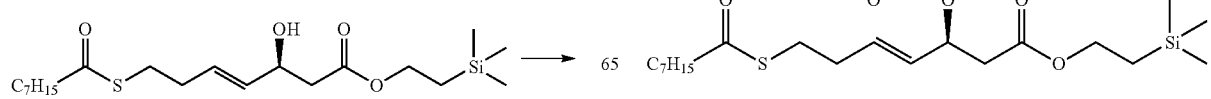

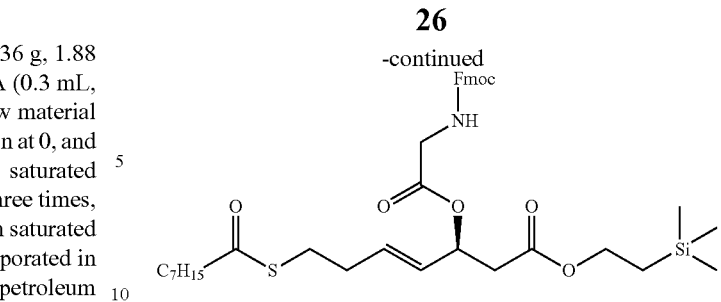

100 mg of raw material (0.25 mmol, 1 eq) and 148.6 mg of Fmoc-Gly-OH (0.5 mmol, 2 eq) are dissolved into 2 mL of anhydrous dichloromethane, 5.6 mg of DMAP (0.05 mmol, 0.2 eq) is added into the mixture, and 103 mg of DCC (0.5 mmol, 2 eq) is added into the mixture at 0° C. The mixture reacts for 1 h at 0° C., and is filtered to remove the solid, evaporated in vacuum to remove the solvent, and purified by column chromatography (ethyl acetate:petroleum ether=1:10) to obtain 170 mg of colorless liquid with the yield of 100%.

Embodiment 26

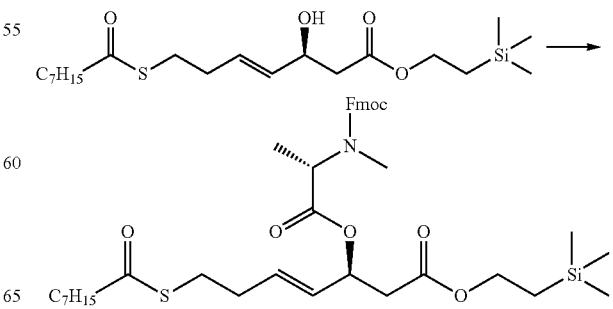

100 mg of raw material (0.25 mmol, 1 eq) and 162 mg of Fmoc-N-Me-Gly-OH (0.5 mmol, 2 eq) are dissolved into 2 mL of anhydrous dichloromethane, 5.6 mg of DMAP (0.05 mmol, 0.2 eq) is added into the mixture, and 103 mg of DCC (0.5 mmol, 2 eq) is added into the mixture at 0° C. The mixture reacts for 1 h at 0° C., and is filtered to remove the solid, evaporated in vacuum to remove the solvent, and purified by column chromatography (ethyl acetate:petroleum ether=1:10) to obtain 170 mg of colorless liquid with the yield of 100%.

Embodiment 27

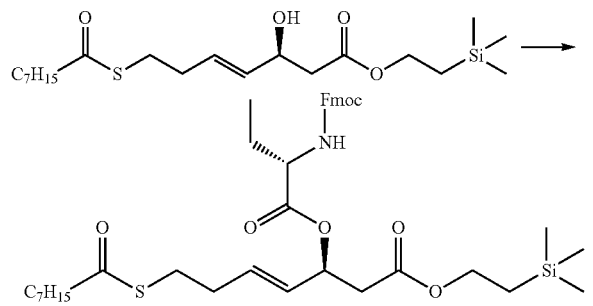

100 mg of raw material (0.25 mmol, 1 eq) and 167 mg of Fmoc-Abu-OH (0.5 mmol, 2 eq) are dissolved into 2 mL of anhydrous dichloromethane, 5.6 mg of DMAP (0.05 mmol, 0.2 eq) is added into the mixture, and 103 mg of DCC (0.5 mmol, 2 eq) is added into the mixture at 0° C. The mixture reacts for 1 h at 0° C., and is filtered to remove the solid, evaporated in vacuum to remove the solvent, and purified by column chromatography (ethyl acetate:petroleum ether=1:10) to obtain 163 mg of colorless liquid with the yield of 90%.

Embodiment 28

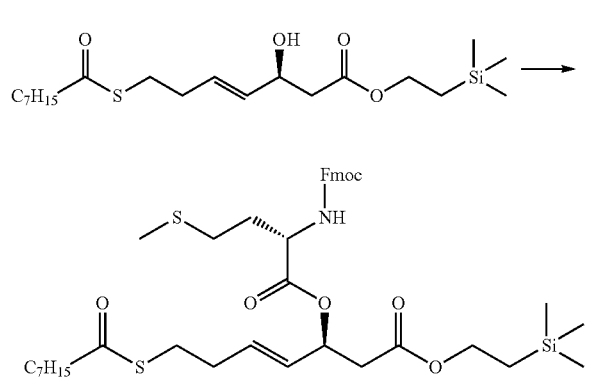

100 mg of raw material (0.375 mmol, 1 eq) and 278 mg of Fmoc-Gly-OH (0.75 mmol, 2 eq) are dissolved into 4 mL of anhydrous dichloromethane, 8.4 mg of DMAP (0.075 mmol, 0.2 eq) is added into the mixture, and 155 mg of DCC (0.75 mmol, 2 eq) is added into the mixture at 0° C. The mixture reacts for 1 h at 0° C., and is filtered to remove the solid, evaporated in vacuum to remove the solvent, and purified by column chromatography (ethyl acetate:petroleum ether=1:10) to obtain 270 mg of colorless liquid with the yield of 95.2%.

Embodiment 29

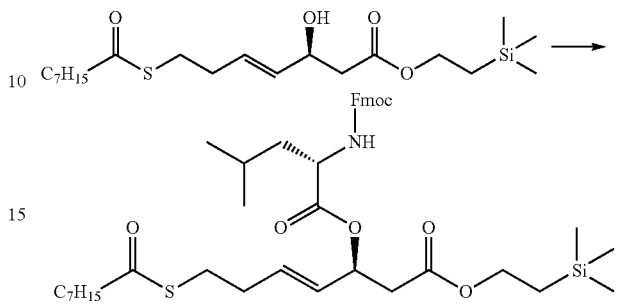

150 mg of raw material (0.375 mmol, 1 eq) and 266 mg of Fmoc-Leu-OH (0.75 mmol, 2 eq) are dissolved into 4 mL of anhydrous dichloromethane, 8.4 mg of DMAP (0.075 mmol, 0.2 eq) is added into the mixture, and 155 mg of DCC (0.75 mmol, 2 eq) is added into the mixture at 0° C. The mixture reacts for 1 h at 0° C., and is filtered to remove the solid, evaporated in vacuum to remove the solvent, and purified by column chromatography (ethyl acetate:petroleum ether=1:10) to obtain 292 mg of colorless liquid with the yield of 100%.

Embodiment 30

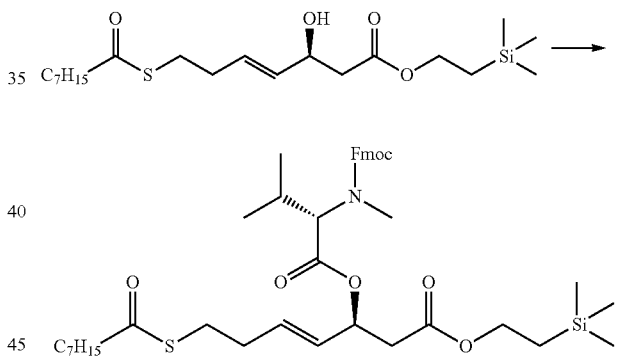

210 mg of raw material (0.52 mmol, 1 eq) and 554 mg of Fmoc-N-Me-Val-OH (1.57 mmol, 3 eq) are dissolved into 10 mL of anhydrous dichloromethane, 12.6 mg of DMAP (0.1 mmol, 0.2 eq) is added into the mixture, and 300 mg of EDCl (1.57 mmol, 3 eq) and 0.26 mL of DIPEA (1.57 mmol, 3 eq) are added into the mixture at 0° C. The mixture reacts for 3 h at 0° C., is diluted with 15 mL of dichloromethane, extracted in turn with diluted HCl (20 mL×2) and saturated NaCl (20 mL×2), dried with anhydrous sodium sulfate, evaporated in vacuum, and purified by column chromatography (ethyl acetate:petroleum ether=1:10) to obtain 320 mg of colorless liquid with the yield of 83.3%.

Embodiment 31

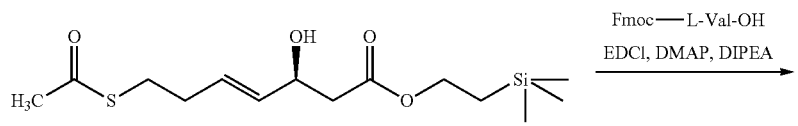

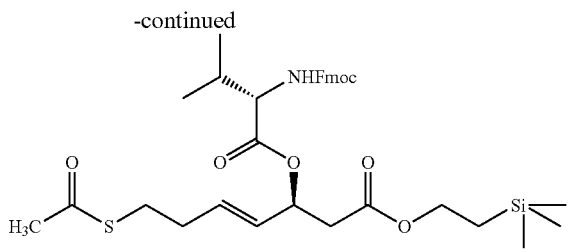

Fmoc-L-Ala-OH (0.363 g, 1.17 mmol), DCC (0.241 g, 1.17 mmol) and DMAP (0.014 g, 0.12 mmol) are in turn added to the solution of compound (0.185 g, 0.58 mmol) in dichloromethane under argon at 0° C., and stirred overnight at room temperature. The mixture is filtered, evaporated in vacuum, and purified by column chromatography (petroleum ether:ethyl acetate=20:1 to 10:1) to obtain 0.252 g of clear liquid with the yield of 68%.

Embodiment 32

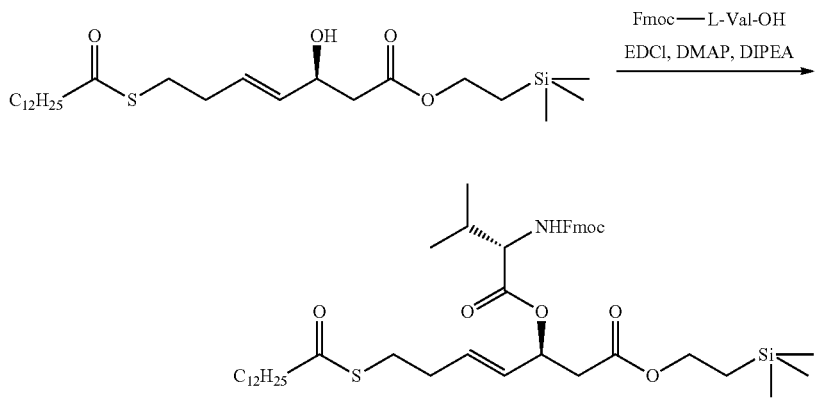

Fmoc-L-Ala-OH (0.436 g, 1.4 mmol), DCC (0.29 g, 1.4 mmol) and DMAP (0.017 g, 0.144 mmol) are in turn added to the solution of compound (0.331 g, 0.7 mmol) in dichloromethane under argon at 0° C., and stirred overnight at room temperature. The mixture is filtered, evaporated in vacuum, and purified by column chromatography (petroleum ether: ethyl acetate=20:1 to 10:1) to obtain 0.394 g of clear liquid with the yield of 71%.

Embodiment 33

Fmoc-L-Ala-OH (0.48 g, 1.54 mmol), DCC (0.32 g, 1.54 mmol) and DMAP (0.019 g, 0.154 mmol) are in turn added to the solution of compound (0.304 g, 0.77 mmol) in dichloromethane under argon at 0° C., and stirred overnight at room temperature. The mixture is filtered, evaporated in vacuum, and purified by column chromatography (petroleum ether: ethyl acetate=20:1 to 10:1) to obtain 0.341 g of clear liquid with the yield of 59%.

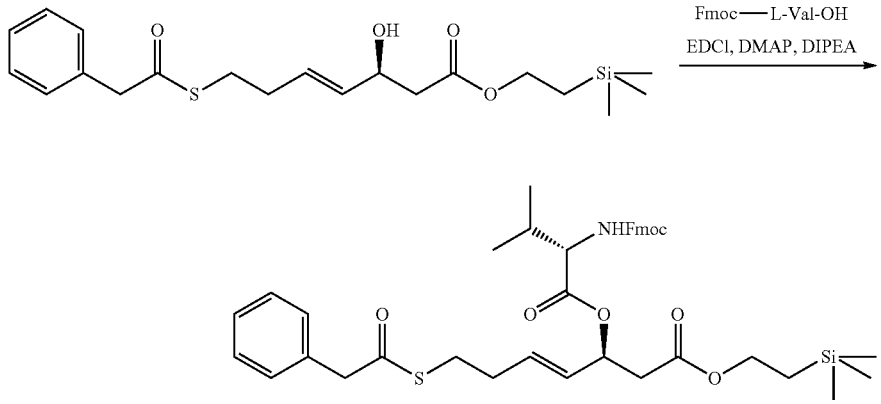

Embodiment 34

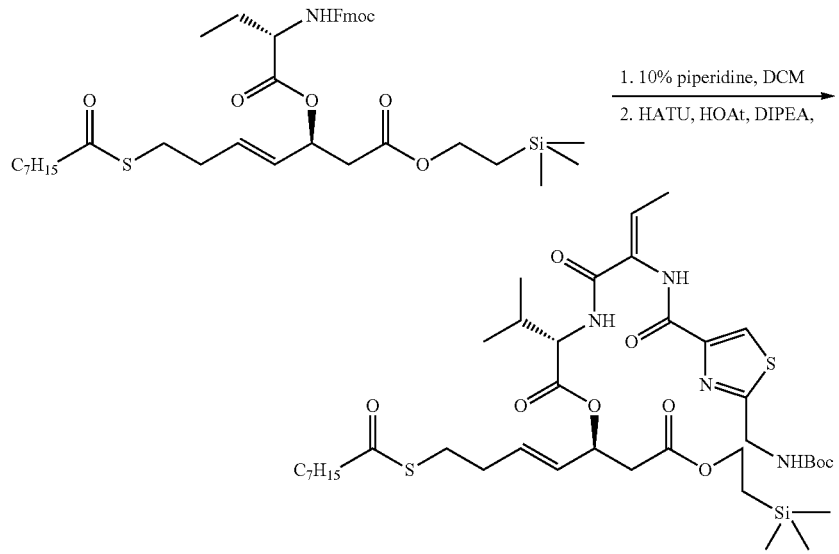

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1) to obtain 0.776 g of colorless liquid with the yield of 78%.

The compound (0.283 g, 0.57 mmol) obtained in the last step is dissolved into dichloromethane under argon; and compound (0.234 g, 0.69 mmol), HATU (0.325 g, 0.86 mmol), HOAt (0.117 g, 0.86 mmol) and DIPEA (0.3 mL, 1.71 mmol) are in turn added into the mixture at 0° C., and stirred overnight at room temperature 1 h later. The mixture is washed in turn with diluted hydrochloric acid and saturated NaCl, dried with anhydrous $Na_2SO_4$, filtered, evaporated in vacuum, and purified by column chromatography (petroleum ether:ethyl acetate=4:1) to obtain 0.378 g of solid with the yield of 81%.

Embodiment 35

Raw material (0.328 g, 0.47 mmol) is dissolved into dichloromethane, and piperidine (0.23 mL, 2.35 mmol) is added into the mixture and stirred for 2 h at room temperature. The mixture is directly evaporated and quickly purified by column chromatography (petroleum ether:ethyl acetate=10:1) to obtain 0.178 of colorless liquid with the yield of 80%.

The compound (0.218 g, 0.46 mmol) obtained in the last step is dissolved into dichloromethane under argon; and compound (0.188 g, 0.552 mmol), HATU (0.262 g, 0.69 mmol), HOAt (0.094 g, 0.69 mmol) and DIPEA (0.23 mL, 1.38 mmol) are in turn added into the mixture at 0° C., and stirred overnight at room temperature 1 h later. The mixture is washed in turn with diluted hydrochloric acid and saturated NaCl, dried with anhydrous $Na_2SO_4$, filtered, evaporated in vacuum, and purified by column chromatography (petroleum ether:ethyl acetate=2:1) to obtain 0.280 g of solid with the yield of 76%.

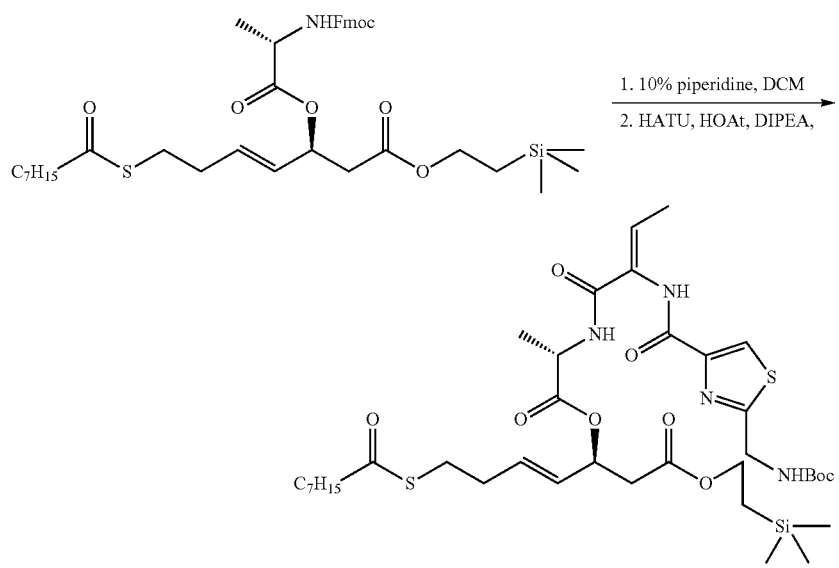

Embodiment 36

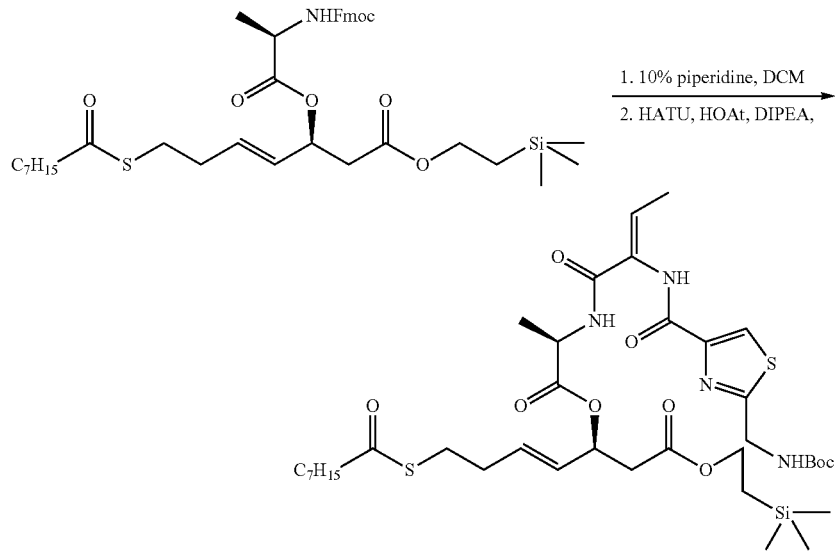

25

Raw material (0.375 g, 0.53 mmol) is dissolved into dichloromethane, and piperidine (0.27 mL, 2.7 mmol) is added into the mixture and stirred for 2 h at room temperature. The mixture is directly evaporated and quickly purified by column chromatography (petroleum ether:ethyl acetate=10:1) to obtain 0.176 g of colorless liquid with the yield of 70%.

The compound (0.15 g, 0.32 mmol) obtained in the last step is dissolved into anhydrous dichloromethane under argon; and compound (0.130 g, 0.38 mmol), HATU (0.183 g, 0.48 mmol), HOAt (0.066 g, 0.48 mmol) and DIPEA (0.16 mL, 0.96 mmol) are in turn added into the mixture at 0° C., and stirred overnight at room temperature 1 h later. The mixture is washed in turn with diluted hydrochloric acid and saturated NaCl, dried with anhydrous Na$_2$SO$_4$, filtered, evaporated in vacuum, and purified by column chromatography (petroleum ether:ethyl acetate=2:1) to obtain 0.184 g of solid with the yield of 72%.

Embodiment 37

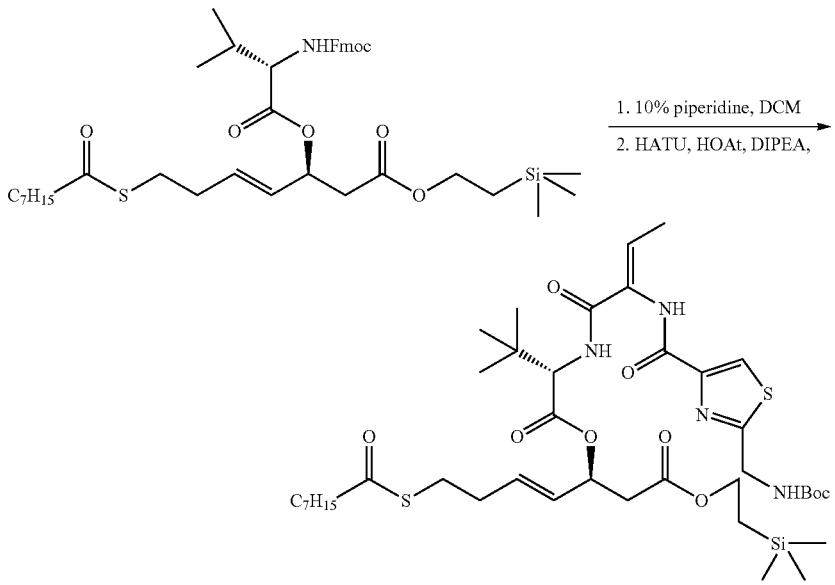

Raw material (0.29 g, 0.4 mmol) is dissolved into dichloromethane, and piperidine (0.2 mL, 2 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.146 g of colorless liquid with the yield of 71%.

The compound (0.119 g, 0.23 mmol) obtained in the last step is dissolved into anhydrous dichloromethane under argon; and compound (0.095 g, 0.28 mmol), HATU (0.131 g, 0.35 mmol), HOAt (0.048 g, 0.35 mmol) and DIPEA (0.12 mL, 0.69 mmol) are in turn added into the mixture at 0° C., and stirred overnight at room temperature 1 h later. The mixture is washed in turn with diluted hydrochloric acid and saturated NaCl, dried with anhydrous $Na_2SO_4$, filtered, evaporated in vacuum, and purified by column chromatography (petroleum ether:ethyl acetate=2:1) to obtain 0.151 g of solid with the yield of 78%.

Embodiment 38

The compound (0.142 g, 0.26 mmol) obtained in the last step is dissolved into anhydrous dichloromethane under argon; and compound (0.106 g, 0.31 mmol), HATU (0.148 g, 0.39 mmol), HOAt (0.053 g, 0.39 mmol) and DIPEA (0.13 mL, 0.78 mmol) are in turn added into the mixture at 0° C., and stirred overnight at room temperature 1 h later. The mix-

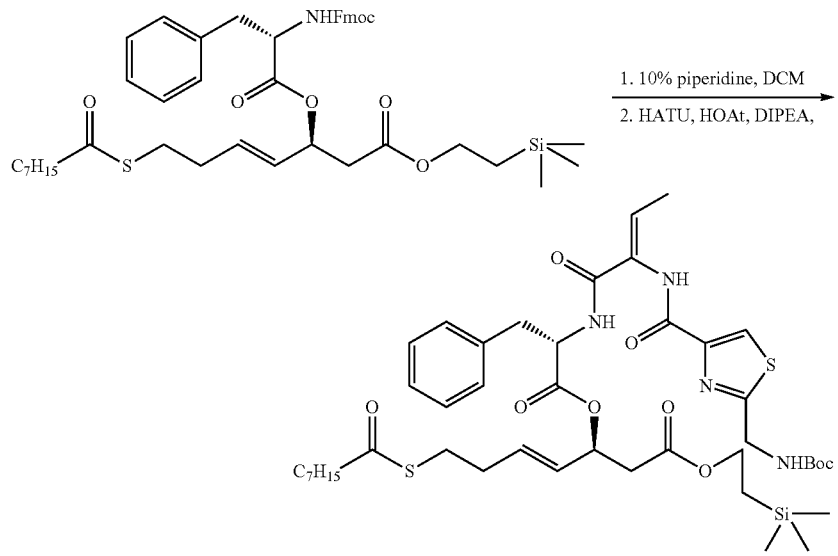

Raw material (0.221 g, 0.29 mmol) is dissolved into dichloromethane, and piperidine (0.14 mL, 1.43 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.142 g of colorless liquid with the yield of 89%.

ture is washed with diluted hydrochloric acid and saturated NaCl in turn, dried with anhydrous $Na_2SO_4$, filtered, evaporated in vacuum, and purified by column chromatography (petroleum ether:ethyl acetate=2:1) to obtain 0.152 g of solid with the yield of 67%.

Embodiment 39

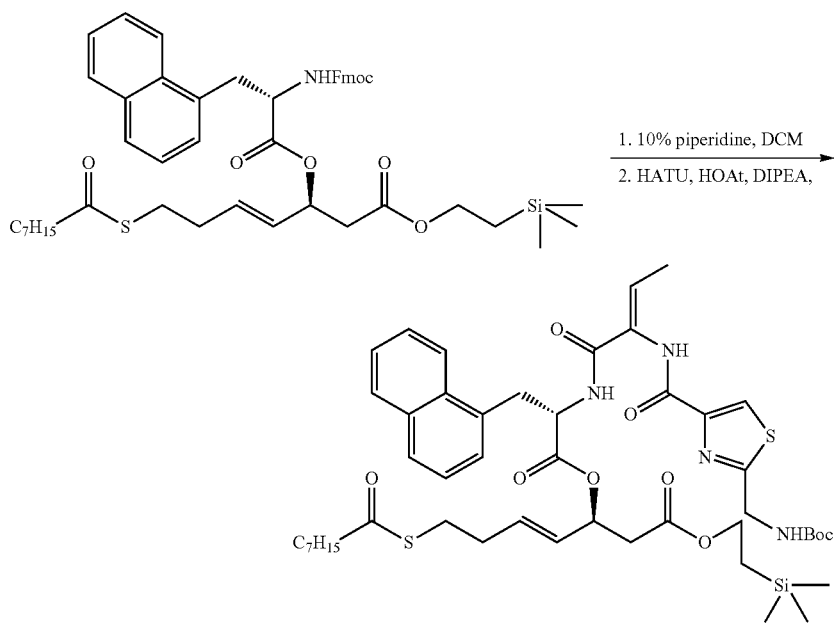

Raw material (0.396 g, 0.68 mmol) is dissolved into dichloromethane, and piperidine (0.24 mL, 2.4 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.23 g of colorless liquid with the yield of 80%.

The compound (0.212 g, 0.35 mmol) obtained in the last step is dissolved into anhydrous dichloromethane under argon; and compound (0.145 g, 0.42 mmol), HATU (0.2 g, 0.53 mmol), HOAt (0.073 g, 0.53 mmol) and DIPEA (0.18 mL, 1.05 mmol) are in turn added into the mixture at 0° C., and stirred overnight at room temperature 1 h later. The mixture is washed in turn with diluted hydrochloric acid and saturated NaCl, dried with anhydrous Na$_2$SO$_4$, filtered, evaporated in vacuum, and purified by column chromatography (petroleum ether:ethyl acetate=2:1) to obtain 0.241 g of solid with the yield of 75%.

Embodiment 40

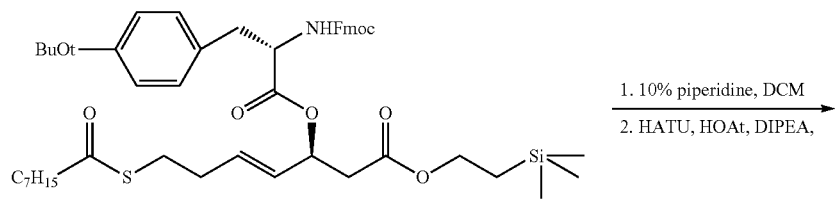

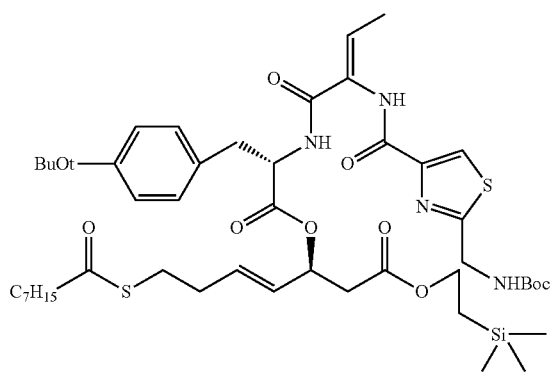

Raw material (0.464 g, 0.55 mmol) is dissolved into dichloromethane, and piperidine (0.27 mL, 2.75 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.2962 g of colorless liquid with the yield of 87%.

The compound (0.296 g, 0.48 mmol) obtained in the last step is dissolved into anhydrous dichloromethane under argon; and compound (0.197 g, 0.576 mmol), HATU (0.274 g, 0.72 mmol), HOAt (0.098 g, 0.72 mmol) and DIPEA (0.24 mL, 1.44 mmol) are in turn added into the mixture at 0° C., and stirred overnight at room temperature 1 h later. The mixture is washed in turn with diluted hydrochloric acid and saturated NaCl, dried with anhydrous Na$_2$SO$_4$, filtered, evaporated in vacuum, and purified by column chromatography (petroleum ether:ethyl acetate=2:1) to obtain 0.192 g of solid with the yield of 42%.

Embodiment 41

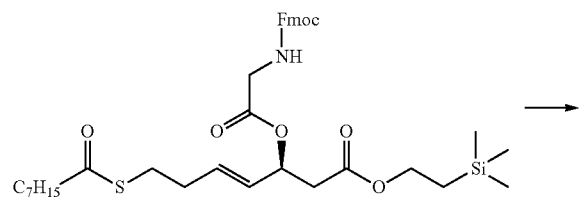

-continued

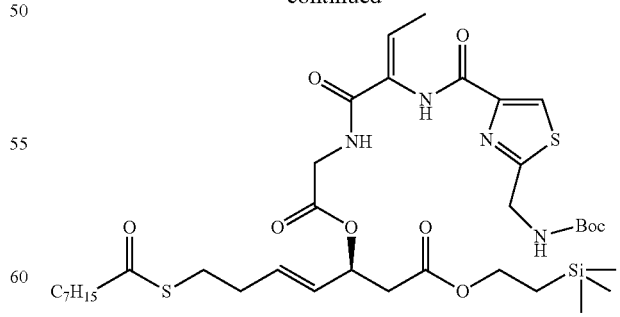

170 mg of raw material (0.25 mmol, 1 eq) is dissolved into 2 mL of anhydrous acetonitrile, 0.1 mL of piperidine is added into the mixture and stirred for 2 h at room temperature, and the mixture is evaporated in vacuum to remove the solvent. 5 mL of anhydrous dichloromethane is added into the mixture, 85 mg of (S)-2-(2-(((tert-butoxycarbonyl)amino)-methyl) thiazole-4-carboxamido) butanoic acid (0.25 mmol, 1 eq) is added into the mixture at 0° C., and then 51 mg of HOAT (0.375 mmol, 1.5 eq), 143 mg of HATU (0.375 mmol, 1.5 eq) and 0.12 mL of DIPEA (0.75 mmol, 3 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 155 mg of colorless liquid with the yield of 81.7%.

Embodiment 42

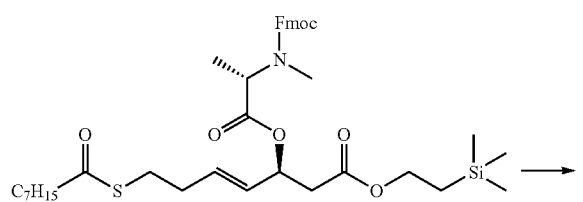

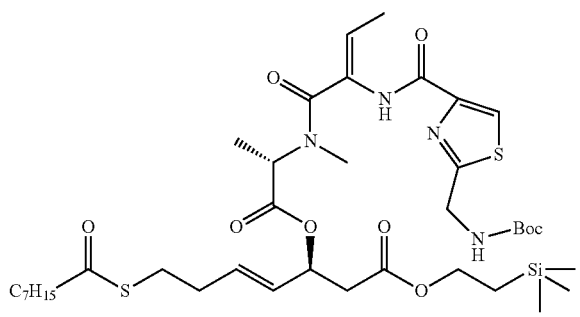

180 mg of raw material (0.35 mmol, 1 eq) is dissolved into 2 mL of anhydrous acetonitrile, and 0.1 mL of piperidine is added into the mixture and stirred for 2 h at room temperature, and the mixture is evaporated in vacuum to remove the solvent. 5 mL of anhydrous dichloromethane is added into the mixture, 179 mg of (S)-2-(2-(((tert-butoxycarbonyl)amino)-methyl)thiazole-4-carboxamido) butanoic acid (0.525 mmol, 1.5 eq) is added into the mixture at 0° C., and then 95 mg of HOAT (0.7 mmol, 2 eq), 266 mg of HATU (0.7 mmol, 2 eq) and 0.12 mL of DIPEA (0.4 mmol, 4 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 110 mg of colorless liquid with the yield of 81.7%.

Embodiment 43

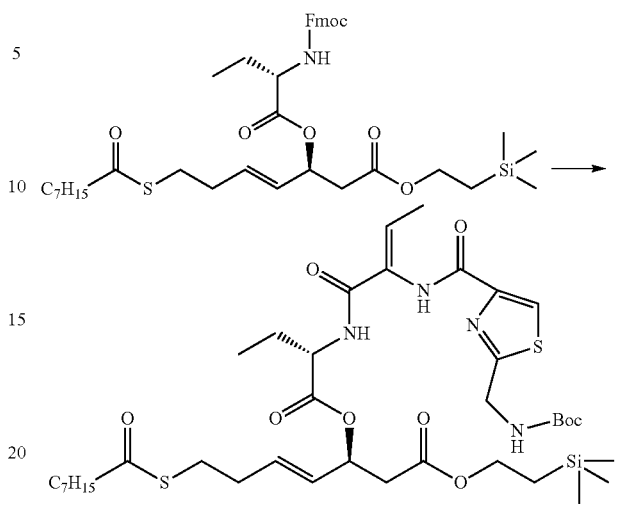

160 mg of raw material (0.35 mmol, 1 eq) is dissolved into 2 mL of anhydrous acetonitrile, and 0.1 mL of piperidine is added into the mixture and stirred for 2 h at room temperature, and the mixture is evaporated in vacuum to remove the solvent. 5 mL of anhydrous dichloromethane is added into the mixture, 85 mg of (S)-2-(2-(((tert-butoxycarbonyl)amino)-methyl) thiazole-4-carboxamido) butanoic acid (0.25 mmol, 1.1 eq) is added into the mixture at 0, and then 51 mg HOAT (0.375 mmol, 1.5 eq), 143 mg of HATU (0.375 mmol, 1.5 eq) and 0.12 mL of DIPEA (0.75 mmol, 3 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 120 mg of colorless liquid with the yield of 81.7%.

Embodiment 44

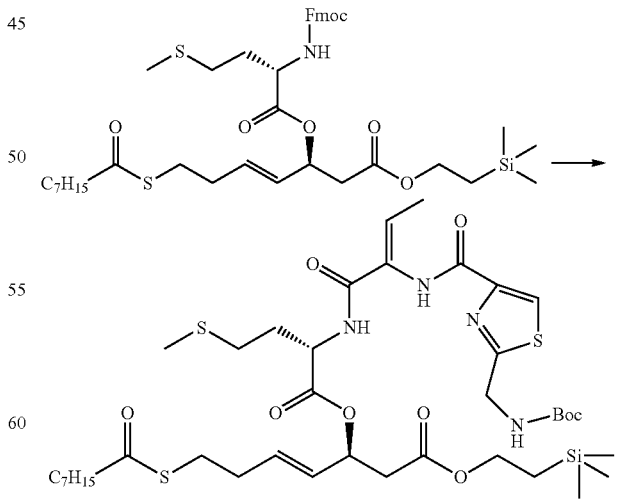

270 mg of raw material (0.357 mmol, 1 eq) is dissolved into 2 mL of anhydrous acetonitrile, and 0.1 mL of piperidine is added into the mixture and stirred for 2 h at room temperature, and the mixture is evaporated in vacuum to remove the solvent. 5 mL of anhydrous dichloromethane is added into the mixture, 134 mg of (S)-2-(2-(((tert-butoxycarbonyl)amino)methyl)thiazole-4-carboxamido) butanoic acid (0.393 mmol, 1.1 eq) is added into the mixture at 0° C., and then 73 mg of HOAT (0.536 mmol, 1.5 eq), 203 mg of HATU (0.365 mmol, 1.5 eq) and 0.18 mL of DIPEA (0.75 mmol, 3 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 180 mg of colorless liquid with the yield of 58.8%.

Embodiment 45

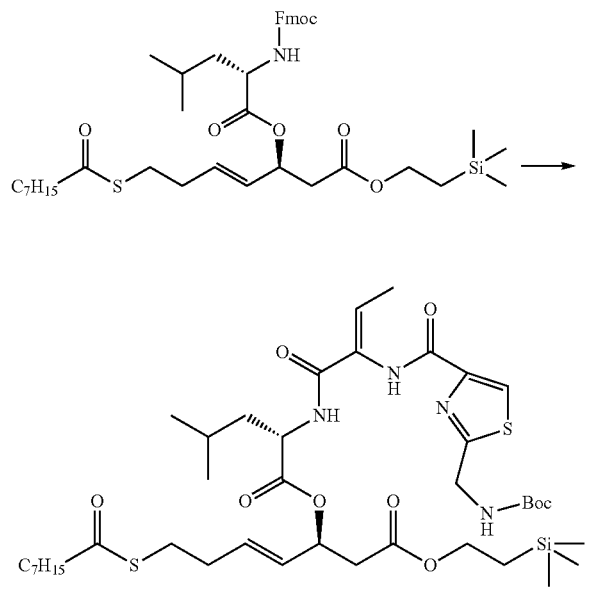

292 mg of raw material (0.375 mmol, 1 eq) is dissolved into 2 mL of anhydrous acetonitrile, and 0.1 mL of piperidine is added into the mixture and stirred for 2 h at room temperature, and the mixture is evaporated in vacuum to remove the solvent. 5 mL of anhydrous dichloromethane is added into the mixture, 141 mg of (S)-2-(2-(((tert-butoxycarbonyl)amino)methyl)thiazole-4-carboxamido) butanoic acid (0.412 mmol, 1.1 eq) is added into the mixture at 0° C., and then 76.5 mg of HOAT (0.562 mmol, 1.5 eq), 214 mg of HATU (0.362 mmol, 1.5 eq) and 0.18 mL of DIPEA (1.125 mmol, 3 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 190 mg of colorless liquid with the yield of 60.4%.

Embodiment 46

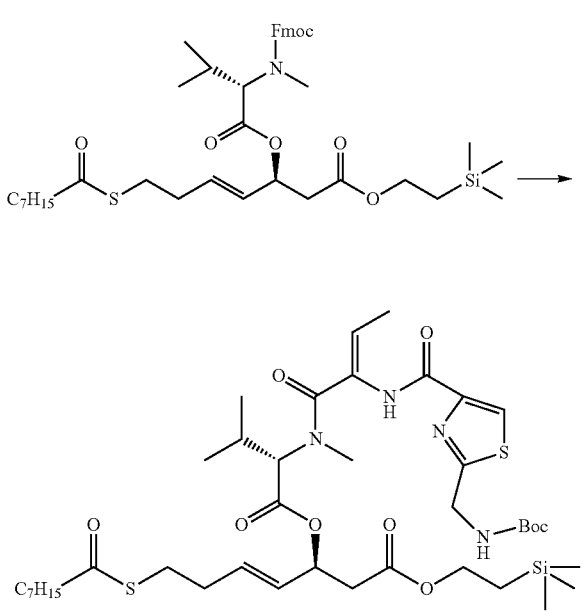

320 mg of raw material (0.433 mmol, 1 eq) is dissolved into 2 mL of anhydrous acetonitrile, and 0.1 mL of piperidine is added into the mixture and stirred for 2 h at room temperature, and the mixture is evaporated in vacuum to remove the solvent. 5 mL of anhydrous dichloromethane is added into the mixture, 295 mg of (S)-2-(2-(((tert-butoxycarbonyl)amino)methyl)thiazole-4-carboxamido) butanoic acid (0.866 mmol, 2 eq) is added into the mixture at 0° C., and then 118 mg of HOAT (0.866 mmol, 2 eq), 330 mg of HATU (0.0.866 mmol, 2 eq) and 0.29 mL of DIPEA (1.732 mmol, 4 eq) are in turn added into the mixture. After these substances are completely added into the mixture, the mixture is warmed to normal temperature for reaction for 2 h and then added with 15 mL of dichloromethane for dilution. The mixture is extracted in turn with diluted HCl (20 mL×2) and saturated NaCl (20 mL×2). The organic layers are dried with anhydrous sodium sulfate, evaporated in vacuum, and purified by column chromatography (ethyl acetate:petroleum ether=1:2) to obtain 57 mg of colorless liquid with the yield of 15.8%.

Embodiment 47

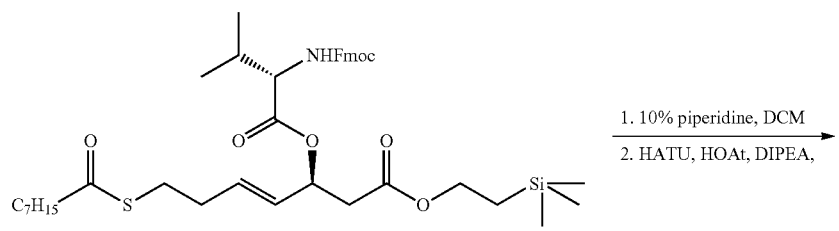

-continued

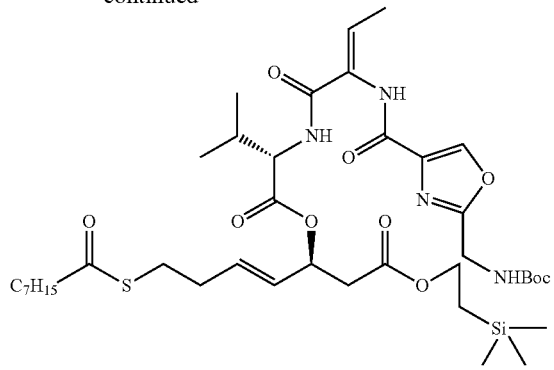

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.535 g, 0.74 mmol) obtained in the last step is dissolved into anhydrous dichloromethane under argon; and compound (0.356 g, 0.9 mmol), HATU (0.0.423 g, 1.12 mmol), HOAt (0.152 g, 1.12 mmol) and DIPEA (0.4 mL, 2.22 mmol) are in turn added into the mixture at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.455 g of solid with the yield of 78%.

Embodiment 48

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.593 g, 0.82 mmol) obtained in the last step is dissolved into anhydrous dichloromethane under argon; and compound (0.452 g, 0.99 mmol), HATU (0.465 g, 1.23 mmol), HOAt (0.167 g, 1.23 mmol) and DIPEA (0.44 mL, 2.44 mmol) and DIPEA (0.4 mL, 2.22 mmol) are in turn added into the mixture at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.412 g of solid with the yield of 61%.

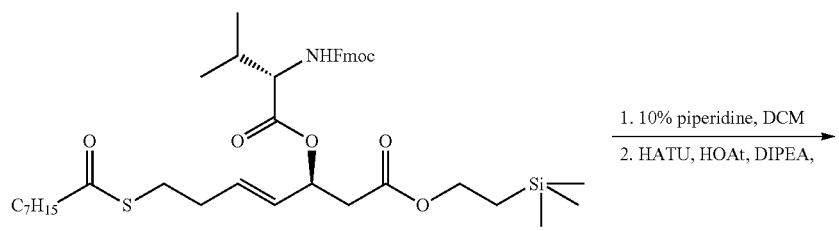

1. 10% piperidine, DCM
2. HATU, HOAt, DIPEA,

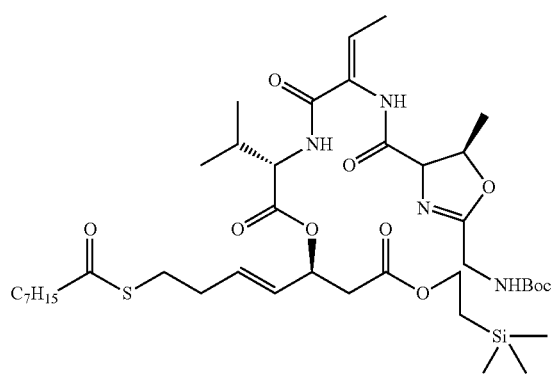

Embodiment 49

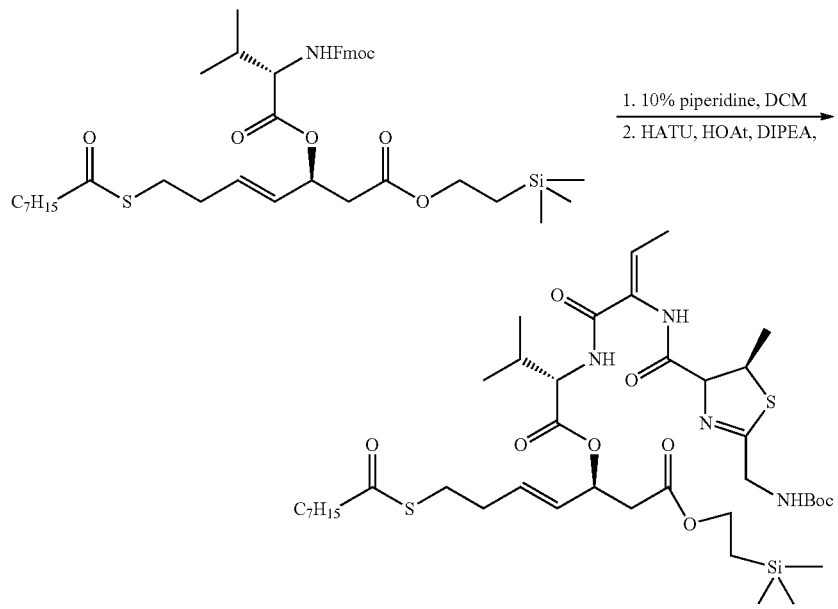

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.412 g, 0.57 mmol) obtained in the last step is dissolved into anhydrous dichloromethane under argon; and compound (0.352 g, 0.69 mmol), HATU (0.326 g, 0.86 mmol), HOAt (0.117 g, 0.86 mmol) and DIPEA (0.31 mL, 1.71 mmol) are in turn added into the mixture at 0° C. and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 0.335 g of solid with the yield of 70%.

Embodiment 50

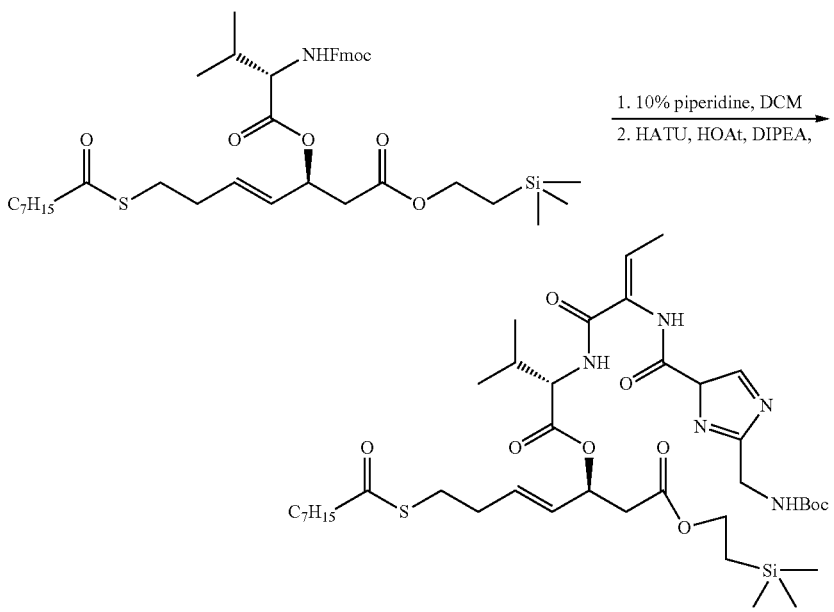

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.412 g, 0.45 mmol) obtained in the last step is dissolved into anhydrous dichloromethane under argon; and compound (0.352 g, 0.55 mmol), HATU (0.261 g, 0.69 mmol), HOAt (0.094 g, 0.69 mmol) and DIPEA (0.25 mL, 1.37 mmol) are in turn added into the mixture at 0° C. and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.265 g of solid with the yield of 73%.

Embodiment 51

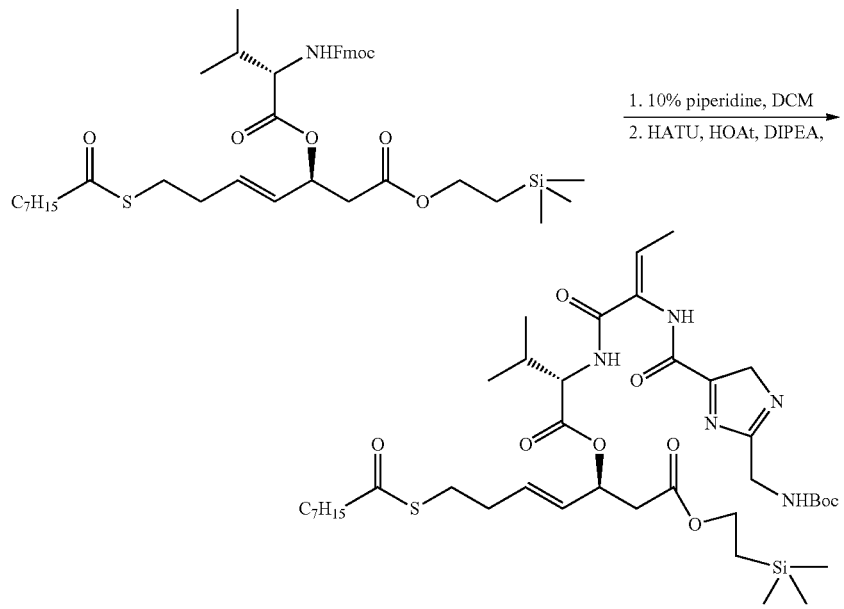

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.412 g, 0.45 mmol) obtained in the last step is dissolved into anhydrous dichloromethane under argon; and compound (0.313 g, 0.55 mmol), HATU (0.261 g, 0.69 mmol), HOAt (0.094 g, 0.69 mmol) and DIPEA (0.25 mL, 1.37 mmol) are in turn added into the mixture at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.265 g of solid with the yield of 73%.

Embodiment 52

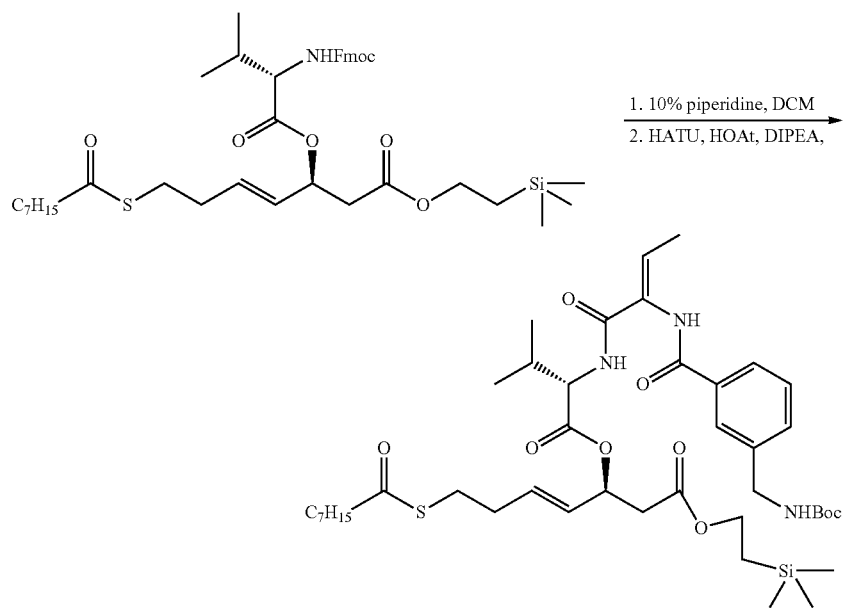

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.412 g, 0.585 mmol) obtained in the last step is dissolved into anhydrous dichloromethane under argon; and compound (0.485 g, 0.72 mmol), HATU (0.34 g, 0.9 mmol), HOAt (0.122 g, 0.9 mmol) and DIPEA (0.33 mL, 1.78 mmol) are in turn added into the mixture at 0° C., and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 0.392 g of solid with the yield of 82%.

Embodiment 53

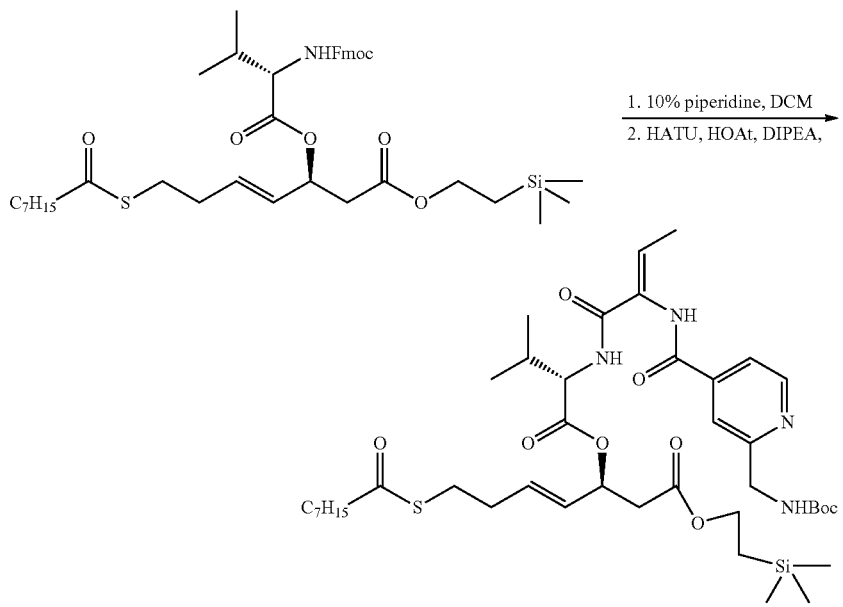

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.412 g, 0.585 mmol) obtained in the last step is dissolved into anhydrous dichloromethane under argon; and compound (0.512 g, 0.936 mmol), HATU (0.442 g, 1.17 mmol), HOAt (0.159 g, 1.17 mmol) and DIPEA (0.43 mL, 2.31 mmol) are in turn added into the mixture at 0° C., and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 0.46 g of solid with the yield of 74%.

Embodiment 54

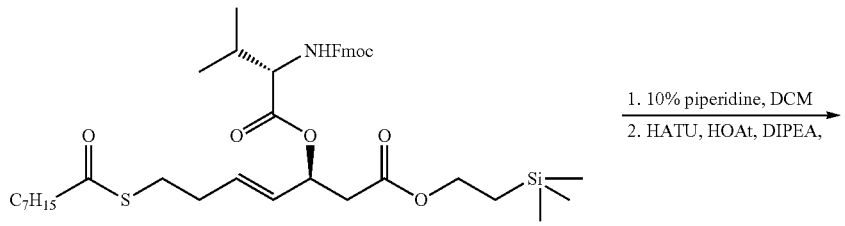

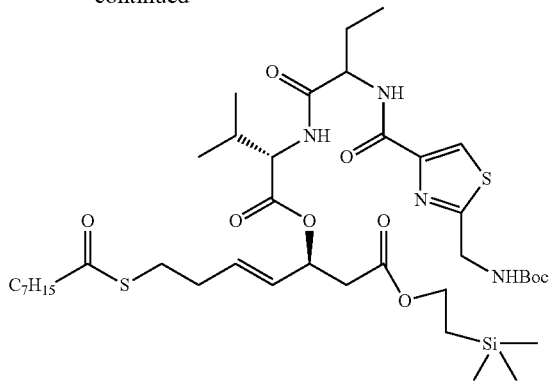

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.283 g, 0.57 mmol) obtained in the last step is dissolved into anhydrous dichloromethane under argon; and compound (0.214 g, 0.69 mmol), HATU (0.325 g, 0.86 mmol), HOAt (0.117 g, 0.86 mmol) and DIPEA (0.3 mL, 1.71 mmol) are in turn added into the mixture at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.377 g of solid with the yield of 80%.

Embodiment 55

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.212 g, 0.43 mmol) obtained in the last step is dissolved into anhydrous dichloromethane under argon; and compound (0.16 g, 0.52 mmol), HATU (0.244 g, 0.65 mmol), HOAt (0.088 g, 0.65 mmol) and DIPEA (0.23 mL, 1.28 mmol) are in turn added into the mixture at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.306 g of solid with the yield of 89%.

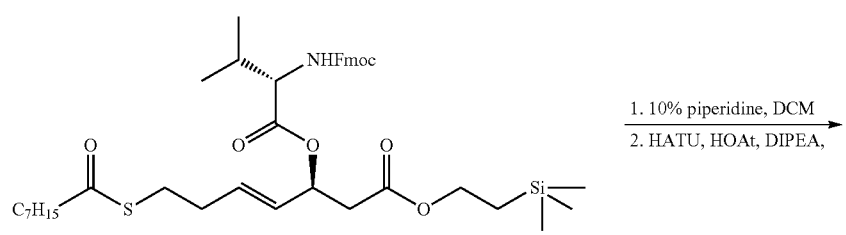

1. 10% piperidine, DCM
2. HATU, HOAt, DIPEA,

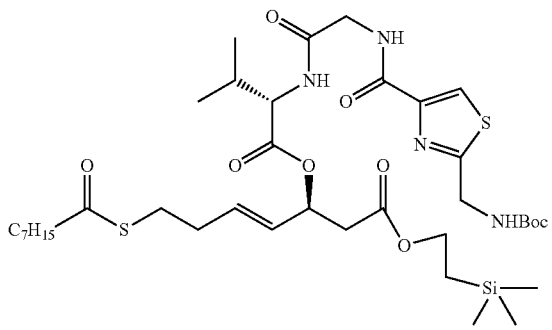

Embodiment 56

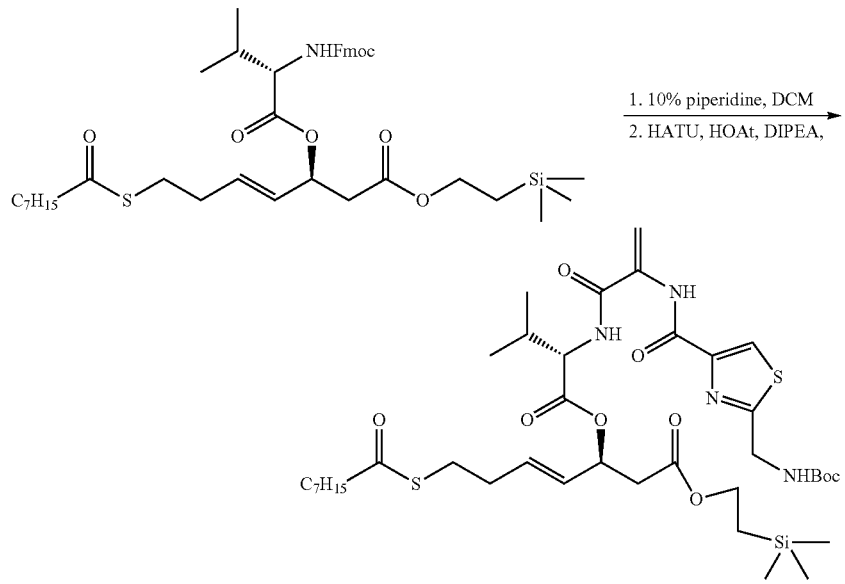

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.425 g, 0.86 mmol) obtained in the last step is dissolved into anhydrous dichloromethane under argon; and compound (0.341 g, 1.04 mmol), HATU (0.488 g, 1.3 mmol), HOAt (0.175 g, 1.3 mmol) and DIPEA (045 mL, 2.67 mmol) are in turn added into the mixture at 0° C., and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 0.446 g of solid with the yield of 64%.

Embodiment 57

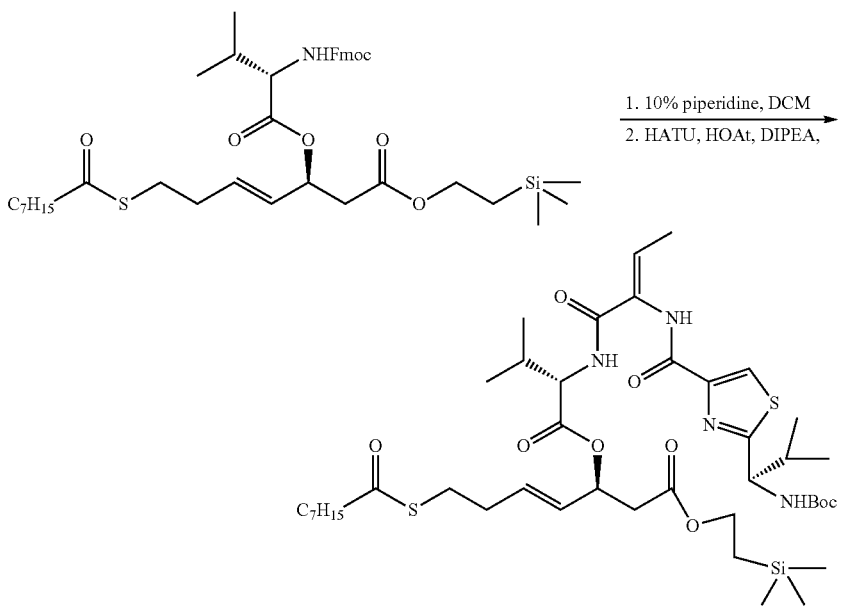

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.396 g, 0.798 mmol) obtained in the last step is dissolved into anhydrous dichloromethane under argon; and compound (0.352 g, 0.966 mmol), HATU (0.455 g, 1.2 mmol), HOAt (0.164 g, 1.2 mmol) and DIPEA (0.3 mL, 0.42 mmol) are in turn added into the mixture at 0° C., and stirred overnight at room temperature 1 h later. The mixture is washed with diluted hydrochloric acid and saturated NaCl in turn, dried with anhydrous Na₂SO₄, filtered, evaporated in vacuum, and purified by column chromatography (petroleum ether:ethyl acetate=4:1) to obtain 0.581 g of solid with the yield of 84%.

Embodiment 58

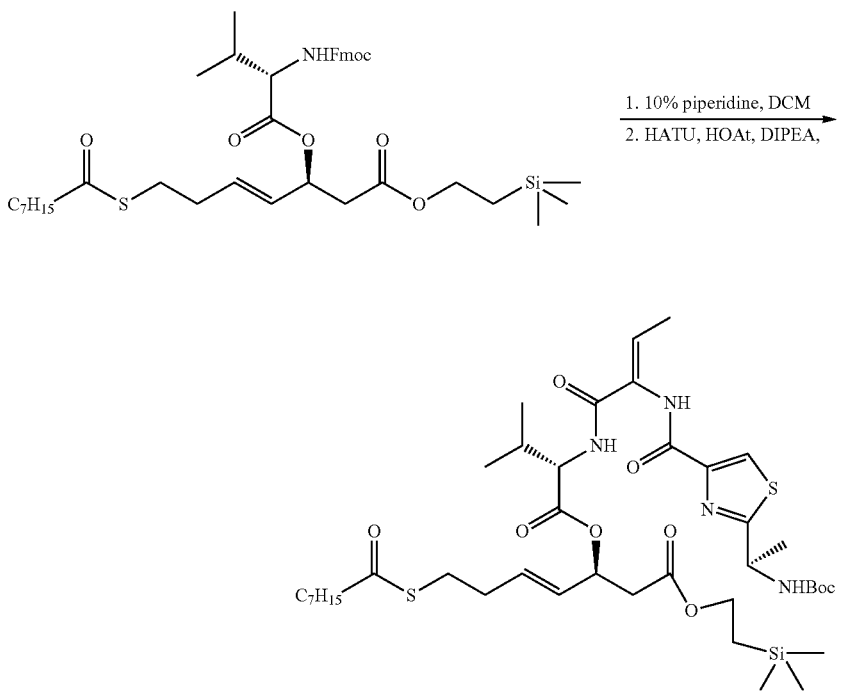

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.24 g, 0.485 mmol) obtained in the last step is dissolved into anhydrous dichloromethane under argon; and compound (0.212 g, 0.59 mmol), HATU (0.276 g, 0.731 mmol), HOAt (0.1 g, 0.731 mmol) and DIPEA (0.255 mL, 1.45 mmol) are in turn added into the mixture at 0° C., and stirred overnight at room temperature 1 h later. The mixture is washed with diluted hydrochloric acid and saturated NaCl in turn, dried with anhydrous Na₂SO₄, filtered, evaporated in vacuum, and purified by column chromatography (petroleum ether:ethyl acetate=4:1) to obtain 0.358 g of solid with the yield of 88%.

Embodiment 59

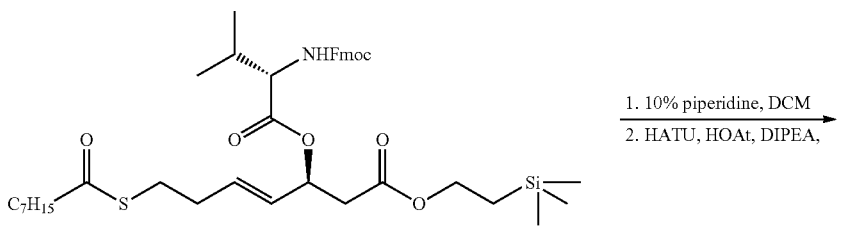

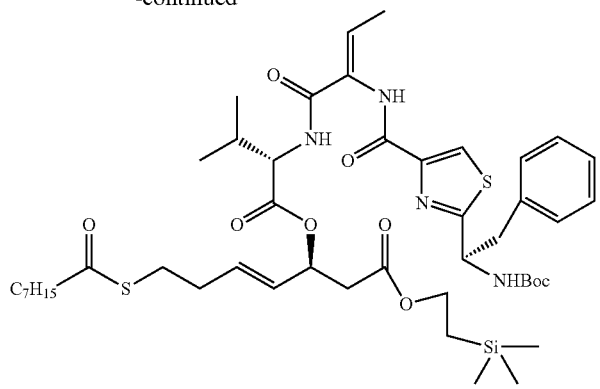

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.318 g, 0.64 mmol) obtained in the last step is dissolved into anhydrous dichloromethane under argon; and compound (0.295 g, 0.78 mmol), HATU (0.366 g, 0.97 mmol), HOAt (0.132 g, 0.97 mmol) and DIPEA (0.34 mL, 1.92 mmol) are in turn added into the mixture at 0° C., and stirred overnight at room temperature 1 h later. The mixture is washed with diluted hydrochloric acid and saturated NaCl in turn, dried with anhydrous Na₂SO₄, filtered, evaporated in vacuum, and purified by column chromatography (petroleum ether:ethyl acetate=4:1) to obtain 0.474 g of solid with the yield of 81%.

Embodiment 60

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.776 g of colorless liquid with the yield of 78%.

The compound (0.283 g, 0.57 mmol) obtained in the last step is dissolved into anhydrous dichloromethane under argon; and compound (0.453 g, 0.69 mmol), HATU (0.325 g, 0.86 mmol), HOAt (0.117 g, 0.86 mmol) and DIPEA (0.3 mL, 1.71 mmol) are in turn added into the mixture at 0° C., and stirred overnight at room temperature 1 h later. The mixture is washed with diluted hydrochloric acid and saturated NaCl in turn, dried with anhydrous Na₂SO₄, filtered, evaporated in vacuum, and purified by column chromatography (petroleum ether:ethyl acetate=4:1) to obtain 0.298 g of solid with the yield of 53%.

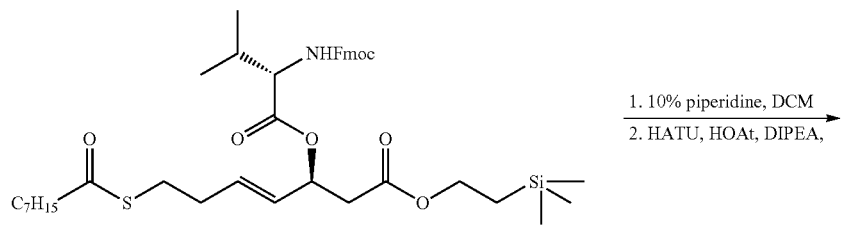

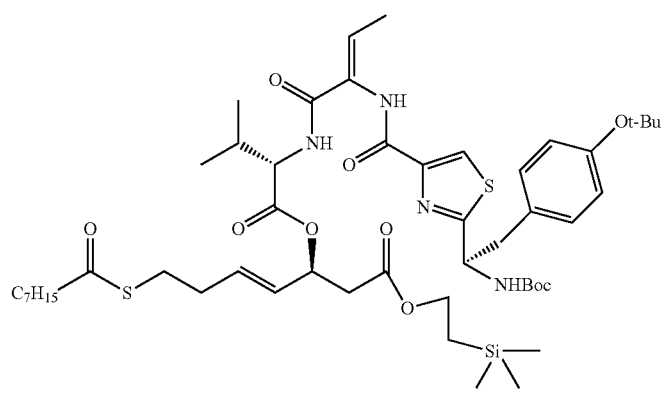

Embodiment 61

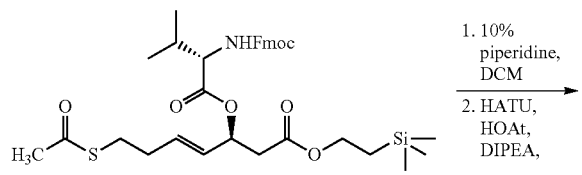

The compound (0.626 g, 1.5 mmol) obtained in the last step is dissolved into anhydrous dichloromethane under argon; and compound (1.62 g, 1.56 mmol), HATU (0.855 g, 2.26 mmol), HOAt (0.117 g, 2.26 mmol) and DIPEA (0.79 mL, 4.5 mmol) are in turn added into the mixture at 0° C., and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 1.05 g of solid with the yield of 91%.

Embodiment 62

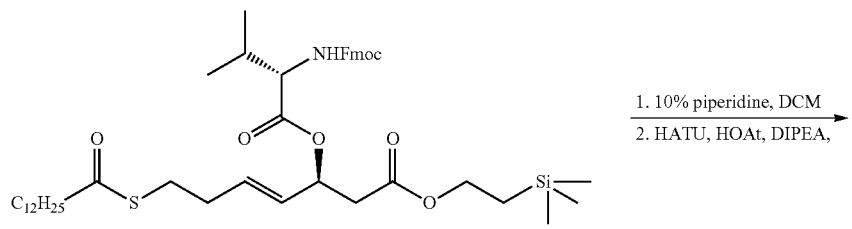

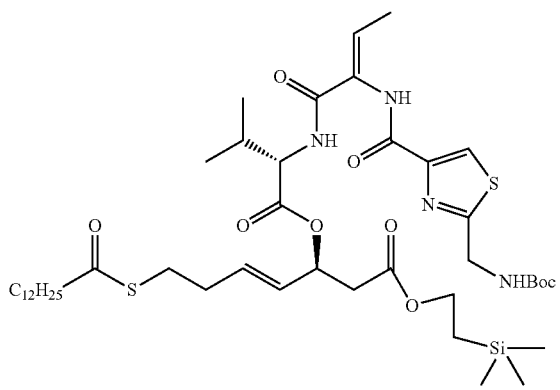

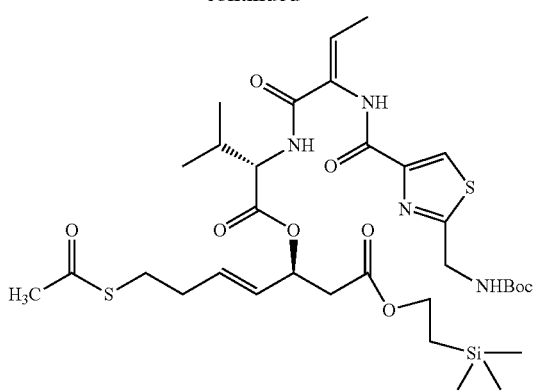

Raw material (1.28 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.626 g of colorless liquid with the yield of 75%.

Raw material (1.587 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.724 g of colorless liquid with the yield of 65%.

The compound (0.326 g, 0.57 mmol) obtained in the last step is dissolved into anhydrous dichloromethane under argon; and compound (0.234 g, 0.69 mmol), HATU (0.325 g, 0.86 mmol), HOAt (0.117 g, 0.86 mmol) and DIPEA (0.3 mL, 1.71 mmol) are in turn added into the mixture at 0° C., and stirred overnight at room temperature 1 h later. The mixture is washed with diluted hydrochloric acid and saturated NaCl in turn, dried with anhydrous $Na_2SO_4$, filtered, evaporated in vacuum, and purified by column chromatography (petroleum ether:ethyl acetate=4:1) to obtain 0.428 g of solid with the yield of 84%.

Embodiment 63

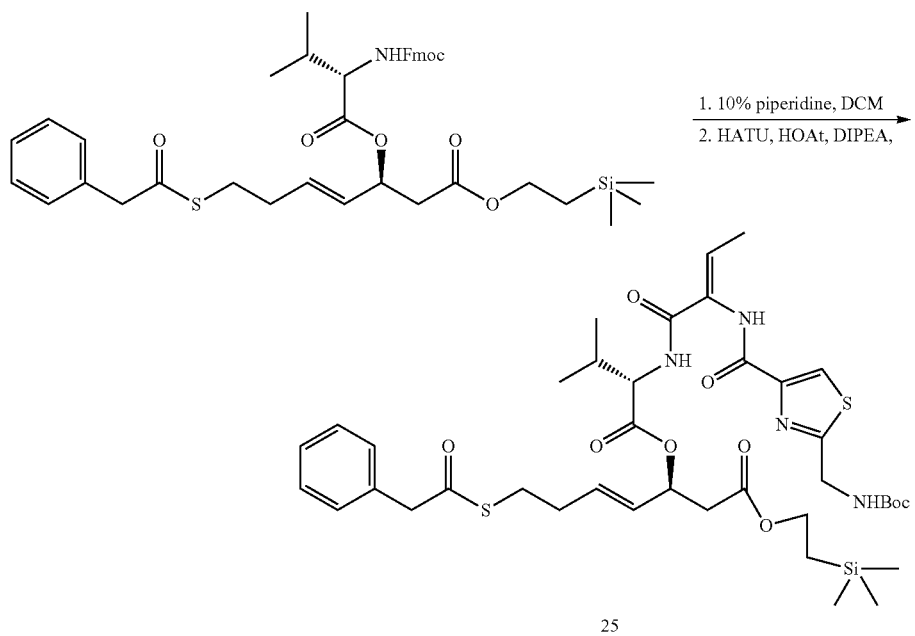

Raw material (1.43 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 0.711 g of colorless liquid with the yield of 72%.

The compound (0.281 g, 0.57 mmol) obtained in the last step is dissolved into anhydrous dichloromethane under argon; and compound (0.234 g, 0.69 mmol), HATU (0.325 g, 0.86 mmol), HOAt (0.117 g, 0.86 mmol) and DIPEA (0.3 mL, 1.71 mmol) are added in turn at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.363 g of solid with the yield of 78%.

Embodiment 64

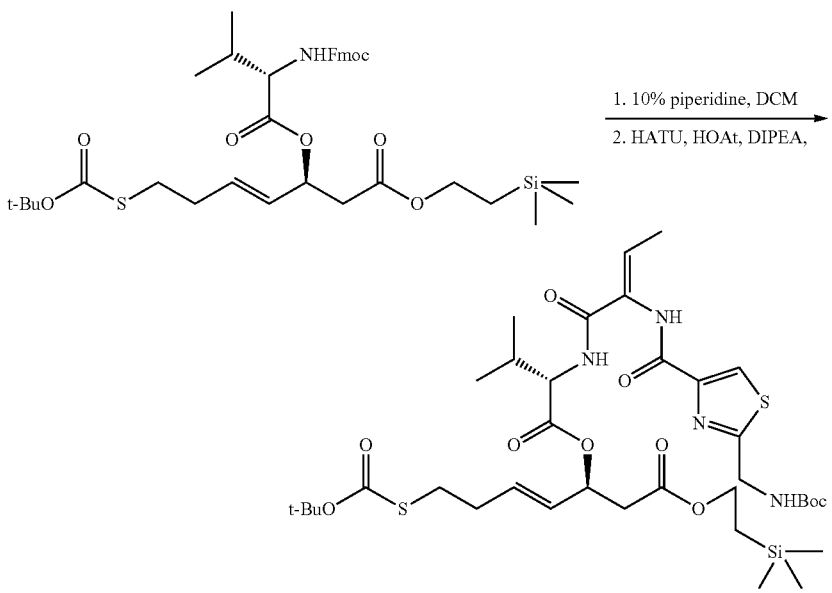

Raw material (1.45 g, 2 mmol) is dissolved into dichloromethane, and piperidine (1 mL, 10 mmol) is added into the mixture and stirred for 2 h at room temperature. The mixture is directly evaporated and quickly purified by column chromatography (petroleum ether:ethyl acetate=10:1, dichloromethane:methanol=10:1) to obtain 1.39 g of colorless liquid with the yield of 84%.

The compound (0.612 g, 0.74 mmol) obtained in the last step are dissolved into anhydrous dichloromethane under argon; and compound (0.356 g, 0.9 mmol), HATU (0.423 g, 1.12 mmol), HOAt (0.152 g, 1.12 mmol) and DIPEA (0.4 mL, 2.22 mmol) are added in turn at 0° C., and stirred overnight at room temperature 1 h later. The mixture is washed with diluted hydrochloric acid and saturated NaCl in turn, dried with anhydrous Na$_2$SO$_4$, filtered, evaporated in vacuum, and purified by column chromatography (petroleum ether:ethyl acetate=4:1) to obtain 0.391 g of solid with the yield of 64%.

Embodiment 65 Synthesis of Compound of Formula 1-3 concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous Na$_2$SO$_4$, filtered, evaporated in vacuum, and purified by column chromatography (petroleum ether:ethyl acetate:metha-

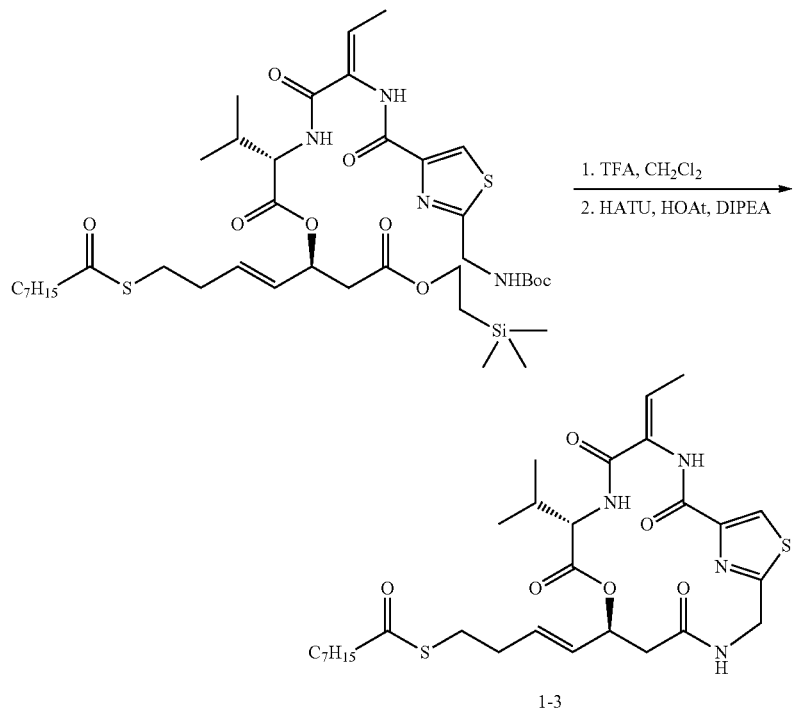

1 mL of trifluoroacetic acid is added into the solution of raw material (0.34 g, 0.41 mmol) in anhydrous dichloromethane (5 mL) prepared in Embodiment 34 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.78 g, 2.05 mmol), HOAt (0.28 g, 2.05 mmol) and DIPEA (0.7 mL, 4.1 mmol) in anhydrous DMF, and stirred for 3 days at 30° C. The nol=20:20:1) to obtain 0.121 g of solid 1-3 with the yield of 49%.

[α]$^{23}$D: 19.2 (c 0.9, CHCl$_3$). $^1$H NMR (400 MHz, CDCl$_3$): δ 8.54(s, 1H), 8.08(s, 1H), 6.97(q, J=7 Hz, 1H), 6.82(m, 1H), 6.51(d, J=10.1 Hz, 1H), 5.74-5.6(m, 2H), 5.47(dd, J=15.5 Hz 6.8 Hz, 1H), 5.14(dd, J=16 Hz 8.2 Hz, 1H), 4.70(dd, J=10.1 Hz 3.2 Hz, 1H) 4.32(dd, J=17.4 Hz, 3.5 Hz, 1H), 2.82(t, J=7.2 Hz, 2H), 2.75-2.59(m, 2H), 2.47(t, J=7.5 Hz, 2H), 2.24(m, 2H), 1.82(d, J=7 Hz, 3H), 1.58(m, 2H), 1.24(m, 8H), 0.83(m, 3H), 0.74(d, J=6.7 Hz, 3H), 0.55(d, J=6.7 Hz, 3H) ppm. MS (EI, m/z): 607 (M$^+$+1), 629 (M$^+$+Na). HRMS (ESI): calcd for C$_{29}$H$_{42}$N$_4$O$_6$S$_2$ [MNa$^+$] 629.2438, found 629.2440.

Embodiment 66 Synthesis of Compound of Formula 1-4

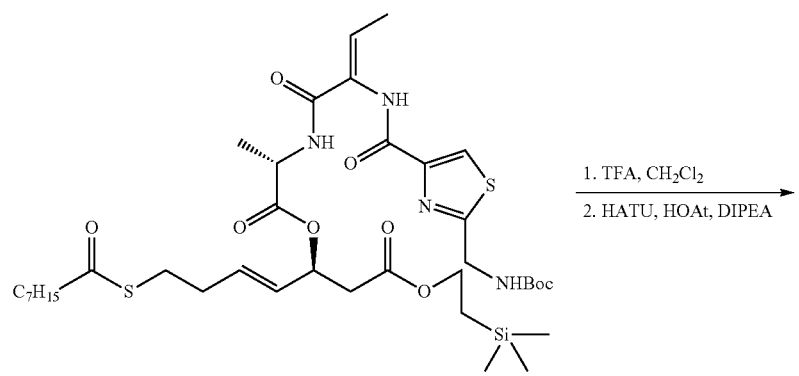

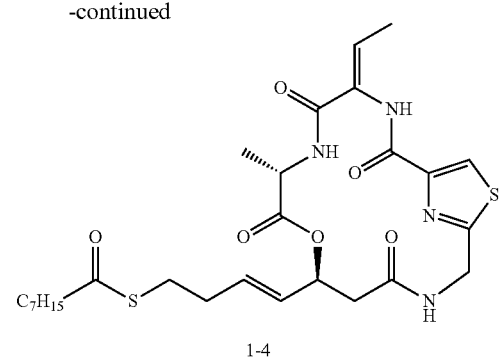

1-4

1 mL of trifluoroacetic acid is added into the solution of raw material (0.279 g, 0.35 mmol) in anhydrous dichloromethane (5 mL) prepared in Embodiment 35 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 40 mL of anhydrous DMF under argon. The mixture is slowly and dropwise added into the solution of HATU (0.665 g, 1.75 mmol), HOAt (0.238 g, 1.75 mmol) and DIPEA (0.58 mL, 3.5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous Na$_2$SO$_4$, filtered, evaporated in vacuum, and purified by column chromatography (petroleum ether:ethyl acetate:methanol=20:20:1) to obtain 0.116 g of solid 1-4 with the yield of 58%.

$[\alpha]^{23}$D: 60.2 (c 0.5, CHCl$_3$). $^1$H NMR (400 MHz, CDCl$_3$): δ 8.67(s, 1H), 8.07(s, 1H), 6.95-6.8(m, 3H), 5.72(m, 2H), 5.42(dd, J=7.1 Hz, 15.5 Hz, 1H), 5.14(dd, J=7.8 Hz, 17.4 Hz, 1H), 4.76(m, 1H), 4.31(dd, J=4.3 Hz, 17.4 Hz, 1H), 2.85(m, 3H), 2.77(m, 1H), 2.63(d, J=16.5 Hz, 1H), 2.50(t, J=7.5 Hz, 2H), 2.25(dd, J=7 Hz, 14 Hz, 2H), 1.79(d, J=7.1 Hz, 3H), 1.61(m, 2H), 1.34-1.2(m, 11H), 0.85(m, 3H) ppm. MS (EI, m/z): 579 (M$^+$+1). HRMS (ESI): calcd for C$_{27}$H$_{38}$N$_4$O$_6$S$_2$ [MNa$^+$] 601.2125, found 601.2129.

Embodiment 67 Synthesis of Compound of Formula 1-5

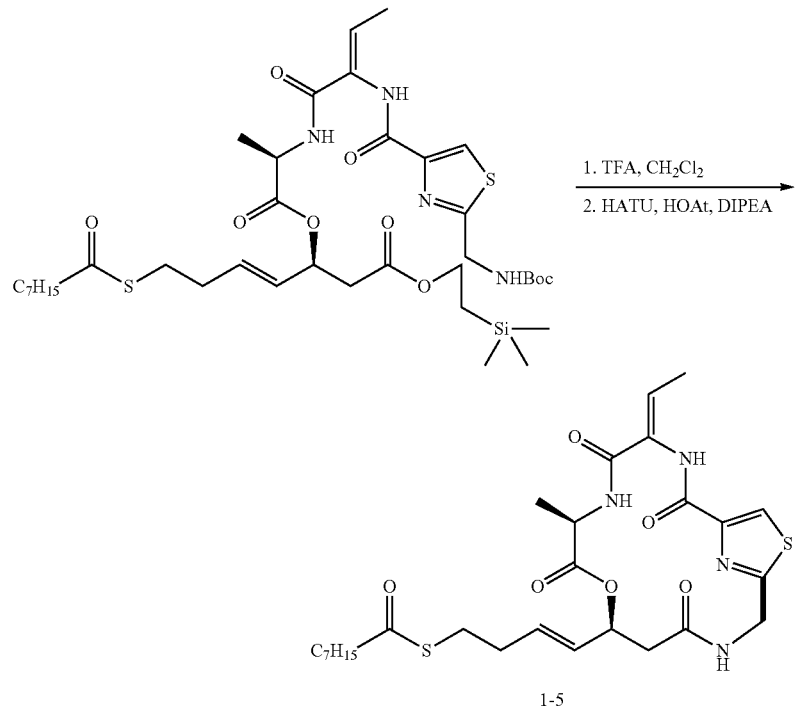

1-5

1 mL of trifluoroacetic acid is added into the solution of raw material (0.184 g, 0.32 mmol) in anhydrous dichloromethane (5 mL) prepared in Embodiment 36 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 40 mL of anhydrous DMF under argon. The mixture is slowly and dropwise added into the solution of HATU (0.437 g, 1.15 mmol), HOAt (0.157 g, 1.15 mmol) and DIPEA (0.38 mL, 2.3 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.081 g of solid 1-5 with the yield of 61%.

$[\alpha]^{23}D$: 30.8 (c 0.86, $CHCl_3$). $^1H$ NMR (400 MHz, $CDCl_3$): δ 8.64(s, 1H), 8.10(s, 1H), 6.99(m, 1H), 6.47(d, J=8.7 Hz, 1H), 6.33(s, 1H), 5.85(dd, J=7.3 Hz, 15.8 Hz, 1H), 5.75(m, 1H), 5.64(m, 1H), 4.95-4.6(m, 3H), 2.88(m, 2H), 2.64(m, 2H), 2.51(t, J=7.6 Hz, 2H), 2.28(m, 2H), 1.85(d, J=7.4 Hz, 3H), 1.61(m, 2H), 1.34(d, J=6.8 Hz, 3H), 1.26(m, 8H), 0.86(m, 3H) ppm. MS (EI, m/z): 579 ($M^++1$). HRMS (ESI): calcd for $C_{27}H_{38}N_4O_6S_2$ [$MNa^+$] 601.2125, found 601.2127.

Embodiment 68 Synthesis of Compound of Formula 1-6 rated to remove a large amount of trifluoroacetic acid. The crude product is directly used in the next step.

The crude product obtained in the last step is dissolved with 40 mL of anhydrous DMF under argon. The mixture is slowly and dropwise added into the solution of HATU (0.57 g, 1.5 mmol), HOAt (0.204 g, 1.5 mmol) and DIPEA (0.5 mL, 3 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.102 of solid 1-6 with the yield of 55%.

$[\alpha]^{23}D$: 6.9 (c 0.95, $CHCl_3$). $^1H$ NMR (400 MHz, $CDCl_3$): δ 8.49(s, 1H), 8.12(s, 1H), 7.03(m, 1H), 6.75-6.65(m, 2H), 5.8-5.55(m, 3H), 5.11(dd, J=7.6 Hz 17.5 Hz, 1H), 4.57(d, J=10.5 Hz, 1H), 4.45(dd, J=3.9 Hz 17.4 Hz, 1H), 2.85(t, J=7.1

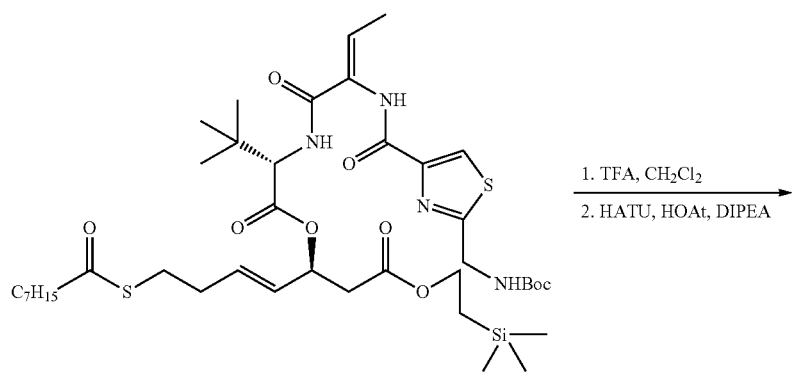

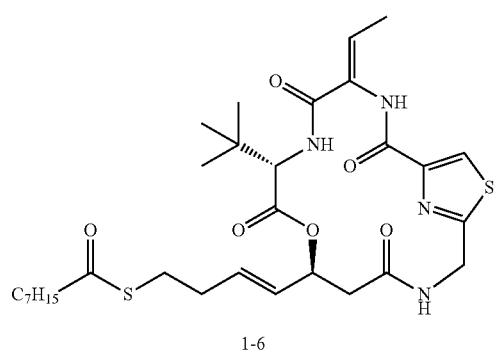

1-6

1 mL of trifluoroacetic acid is added into the solution of raw material (0.252 g, 0.3 mmol) in anhydrous dichloromethane (5 mL) prepared in Embodiment 37 and stirred for 24 h at room temperature. The mixture is evaporated in vacuum. 5 mL of toluene is added into the mixture and evapo- Hz, 2H), 2.67(m, 2H), 2.27(dd, J=6.8 Hz, 13.6 Hz, 2H), 1.87(d, J=7 Hz, 3H), 1.59(m, 2H), 1.23(m, 8H), 0.9-0.77(m, 12H). ppm. MS (EI, m/z): 621 ($M^++1$), 643 ($M^++Na$). HRMS (ESI): calcd for $C_{30}H_{44}N_4O_6S_2$ [$MNa^+$] 643.2595, found 643.2596.

Embodient 69 Synthesis of Compound of Formula 1-7 m

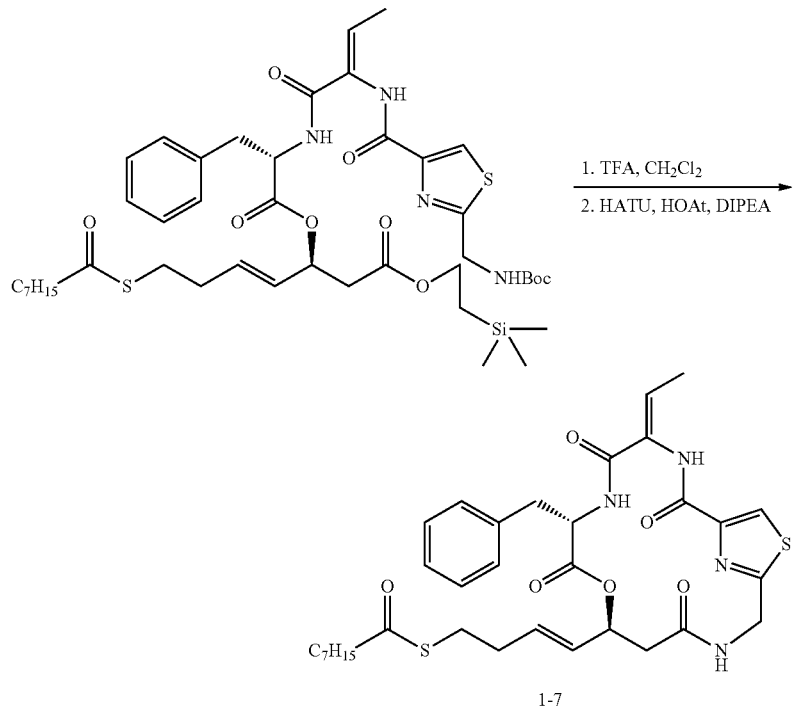

1 mL of trifluoroacetic acid is added into the solution of raw material (0.151 g, 0.173 mmol) in anhydrous dichloromethane (5 mL) prepared in Embodiment 38 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 30 mL of anhydrous DMF under argon. The mixture is slowly and dropwise added into the solution of HATU (0.329 g, 0.865 mmol), HOAt (0.118 g, 0.865 mmol) and DIPEA (0.29 mL, 1.73 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.05 g of solid 1-7 with the yield of 44%.

$[\alpha]^{23}D$: 15.6(c 0.45, $CHCl_3$). $^1H$ NMR (400 MHz, $CDCl_3$): δ 8.24(s, 1H), 8.10(s, 1H), 7.09(m, 1H), 7.05-6.90(m, 5H), 6.44(d, J=10.4 Hz, 1H), 5.75-5.65(m, 2H), 5.78(m, 1H), 5.50 (m, 1H), 5.26(m, 1H), 4.65(dd, J=17.3 Hz, 6 Hz, 1H), 4.53 (dd, J=17.3 Hz 5.3 Hz, 1H), 3.37(dd, J=13.6 Hz 3.4 Hz, 1H), 2.91-2.81(m, 3H), 2.55-2.45(m, 4H), 2.26(q, J=6.8 Hz, 2H), 1.93(d, J=7.2 Hz, 3H), 1.58(m, 2H), 1.25(m, 8H), 0.87(m, 3H). ppm. MS (EI, m/z): 655 ($M^++1$), 677 ($M^++Na$). HRMS (ESI): calcd for $C_{33}H_{42}N_4O_6S_2$ [$MNa^+$] 677.2438, found 677.2437.

Embodiment 70 Synthesis of Compound of Formula 1-9

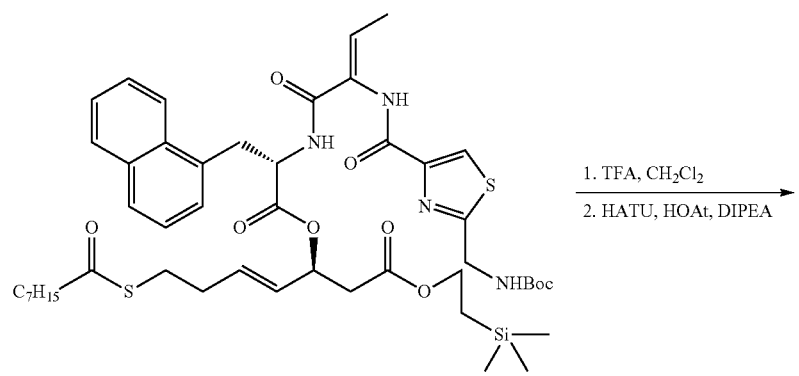

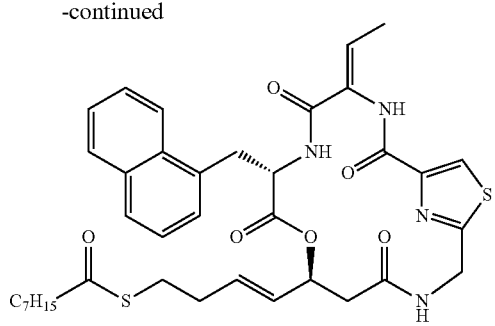

1-9

1 mL of trifluoroacetic acid is added into the solution of raw material (0.24 g, 0.26 mmol) in anhydrous dichloromethane (5 mL) prepared in Embodiment 39 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 40 mL of anhydrous DMF under argon. The mixture is slowly and dropwise added into the solution of HATU (0.494 g, 1.3 mmol), HOAt (0.177 g, 1.3 mmol) and DIPEA (0.43 mL, 2.6 mmol) in anhydrous DMF, and stirred for 3 days at 30° C. The concentration of the reaction liquid system is 0.001 mol/L.

The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.077 g of solid 1-9 with the yield of 42%.

$[\alpha]23D$: −26.5 (c 0.78, CHCl3). 1H NMR (400 MHz, CDCl3): δ 8.03(s, 1H), 7.95(s, 1H), 7.93(s, 1H), 7.64(d, J=8.1 Hz, 1H), 7.53(d, J=7.8 Hz, 1H), 7.41(t, J=7.5 Hz, 1H), 7.32(t, J=7.5 Hz, 1H), 7.14(m, 2H), 7.02(m, 1H), 6.56(d, J=10.1 Hz, 1H), 5.6-5.4(m, 3H), 4.92(m, 1H), 4.61(dd, J=6.6 Hz, 17.2 Hz, 1H), 4.10(m, 1H), 3.75(dd, J=3.5 Hz, 14.2 Hz, 1H), 3.50(dd, J=5.6 Hz, 14.2 Hz, 1H), 2.74(t, J=7.1 Hz, 2H), 2.41(t, J=7.5 Hz, 2H), 2.30(dd, J=5.2 Hz, 15.3 Hz, 1H), 2.14(m, 2H), 1.89(d, J=7.2 Hz, 3H), 1.54(m, 2H), 1.22(m, 8H), 0.84(m, 3H), ppm. MS (EI, m/z): 705 (M++1), 727 (M++Na). HRMS (ESI): calcd for C37H44N4O6S2 [ MNa+] 727.2595, found 727.2596.

Embodiment 71 Synthesis of Compound of Formula 1-8

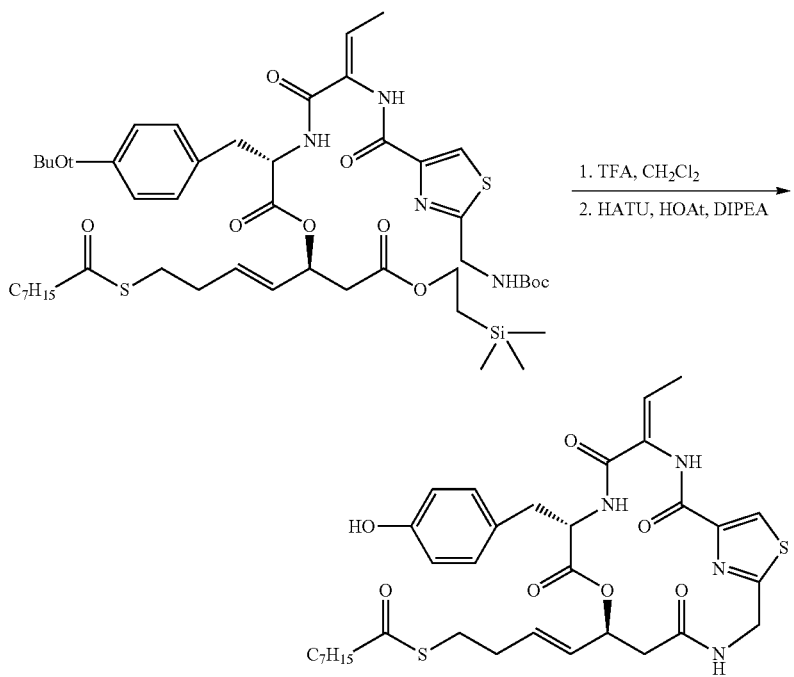

1-8

1 mL of trifluoroacetic acid is added into the solution of raw material (0.165 g, 0.175 mmol) in anhydrous dichloromethane (5 mL) prepared in Embodiment 40 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 40 mL of anhydrous DMF under argon. The mixture is slowly and dropwise added into the solution of HATU (0.333 g, 0.875 mmol), HOAt (0.119 g, 0.875 mmol) and DIPEA (0.3 mL, 1.75 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.075 g of solid 1-8 with the yield of 64%.

$[\alpha]^{23}D$: 7.9 (c 0.65, $CHCl_3$). $^1H$ NMR (400 MHz, MeOD): δ 8.20(s, 1H), 7.67(d, J=9.4 Hz, 1H), 6.83(d, J=8.3 Hz, 2H), 6.72(m, 1H), 6.50(d, J=8.3 Hz, 2H), 5.75-5.65(m, 2H), 5.55 (dd, J=6.7 Hz, 15.6 Hz, 1H), 4.97(d, J=17.4 Hz, 1H), 4.39(d, J=17.4 Hz, 1H), 3.34(s, 1H), 2.99(m, 1H), 2.95-2.83(m, 4H), 2.63(d, J=16.8 Hz, 1H), 2.53(t, J=7.4 Hz, 2H), 2.26(dd, J=6.9 Hz, 13.8 Hz, 2H), 1.79(d, J=7.1 Hz, 3H), 1.62(m, 2H), 1.29 (m, 8H), 0.89(t, J=6.2 Hz, 3H) ppm. MS (EI, m/z): 671 ($M^+$+1), 693 ($M^+$+Na). HRMS (ESI): calcd for $C_{33}H_{42}N_4O_7S_2$ [$MNa^+$] 693.2387, found 693.2386.

Embodiment 72 Synthesis of Compound of Formula 1-1

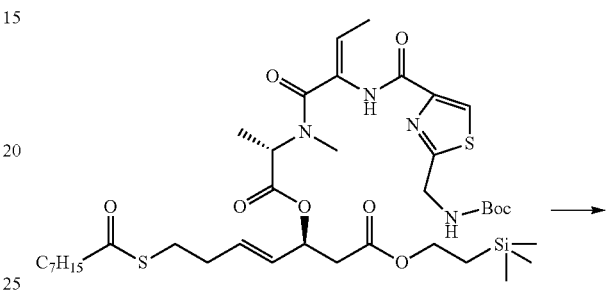

155 mg of raw material (0.198 mmol, 1 eq) prepared in Embodiment 41 is dissolved into anhydrous dichloromethane. 1 mL of trifluoroacetic acid is added into the mixture and stirred for 24 h at room temperature. After the mixture is evaporated in vacuum to remove the solvent and TFA, the mixture with 100 mL of anhydrous DMF is slowly and dropwise added into the solution of 150 mg of HATU (0.396 mmol, 2 eq), 54 mg of HOAT (0.396 mmol, 2 eq) and 0.2 mL of DIPEA (1.188 mmol, 6 eq) in DMF (100 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 22 mg of white solid 1-1 with the yield of 20%.

$[\alpha]_D^{20}$=138.3 1H-NMR (400 MHz, $CDCl_3$) δ 8.70(s, 1-H), 8.10(s, 1-H), 7.11(s, 1-H), 6.92(q, 1-H), 6.84(d, 1-H), 6.61(t, 1-H), 5.73(t, 1-H), 5.68(dd, 1-H), 5.50(dd, 1-H), 5.15(dd, 1-H), 4.68(q, 1-H), 4.35(dd, 1-H), 3.65(d, 1-H), 2.82(t, 2-H), 2.70(dd, 1-H), 2.58(dd, 1-H), 2.55(t, 2-H), 2.22(q, 2-H), 1.95 (s, 3-H), 1.83(d, 3-H), 1.57(t, 2-H), 1.28(m, 8-H), 0.87(t, 3-H); MS (ESI) m/z 564.72 (100%) $(M+H)^+$.

Embodiment 73 Synthesis of Compound of Formula 5-1

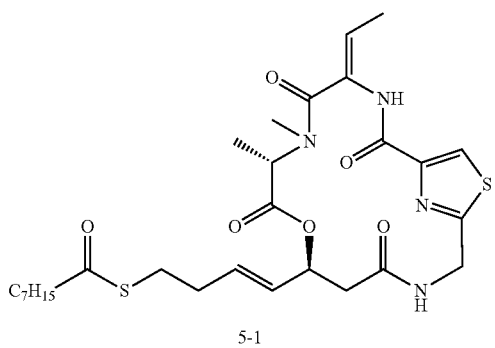

110 mg of raw material (0.136 mmol, 1 eq) prepared in Embodiment 42 is dissolved into 5 mL of anhydrous dichloromethane. 1 mL of trifluoroacetic acid is added into the mixture and stirred for 24 h at room temperature. After the mixture is evaporated in vacuum to remove the solvent and TFA, the mixture with 70 mL of anhydrous DMF is slowly and dropwise added into the solution of 207 mg of HATU (0.544 mmol, 2 eq), 74 mg of HOAT (0.544 mmol, 4 eq) and 0.18 mL of DIPEA (1.088 mmol, 8 eq) in DMF (70 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 10 mg of white solid 5-1 with the yield of 18%.

$[\alpha]_D^{20}$=112.3 1H-NMR (400 MHz, $CDCl_3$) δ 8.80(s, 1-H), 8.07(s, 1-H), 7.11(s, 1-H), 6.78(q, 1-H), 6.40(s, 1-H), 5.80(m, 2-H), 5.45(dd, 1-H), 5.11(s, 1-H), 4.70(brs, 1-H), 4.3(m, 1-H), 3.65(d, 1-H), 2.82(t, 2-H), 2.70(dd, 1-H), 2.58(dd, 1-H), 2.55(t, 2-H), 2.22(q, 2-H), 1.95(s, 3-H), 1.83(d, 3-H), 1.57(t, 2-H), 1.28(m, 8-H), 0.87(t, 3-H); MS (ESI) m/z 564.72 (100%) $(M+H)^+$.

Embodiment 74 Synthesis of Compound of Formula 1-2

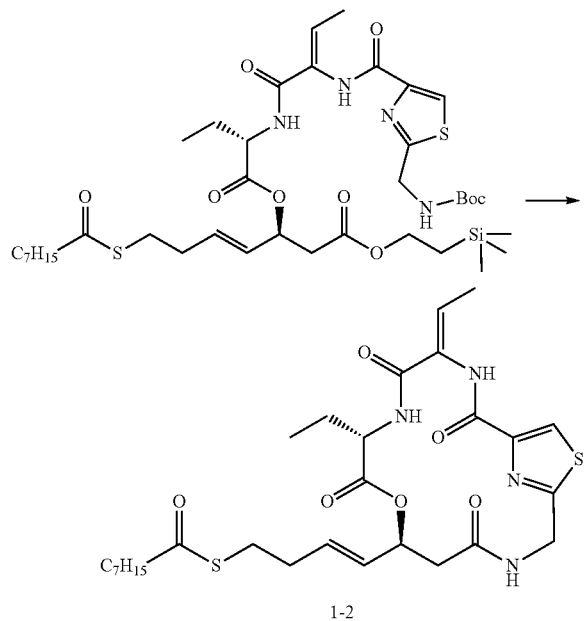

120 mg of raw material (0.148 mmol, 1 eq) prepared in Embodiment 43 is dissolved into 5 mL of anhydrous dichloromethane. 1 mL of trifluoroacetic acid is added into the mixture and stirred for 24 h at room temperature. After the mixture is evaporated in vacuum to remove the solvent and TFA, the mixture with 75 mL of anhydrous DMF is slowly and dropwise added into the solution of 225 mg of HATU (0.592 mmol, 4 eq), 80 mg of HOAT (0.592 mmol, 4 eq) and 0.2 mL of DIPEA (1.184 mmol, 8 eq) in DMF (75 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 40 mg of white solid 1-2 with the yield of 45.6%.

$[\alpha]_D^{20}$=387.3 1H-NMR (400 MHz, CDCl$_3$) δ 8.64(s, 1-H), 8.11(s, 1-H), 6.93(q, 1-H), 6.74(d, 1-H), 6.54(brs, 1-H), 5.76 (m, 2-H), 5.49(dd, 1-H), 5.16(dd, 1-H), 4.76(q, 1-H), 4.37(dd, 1-H), 2.88(t, 2-H), 2.70(dd, 1-H), 2.60(dd, 1-H), 2.50(t, 2-H), 2.28(q, 2-H), 1.95(m, 1-H), 1.83(m, 6-H), 1.67(m, 3-H), 1.28 (m, 8-H), 0.87(t, 3-H), 0.84(t, 3-H); MS (ESI) m/z 593.2 (100%) (M+H)$^+$.

Embodiment 75 Synthesis of Compound of Formula 1-10

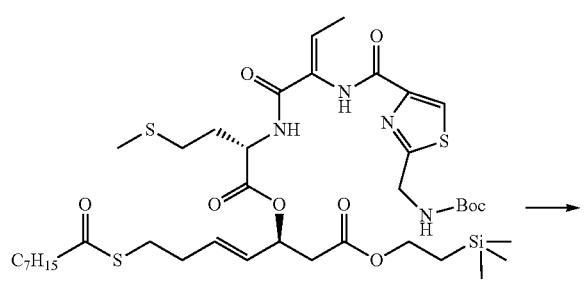

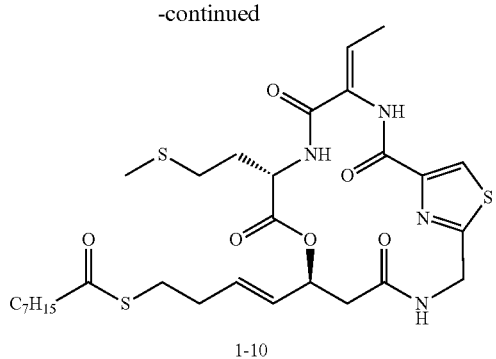

180 mg of raw material (0.21 mmol, 1 eq) prepared in Embodiment 44 is dissolved into 5 mL of anhydrous dichloromethane. 1 mL of trifluoroacetic acid is added into the mixture and stirred for 24 h at room temperature. After the mixture is evaporated in vacuum to remove the solvent and TFA, the mixture with 105 mL of anhydrous DMF is slowly and dropwise added into the solution of 320 mg of HATU (0.84 mmol, 4 eq), 115 mg of HOAT (0.84 mmol, 4 eq) and 0.28 mL of DIPEA (1.68 mmol, 8 eq) in DMF (105 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 28 mg of white solid 1-10 with the yield of 20.9%.

$[\alpha]_D^{20}$=106.8 1H-NMR (400 MHz, CDCl$_3$) δ 8.65(s, 1-H), 8.10(s, 1-H), 7.17(d, 1-H), 6.97(q, 1-H), 6.42(brs, 1-H), 5.76 (m, 2-H), 5.49(dd, 1-H), 5.13(dd, 1-H), 4.72(q, 1-H), 4.37(dd, 1-H), 3.72(s, 1-H), 2.88(t, 2-H), 2.70(dd, 1-H), 2.60(dd, 1-H), 2.50(m, 5-H), 2.28(q, 2-H), 2.17(m, 1-H), 2.12(m, 2-H), 1.95 (s, 3-H), 1.83(m, 3-H), 1.67(m, 3-H), 1.28(m, 8-H), 0.87(t, 6-H); MS (ESI) m/z 593.2 (100%) (M+H)$^+$.

Embodiment 76 Synthesis of Compound of Formula 1-11

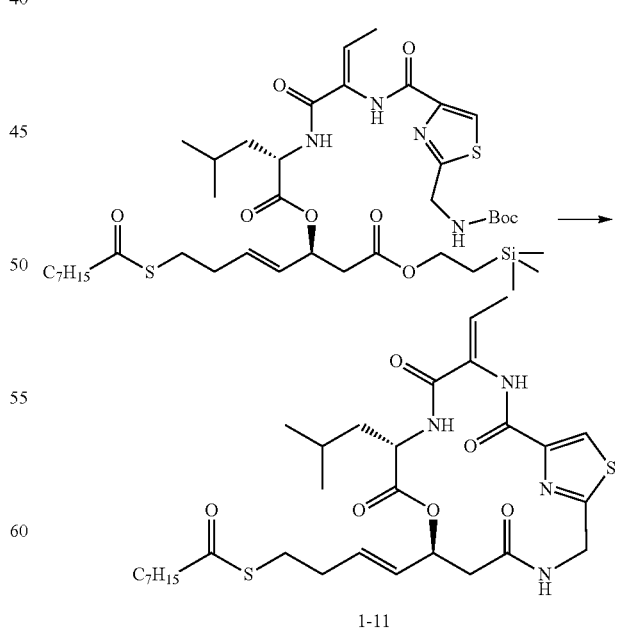

190 mg of raw material (0.226 mmol, 1 eq) prepared in Embodiment 45 is dissolved into 5 mL of anhydrous dichloromethane. 1 mL of trifluoroacetic acid is added into the mixture and stirred for 24 h at room temperature. After the mixture is evaporated in vacuum to remove the solvent and TFA, the mixture with 115 mL of anhydrous DMF is slowly and dropwise added into the solution of 344 mg of HATU (0.904 mmol, 4 eq), 123 mg of HOAT (0.904 mmol, 4 eq) and 0.32 mL of DIPEA (1.808 mmol, 8 eq) in DMF (115 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 43 mg of white solid 1-11 with the yield of 35.6%.

$[\alpha]_D^{20}$=115.5 1H-NMR (400 MHz, CDCl$_3$) δ 8.65(s, 1-H), 8.12(s, 1-H), 6.93(q, 1-H), 6.50(d, 2-H), 6.42(brs, 1-H), 5.76 (m, 2-H), 5.49(dd, 1-H), 5.13(dd, 1-H), 4.72(q, 1-H), 4.37(dd, 1-H), 2.88(t, 2-H), 2.75(m, 2-H), 2.50(m, 2-H), 2.28(q, 2-H), 1.95(d, 3-H), 1.83(m, 3-H), 1.67(m, 3-H), 1.50(m, 3-H), 1.28 (m, 8-H), 0.90(m, 6-H). MS (ESI) m/z 621.2 (100%) (M+H)$^+$.

Embodiment 77 Synthesis of Compound of Formula 5-2

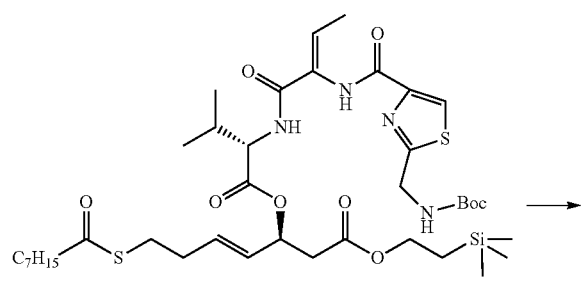

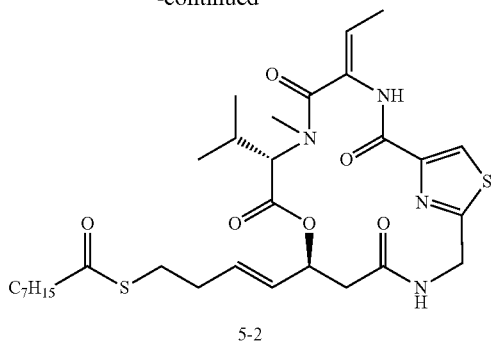

5-2

56 mg of raw material (0.068 mmol, 1 eq) prepared in Embodiment 46 is dissolved into 5 mL of anhydrous dichloromethane. 1 mL of trifluoroacetic acid is added into the mixture and stirred for 24 h at room temperature. After the mixture is evaporated in vacuum to remove the solvent and TFA, the mixture with 115 mL of anhydrous DMF is slowly and dropwise added into the solution of 103 mg of 103 mg of HATU (0.072 mmol, 4 eq), 37 mg of HOAT (0.072 mmol, 4 eq) and 0.1 mL of DIPEA (0.544 mmol, 8 eq) in DMF (115 mL). The mixture reacts for 72 h at normal temperature, and is evaporated in vacuum to remove DMF, diluted with ethyl acetate (20 mL), washed with saturated NaCl (20 mL×2), dried with anhydrous sodium sulfate, evaporated in vacuum, and purified by column chromatography (ethyl acetate) to obtain 4 mg of white solid 5-2 with the yield of 10%.

$[\alpha]_D^{20}$=201.7 1H-NMR (400 MHz, CDCl$_3$) δ 8.74(s, 1-H), 8.01(s, 1-H), 6.26(m, 2-H), 6.00(t, 1-H), 5.80(dd, 1-H), 5.74 (dd, 1-H), 5.06(dd, 1-H), 4.76(d, 1-H), 4.30(dd, 1-H), 2.88(t, 2-H), 2.75(m, 2-H), 2.50(m, 2-H), 2.28(q, 2-H), 1.95(d, 3-H), 1.83(m, 3-H), 1.67(m, 3-H), 1.50(m, 3-H), 1.28(m, 8-H), 0.90(m, 6-H). MS (ESI) m/z 621.2 (100%) (M+H)$^+$.

Embodiment 78 Synthesis of Compound of Formula 2-1

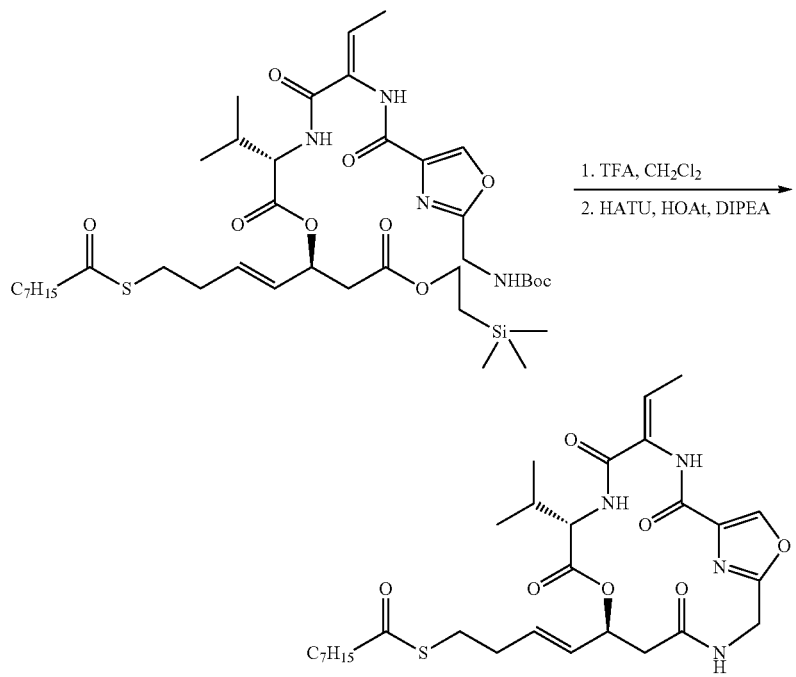

2-1

1 mL of trifluoroacetic acid is added into the solution of raw material (0.331 g, 0.41 mmol) in anhydrous dichloromethane (5 mL) prepared in Embodiment 47 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.78 g, 2.05 mmol), HOAt (0.28 g, 2.05 mmol) and DIPEA (0.7 mL, 4.1 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.102 g of solid 2-1 with the yield of 42%.

$[\alpha]^{23}D$: 35.6 (c 0.9, $CHCl_3$). $^1H$ NMR (400 MHz, $CDCl_3$): δ 8.54(s, 1H), 8.08(s, 1H), 6.94(q, 1H), 6.82(m, 1H), 6.51(d, 1H), 5.74-5.6(m, 2H), 5.47(dd, 1H), 5.14(dd, 1H), 4.70(dd, 1H) 4.32(dd, 1H), 2.82(t, 2H), 2.75-2.59(m, 2H), 2.47(t, 2H), 2.24(m, 2H), 1.82(d, 3H), 1.58(m, 2H), 1.24(m, 8H), 0.83(m, 3H), 0.74(d, 3H), 0.55(d, 3H) ppm. MS (ESI) m/z 591 (100%) $(M+H)^+$ Embodiment 79 Synthesis of Compound of Formula 2-2

1 mL of trifluoroacetic acid is added into the solution of raw material (0.412 g, 0.5 mmol) in anhydrous dichloromethane (5 mL) prepared in Embodiment 48 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.121 g of solid 2-2 with the yield of 40%.

$[\alpha]^{23}D$: 14.3 (c 0.5, $CHCl_3$). $^1H$ NMR (400 MHz, $CDCl_3$): δ 6.82(m, 1H), 6.51(d, 1H), 5.74-5.6(m, 2H), 5.45(dd, 1H), 4.84(dd, 1H) 4.40(d, 1H), 3.8(m, 1H), 3.1(t, 2H), 2.75-2.59 (m, 5H), 2.47(t, 2H), 2.24(m, 2H), 1.82(d, 3H), 1.58(m, 2H), 1.24(m, 8H), 0.83(m, 3H), 0.74(d, 3H), 0.55(d, 3H) ppm. MS (ESI) m/z 606 (M+H)+

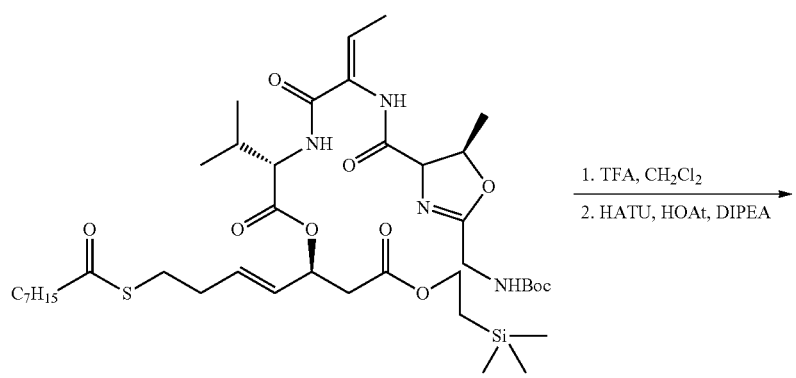

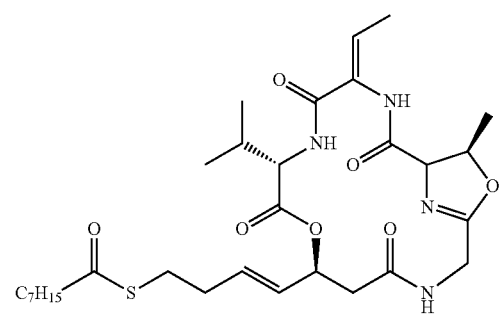

2-2

Embodiment 80 Synthesis of Compound of Formula 2-3

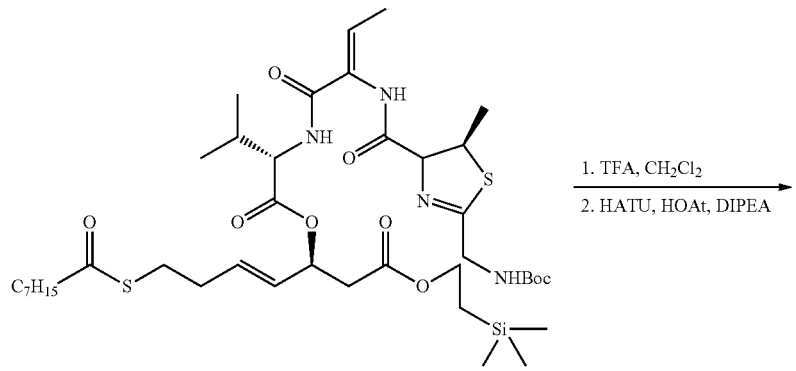

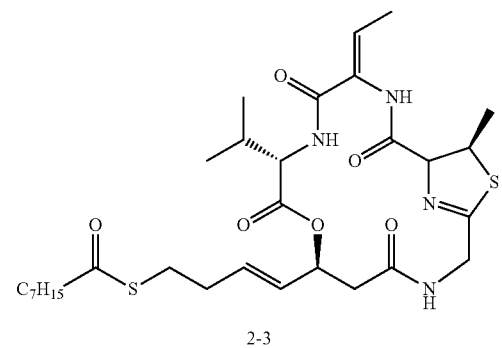

2-3

1 mL of trifluoroacetic acid is added into the solution of raw material (0.504 g, 0.6 mmol) in anhydrous dichloromethane (5 mL) prepared in Embodiment 49 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.706 g, 3 mmol), HOAt (0.408 g, 3 mmol) and DIPEA (1.05 mL, 6 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.131 g of solid 2-3 with the yield of 35%.

$[\alpha]^{23}D$: 29.1 (c 0.9, $CHCl_3$). $^1H$ NMR (400 MHz, $CDCl_3$): δ 6.82(m, 1H), 5.74-5.6(m, 2H), 5.47(dd, 1H), 4.79(dd, 1H), 4.31(dd, 1H), 2.99(t, 2H), 2.75-2.59(m, 3H), 2.47(t, 2H), 2.24(m, 5H), 1.82(d, 3H), 1.58(m, 2H), 1.24(m, 11H), 0.83 (m, 3H), 0.74(d, 3H), 0.55(d, 3H) ppm. MS (ESI) m/z 623 $(M+H)^+$ Embodiment 81 Synthesis of Compound of Formula 2-4

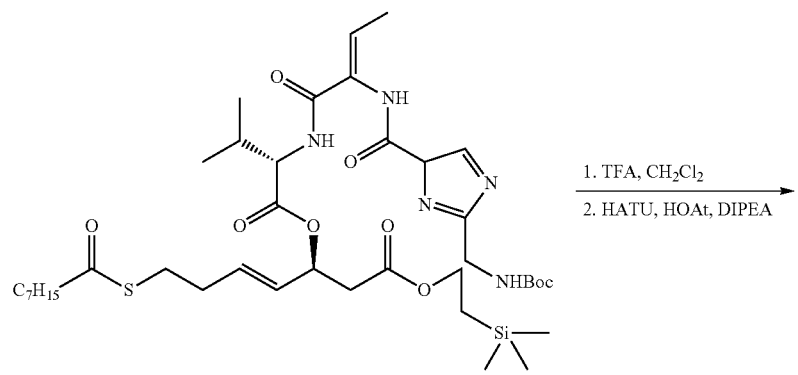

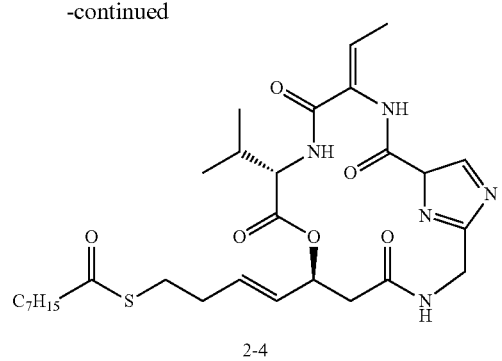

2-4

1 mL of trifluoroacetic acid is added into the solution of raw material (0.404 g, 0.5 mmol) in anhydrous dichloromethane (5 mL) prepared in Embodiment 50 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.091 g of solid 2-4 with the yield of 31%.

$[\alpha]^{23}D$: 34.7(c 0.9, $CHCl_3$). $^1$H NMR (400 MHz, $CDCl_3$): δ 7.6(d, 1H), 5.78-5.6(m, 2H), 5.54(dd, 1H), 5.11(dd, 1H), 4.35(d, 1H), 3.4(dd, 2H), 2.91(t, 2H), 2.47(m, 2H), 2.24(m, 2H), 1.82(d, J=7 Hz, 3H), 1.58(m, 2H), 1.24(m, 8H), 0.83(m, 3H), 0.74(d, 3H), 0.55(d, 3H) ppm. MS (ESI) m/z 590(M+H)$^+$ Embodiment 82 Synthesis of Compound of Formula 2-5

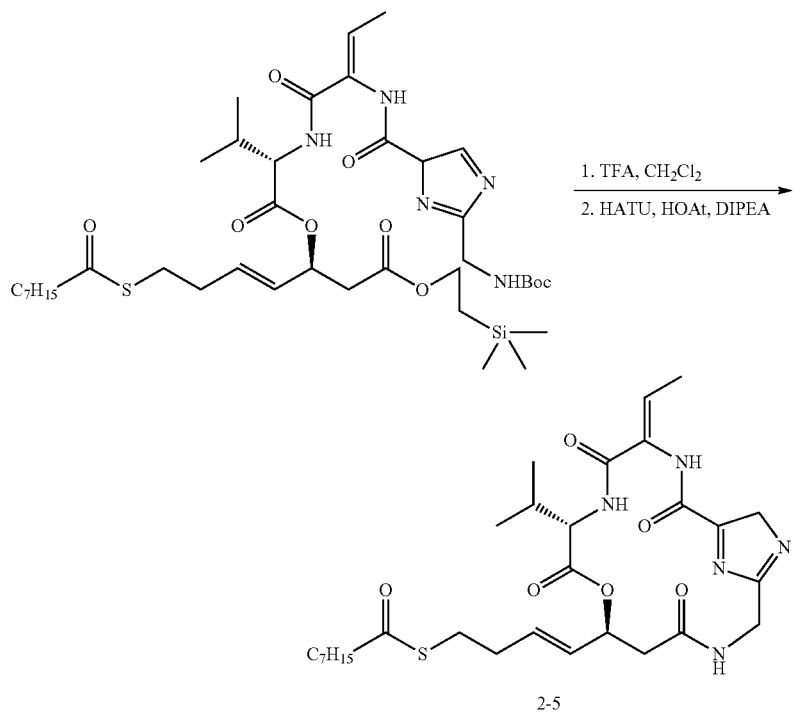

2-5

1 mL of trifluoroacetic acid is added into the solution of raw material (0.404 g, 0.5 mmol) in anhydrous dichloromethane (5 mL) prepared in Embodiment 51 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.103 g of solid 2-5 with the yield of 35%.

$[\alpha]^{23}D$: 34.7(c 0.9, CHCl$_3$). $^1$H NMR (400 MHz, CDCl$_3$): 5.76-5.6(m, 2H), 5.51(dd, 1H), 4.87(dd, 1H), 4.41(d, 1H), 3.4(d, 2H), 2.91(t, 2H), 2.47(m, 2H), 2.24(m, 2H), 1.82(d, J=7 Hz, 3H), 1.58(m, 2H), 1.4(s, 1H), 1.24(m, 8H), 0.83(m, 3H), 0.74(d, 3H), 0.55(d, 3H) ppm. MS (ESI) m/z 590 (M+H)$^+$ Embodiment 83 Synthesis of Compound of Formula 2-6 and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous Na$_2$SO$_4$, filtered, evaporated in vacuum, and purified by column chromatography (petroleum ether:ethyl acetate:metha-

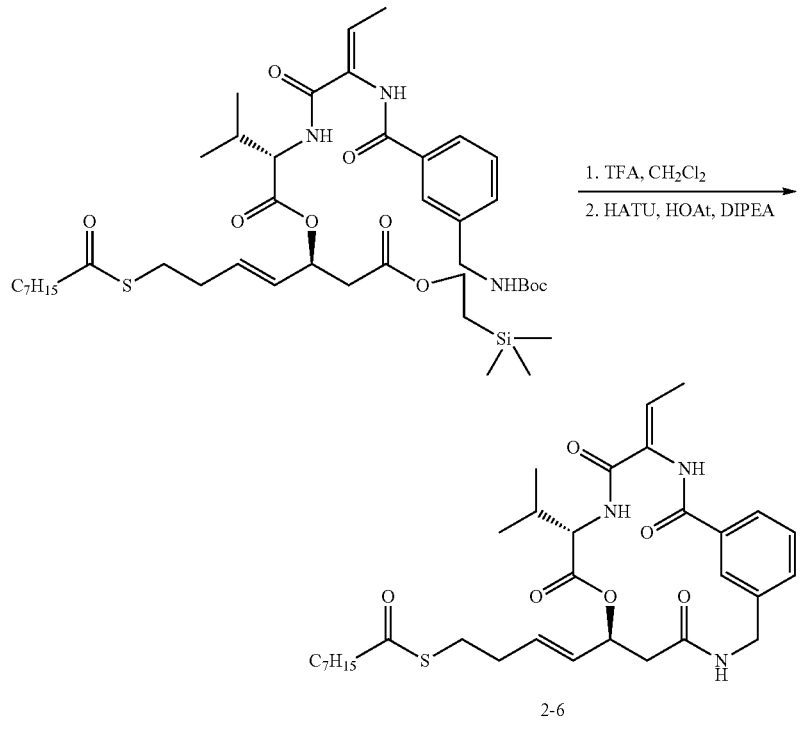

1 mL of trifluoroacetic acid is added into the solution of raw material (0.409 g, 0.5 mmol) in anhydrous dichloromethane (5 mL) prepared in Embodiment 52 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly nol=20:20:1) to obtain 0.165 g of solid 2-6 with the yield of 55%.

$[\alpha]^{23}D$: 34.1(c 0.9, CHCl$_3$). $^1$H NMR (400 MHz, CDCl$_3$): 7.84(d, 1H), 7.74(s, 1H), 7.40(m, 2H), 5.76-5.6(m, 2H), 5.51 (dd, 1H), 4.87(dd, 1H), 4.41(d, 1H), 4.3(d, 2H), 3.4(d, 2H), 2.91(t, 2H), 2.47(m, 2H), 2.24(m, 2H), 1.82(d, 3H), 1.58(m, 2H), 1.4(s, 1H), 1.24(m, 8H), 0.83(m, 3H), 0.74(d, 3H), 0.55 (d, 3H) ppm. MS (ESI) m/z 600 (M+H)$^+$ Embodiment 84 Synthesis of Compound of Formula 2-7

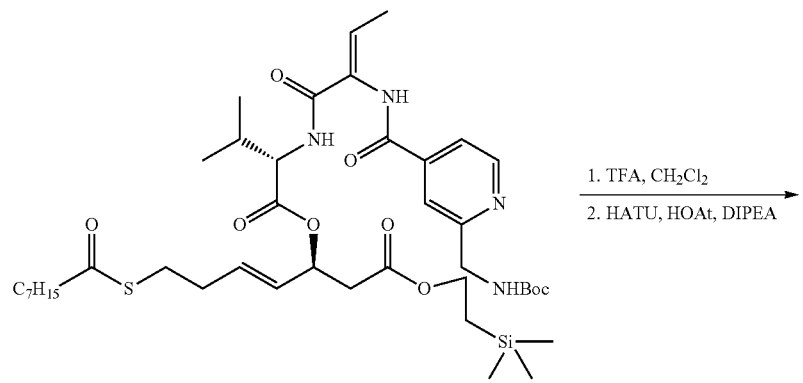

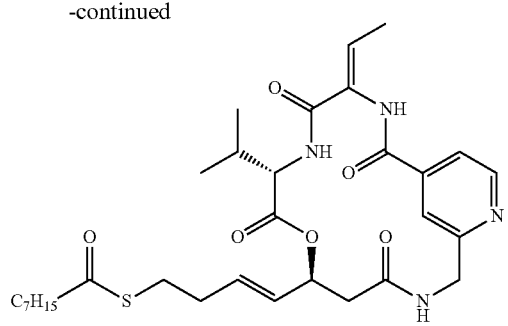

2-7

1 mL of trifluoroacetic acid is added into the solution of raw material (0.410 g, 0.5 mmol) in anhydrous dichloromethane (5 mL) prepared in Embodiment 53 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous Na$_2$SO$_4$, filtered, evaporated in vacuum, and purified by column chromatography (petroleum ether:ethyl acetate:methanol=20:20:1) to obtain 0.183 g of solid 2-7 with the yield of 61%.

$[\alpha]^{23}$D: 21.9(c 0.9, CHCl$_3$). $^1$H NMR (400 MHz, CDCl$_3$): 8.93(d, 1H), 8.16(s, 1H), 7.56(d, 1H), 5.8-5.7(m, 2H), 5.52 (dd, 1H), 4.87(dd, 1H), 4.79(s, 1H), 4.41(d, 1H), 3.4(d, 2H), 2.92(t, 2H), 2.47(m, 4H), 2.08(d, 3H), 1.58(m, 2H), 1.25(m, 8H), 0.83(m, 3H), 0.74(d, 3H), 0.55(d, 3H) ppm. MS (ESI) m/z 601 (M+H)$^+$ Embodiment 85 Synthesis of Compound of Formula 3-2

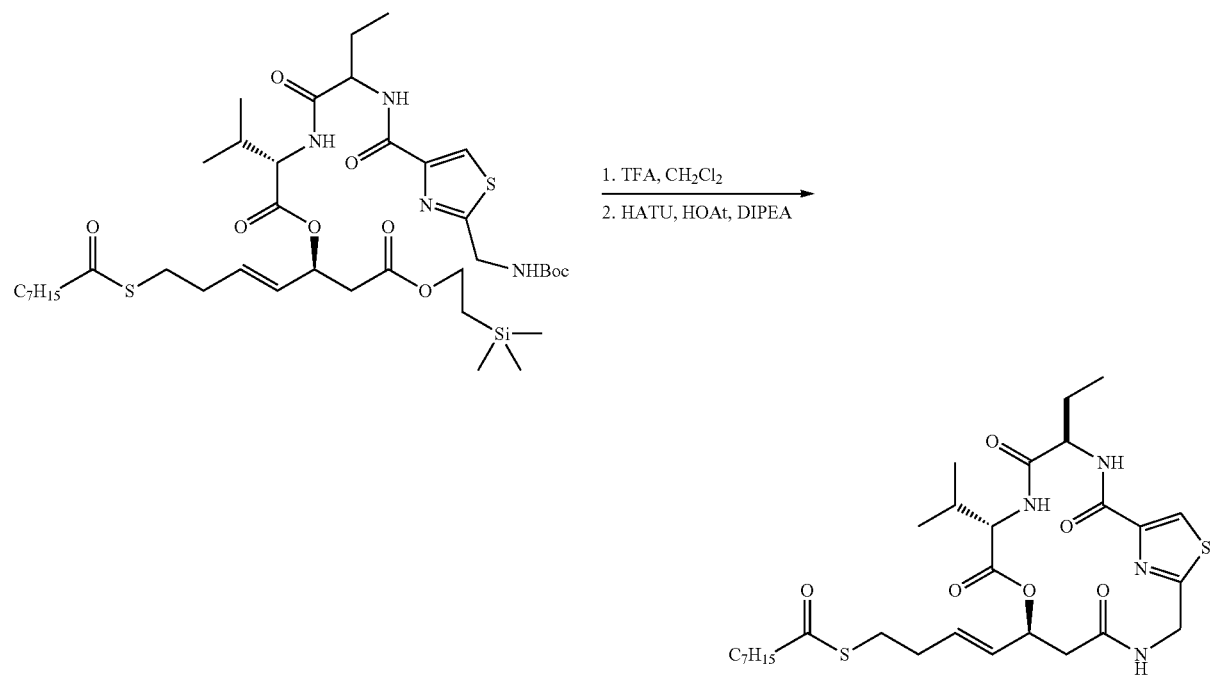

3-2

1 mL of trifluoroacetic acid is added into the solution of raw material (0.413 g, 0.5 mmol) in anhydrous dichloromethane (5 mL) prepared in Embodiment 54 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.128 g of solid 3-2 with the yield of 42%.

$[\alpha]^{23}D$: 28.1 (c 0.9, $CHCl_3$). $^1H$ NMR (400 MHz, $CDCl_3$): δ8.94(s, 1H), 8.08(s, 1H), 6.51(d, 1H), 5.74-5.6(m, 2H), 5.47 (dd, 1H), 4.89(dd, 1H), 4.5-4.35(m, 4H), 2.82(t, 2H), 2.75-2.59(m, 2H), 2.47(t, 2H), 2.24(m, 2H), 1.82(m, 2H), 1.24(m, 8H), 0.92(t, 3H), 0.83(m, 3H), 0.74(d, 3H), 0.55(d, 3H) ppm. MS (EI, m/z): 609 ($M^++1$), 631 ($M^++Na$).

Embodiment 86 Synthesis of Compound of Formula 3-3

1 mL of trifluoroacetic acid is added into the solution of raw material (0.399 g, 0.5 mmol) in anhydrous dichloromethane (5 mL) prepared in Embodiment 55 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.154 g of solid 3-3 with the yield of 53%.

$[\alpha]^{23}D$: 19.1 (c 0.9, $CHCl_3$). $^1H$ NMR (400 MHz, $CDCl_3$): δ8.94(s, 1H), 8.08(s, 1H), 5.74-5.6(m, 2H), 5.47(dd, 1H),

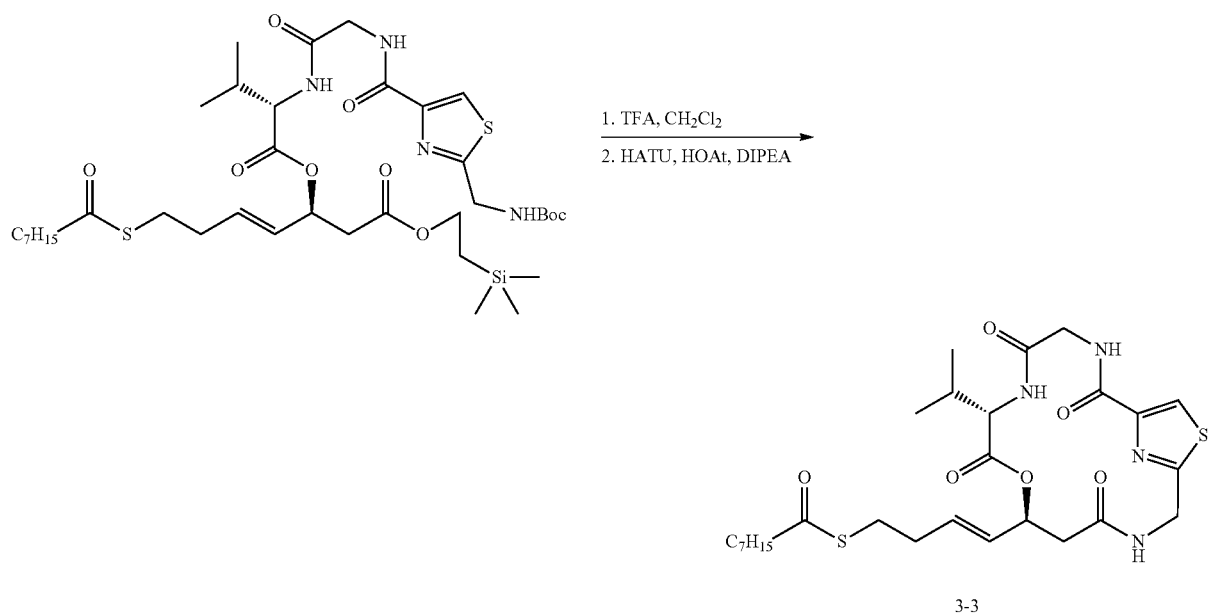

4.89(dd, 1H), 4.5-4.35(m, 4H), 3.85(t, 2H), 2.82(t, 2H), 2.75-2.59(m, 2H), 2.47(t, 2H), 2.24(m, 2H), 1.82(m, 2H), 1.24(m, 8H), 0.92(t, 3H), 0.74(d, 3H), 0.55(d, 3H) ppm. MS (EI, m/z): 581 ($M^++1$), Embodiment 87 Synthesis of Compound of Formula 3-1

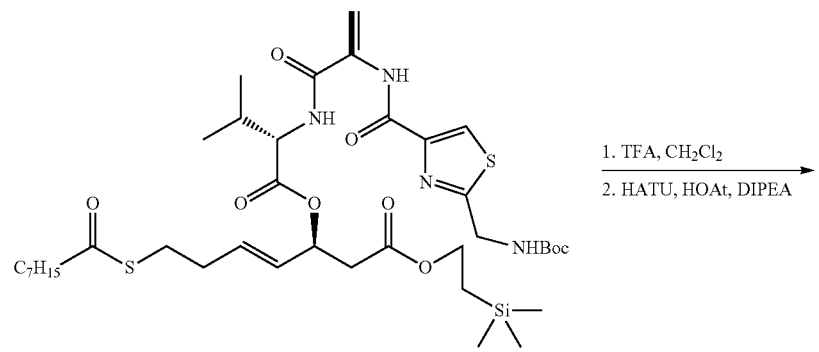

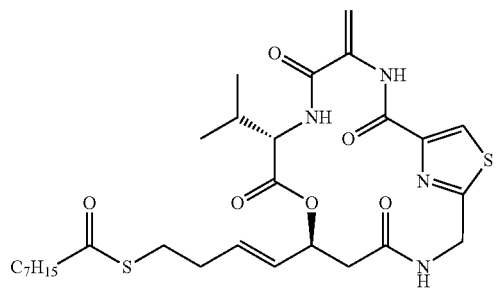

3-1

1 mL of trifluoroacetic acid is added into the solution of raw material (0.405 g, 0.5 mmol) in anhydrous dichloromethane (5 mL) prepared in Embodiment 56 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous Na$_2$SO$_4$, filtered, evaporated in vacuum, and purified by column chromatography (petroleum ether:ethyl acetate:methanol=20:20:1) to obtain 0.136 g of solid 3-1 with the yield of 46%.

[α]$^{23}$D: 14.1 (c 0.9, CHCl$_3$). $^1$H NMR (400 MHz, CDCl$_3$): δ8.94(s, 1H), 8.08(s, 1H), 5.74-5.6(m, 2H), 5.45(d, 1H), 5.13 (d, 1H), 4.89(dd, 1H), 4.5-4.35(m, 3H), 2.82(t, 2H), 2.75-2.59 (m, 2H), 2.47(t, 2H), 2.24(m, 2H), 1.82(m, 2H), 1.24(m, 8H), 0.92(t, 3H), 0.74(d, 3H), 0.55(d, 3H) ppm. MS (EI, m/z): 593 (M$^+$+1), Embodiment 88 Synthesis of Compound of Formula 4-1

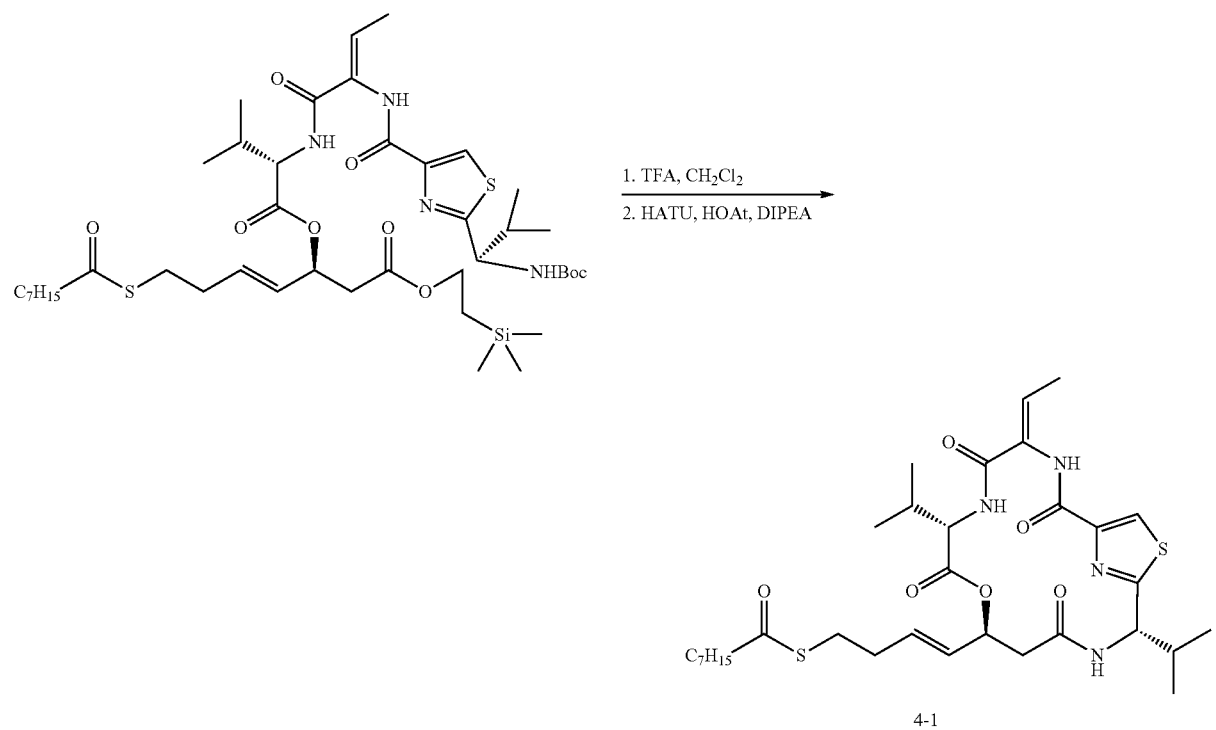

4-1

1 mL of trifluoroacetic acid is added into the solution of raw material (0.433 g, 0.5 mmol) in anhydrous dichloromethane (5 mL) prepared in Embodiment 57 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.085 g of solid 4-1 with the yield of 26%.

$[\alpha]^{23}D$: 6.9 (c 0.9, $CHCl_3$). $^1$H NMR (400 MHz, $CDCl_3$): δ8.95(s, 1H), 5.91(q, 1H), 5.74-5.6(m, 2H), 4.87-4.81(m, 1H), 4.40(d, 1H), 2.82(m, 2H), 2.75-2.59(m, 2H), 2.47(t, 2H), 2.24(m, 2H), 1.82(d, J=7 Hz, 3H), 1.58(m, 2H), 1.24(m, 8H), 0.83(m, 3H), 0.74(d, 6H), 0.55(d, 6H) ppm. MS (EI, m/z): 649 ($M^+$+1)

Embodiment 89 Synthesis of Compound of Formula 4-2 rated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.059 g of solid 4-2 with the yield of 19%.

$[\alpha]^{23}D$: 17.3 (c 0.9, $CHCl_3$). $^1$H NMR (400 MHz, $CDCl_3$): δ8.95(s, 1H), 5.91(q, 1H), 5.74-5.6(m, 2H), 4.87-4.81(m,

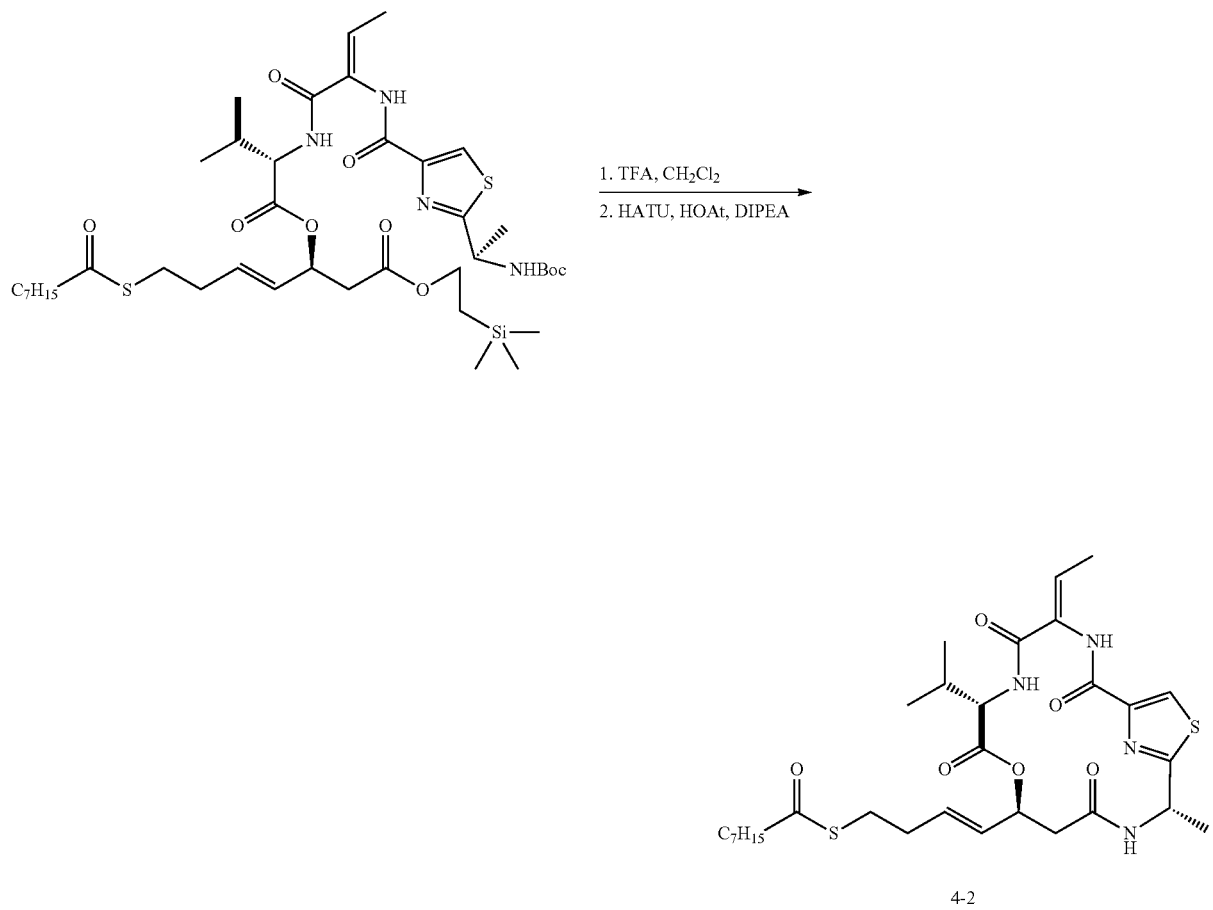

4-2

1 mL of trifluoroacetic acid is added into the solution of raw material (0.419 g, 0.5 mmol) in anhydrous dichloromethane (5 mL) prepared in Embodiment 58 and stirred for 24 h at room temperature. The mixture is evaporated in vacuum. 5 mL of toluene is added into the mixture and evapo- 1H), 4.40(d, 1H), 2.82(m, 2H), 2.75-2.59(m, 2H), 2.47(t, 2H), 2.24(m, 2H), 1.82(d, J=7 Hz, 3H), 1.58(m, 2H), 1.48(d, 3H), 1.24(m, 8H), 0.83(m, 3H), 0.74(d, 3H), 0.55(d, 3H) ppm. MS (EI, m/z): 621 ($M^+$+1)

Embodiment 90 Synthesis of Compound of Formula 4-3

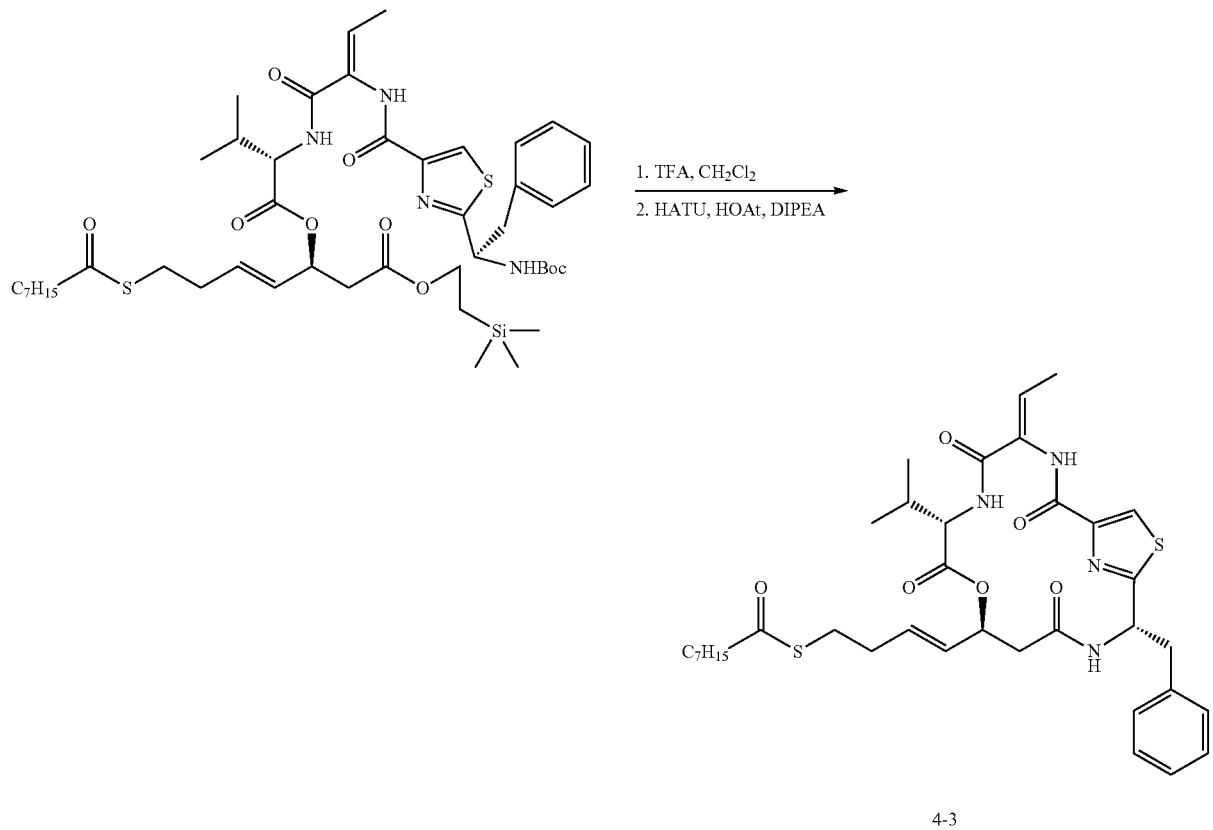

4-3

1 mL of trifluoroacetic acid is added into the solution of raw material (0.457 g, 0.5 mmol) in anhydrous dichloromethane (5 mL) prepared in Embodiment 59 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.059 g of solid 4-3 with the yield of 17%.

$[α]^{23}D$: 48.3 (c 0.9, $CHCl_3$). $^1H$ NMR (400 MHz, $CDCl_3$): δ8.95(s, 1H), 7.41(m, 2H), 7.28(m, 3H), 5.91(q, 1H), 5.74-5.6(m, 2H), 4.87-4.81(m, 1H), 4.40(d, 1H), 2.82(m, 2H), 2.75-2.59(m, 2H), 2.47(t, 2H), 2.24(m, 2H), 1.82(d, J=7 Hz, 3H), 1.58(m, 2H), 1.48(d, 3H), 1.24(m, 8H), 0.83(m, 3H), 0.74(d, 3H), 0.55(d, 3H) ppm. MS (EI, m/z): 697 ($M^++1$)

Embodiment 91 Synthesis of Compound of Formula 4-4

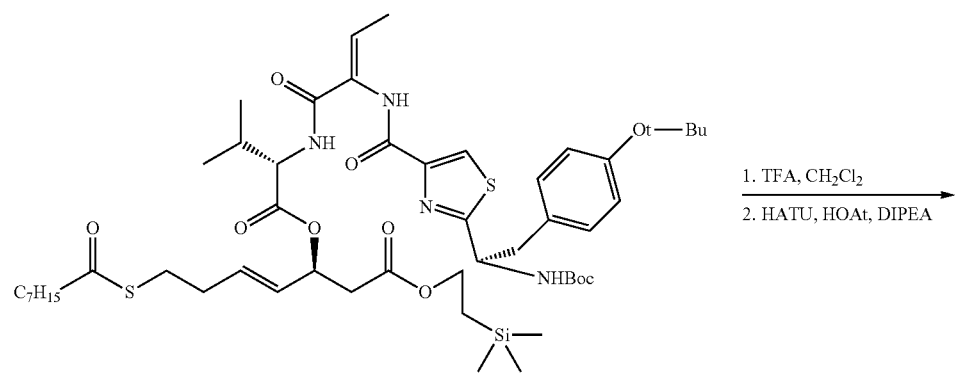

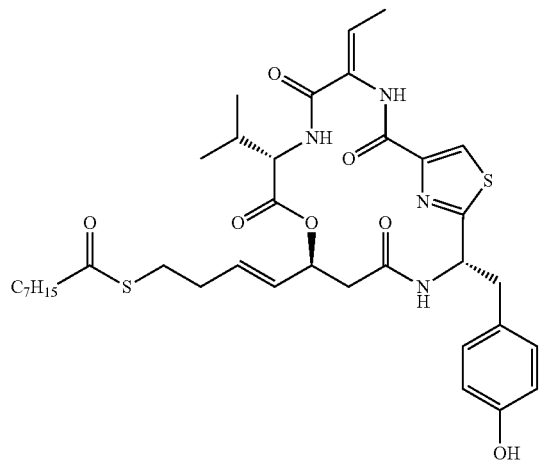

4-4

1 mL of trifluoroacetic acid is added into the solution of raw material (0.493 g, 0.5 mmol) in anhydrous dichloromethane (5 mL) prepared in Embodiment 60 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.039 g of solid 4-4 with the yield of 11%.

$[\alpha]^{23}D$: 5.1 (c 0.9, $CHCl_3$). $^1$H NMR (400 MHz, $CDCl_3$): δ8.95(s, 1H), 7.12(d, 2H), 6.7(d, 2H), 5.91(q, 1H), 5.74-5.6 (m, 2H), 5.3(s, 1H), 4.87-4.81(m, 1H), 4.40(d, 1H), 2.82(m, 2H), 2.75-2.59(m, 2H), 2.47(t, 2H), 2.24(m, 2H), 1.82(d, J=7 Hz, 3H), 1.58(m, 2H), 1.48(d, 3H), 1.24(m, 8H), 0.83(m, 3H), 0.74(d, 3H), 0.55(d, 3H) ppm. MS (EI, m/z): 713 (M$^+$+1)

Embodiment 92 Synthesis of Compound of Formula 6-2

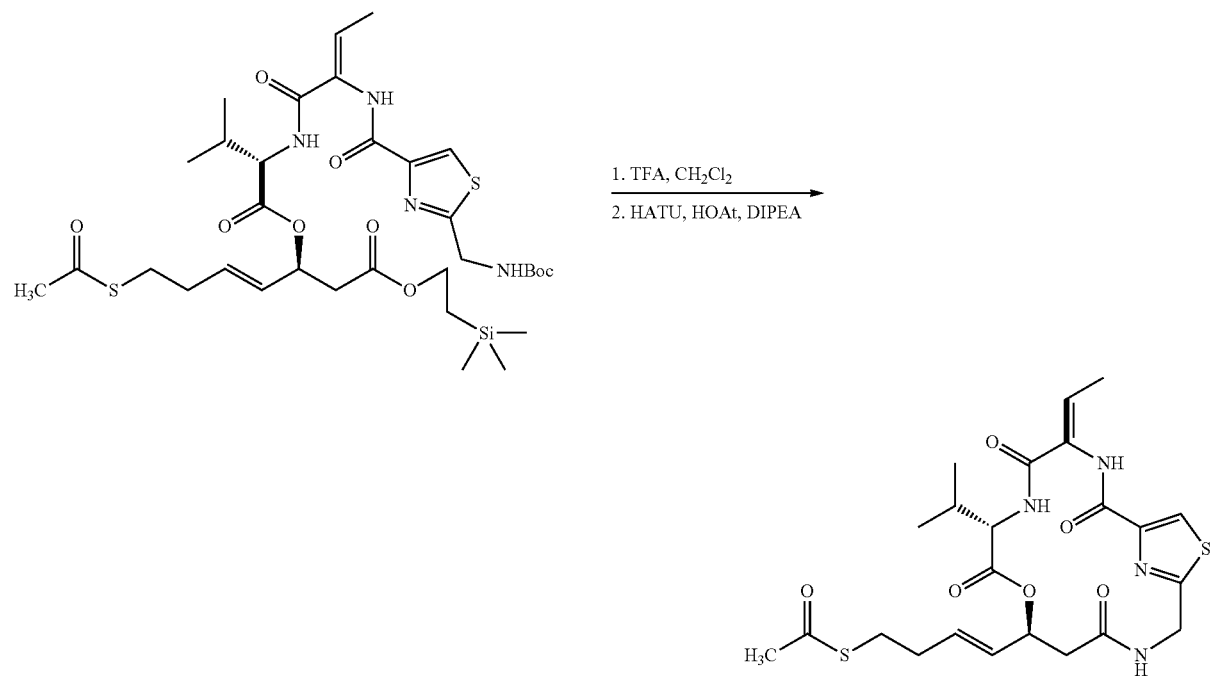

6-2

1 mL of trifluoroacetic acid is added into the solution of raw material (0.370 g, 0.5 mmol) in anhydrous dichloromethane (5 mL) prepared in Embodiment 61 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.125 g of solid 6-2 with the yield of 48%.

$[\alpha]^{23}D$: 28.1 (c 0.9, $CHCl_3$). $^1$H NMR (400 MHz, $CDCl_3$): δ 8.95(s, 1H), 5.91(q, 1H), 5.74-5.6(m, 2H), 4.87-4.81(m, 3H), 4.40(d, 1H), 2.82(m, 2H), 2.75-2.59(m, 2H), 2.47(t, 2H), 2.24(m, 5H), 1.82(d, 3H), 1.58(m, 2H), 1.48(d, 3H), 0.83(m, 3H), 0.74(d, 3H), 0.55(d, 3H) ppm. MS (EI, m/z): 523 ($M^+$+1)

Embodiment 93 Synthesis of Compound of Formula 6-3

1 mL of trifluoroacetic acid is added into the solution of raw material (0.447 g, 0.5 mmol) in anhydrous dichloromethane (5 mL) prepared in Embodiment 62 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.142 g of solid 6-3 with the yield of 42%.

$[\alpha]^{23}D$: 28.1 (c 0.9, $CHCl_3$). $^1$H NMR (400 MHz, $CDCl_3$): δ 8.95(s, 1H), 5.91(q, 1H), 5.74-5.6(m, 2H), 4.87-4.81(m, 3H), 4.40(d, 1H), 2.82(m, 2H), 2.75-2.59(m, 2H), 2.47(t, 2H), 2.24(m, 2H), 1.82(d, 3H), 1.58(m, 2H), 1.48(d, 3H), 0.83(m, 20H), 0.74(d, 3H), 0.55(d, 3H) ppm. MS (EI, m/z): 677 ($M^+$+1)

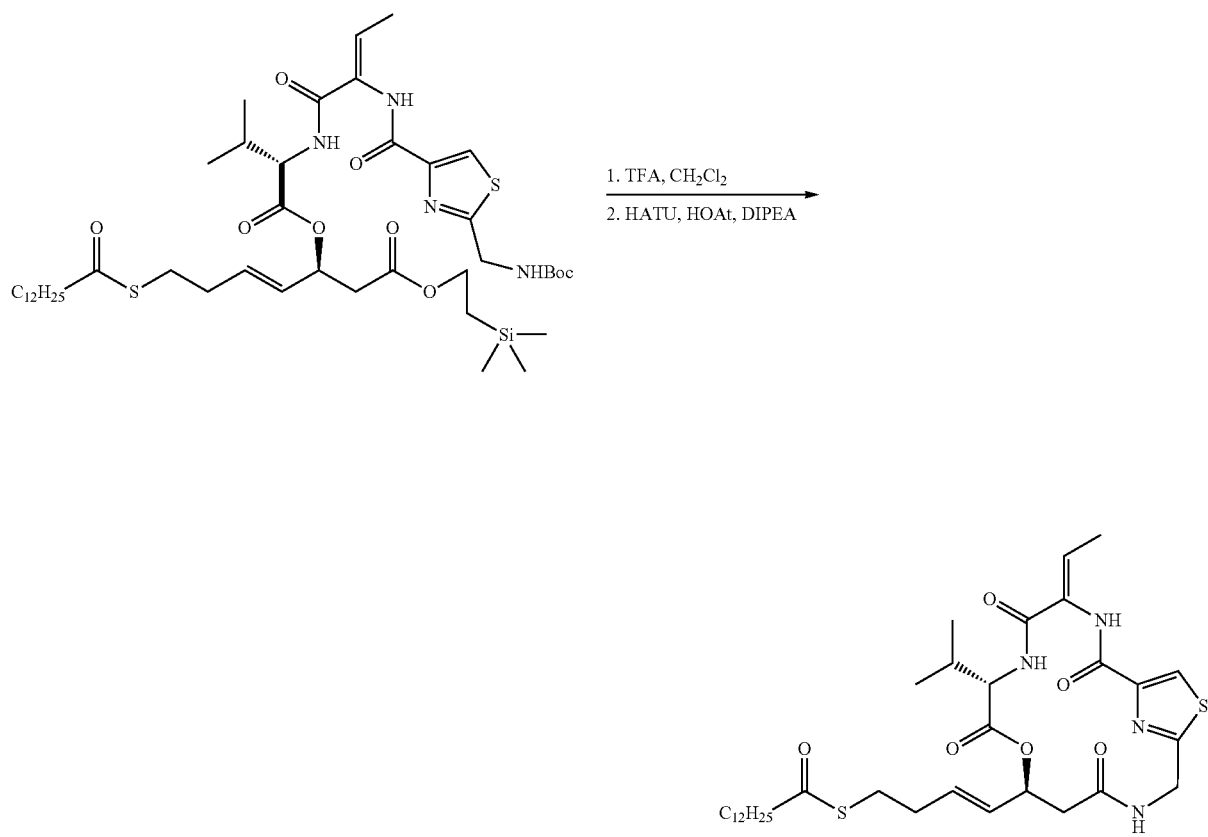

6-3

Embodiment 94 Synthesis of Compound of Formula 6-4

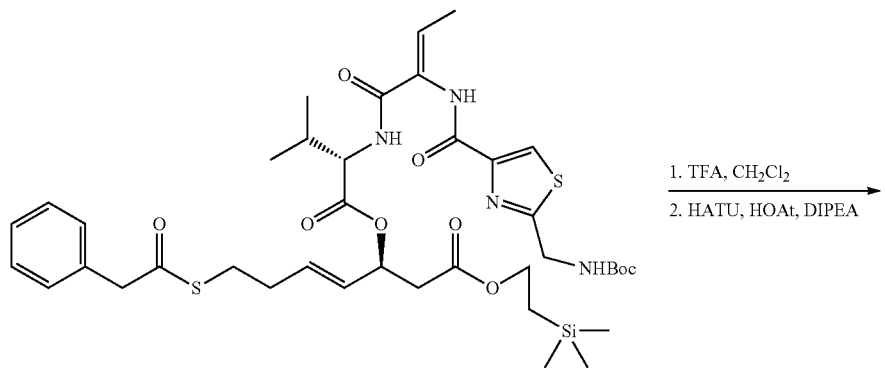

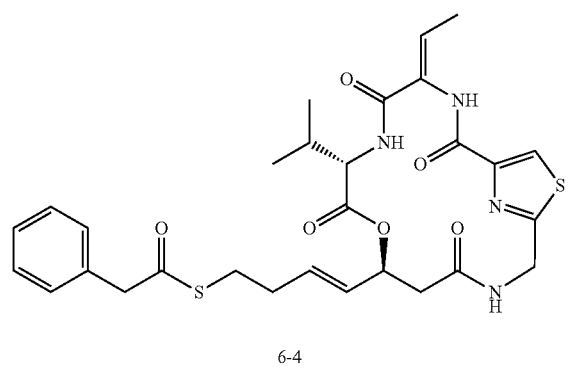

6-4

1 mL of trifluoroacetic acid is added into the solution of raw material (0.408 g, 0.5 mmol) in anhydrous dichloromethane (5 mL) prepared in Embodiment 63 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.588 g, 2.5 mmol), HOAt (0.34 g, 2.5 mmol) and DIPEA (0.87 mL, 5 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.132 g of solid 6-4 with the yield of 42%.

$[\alpha]^{23}D$: 32.8 (c 0.9, $CHCl_3$). $^1H$ NMR (400 MHz, $CDCl_3$): δ 8.95(s, 1H), 7.33(m, 2H), 7.23(m, 3H), 5.91(q, 1H), 5.74-5.6(m, 2H), 4.87-4.81(m, 3H), 4.40(d, 1H), 3.66(s, 2H), 2.82 (m, 2H), 2.75-2.59(m, 2H), 2.47(t, 2H), 2.24(m, 2H), 1.82(d, 3H), 1.58(m, 2H), 1.48(d, 3H), 0.74(d, 6H), ppm. MS (EI, m/z): 599 ($M^+$+1)

Embodiment 95 Synthesis of Compound of Formula 6-5

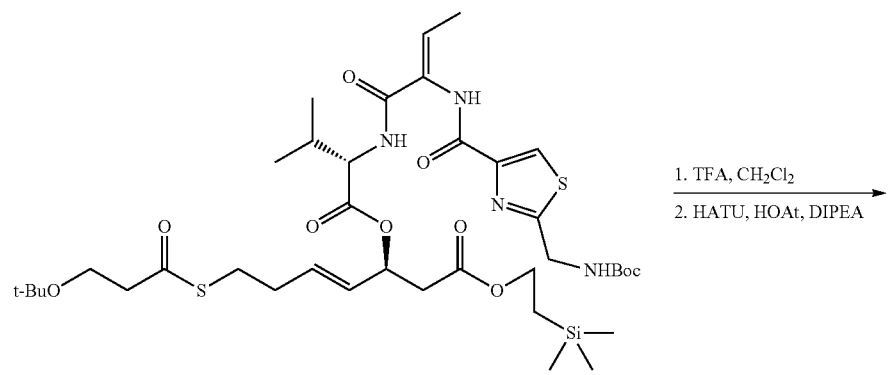

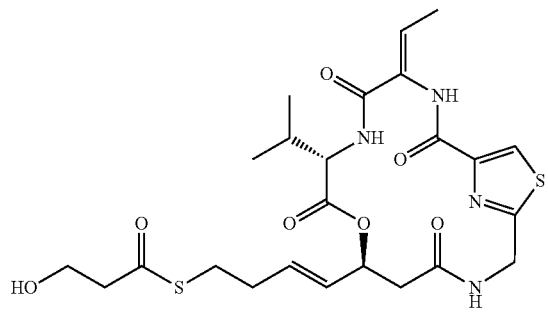

6-5

1 mL of trifluoroacetic acid is added into the solution of raw material (0.339 g, 0.5 mmol) in anhydrous dichloromethane (5 mL) prepared in Embodiment 64 and stirred for 24 h at room temperature. The mixture is evaporated in vacuum. 5 mL of toluene is added into the mixture and evaporated to remove a large amount of trifluoroacetic acid. The crude product is directly used in the next step.

The crude product obtained in the last step is dissolved with 50 mL of anhydrous DMF under argon. The mixture is slowly and dropwise added into the solution of HATU (0.78 g, 2.05 mmol), HOAt (0.28 g, 2.05 mmol) and DIPEA (0.7 mL, 4.1 mmol) in anhydrous DMF, and stirred for 3 days at 30° C. The concentration of the reaction liquid system is 0.001 mol/L. The mixture is evaporated in vacuum to remove DMF, dissolved with ethyl acetate, washed with diluted hydrochloric acid and saturated NaCl in turn, dried with anhydrous $Na_2SO_4$, filtered, evaporated in vacuum, and purified by column chromatography (petroleum ether:ethyl acetate:methanol=20:20:1) to obtain 0.144 g of solid 6-5 with the yield of 52%.

$[\alpha]^{23}D$: 11.3 (c 0.9, $CHCl_3$). $^1$H NMR (400 MHz, $CDCl_3$): δ8.64(s, 1H), 8.08(s, 1H), 6.97(q, J=7 Hz, 1H), 6.82(m, 1H), 6.51(d, J=10.1 Hz, 1H), 5.74-5.6(m, 2H), 5.47(dd, J=15.5 Hz 6.8 Hz, 1H), 5.14(dd, J=16 Hz 8.2 Hz, 1H), 4.70(dd, J=10.1 Hz 3.2 Hz, 1H) 4.32(dd, J=17.4 Hz, 3.5 Hz, 1H), 3.86(m, 1H), 3.65(s, 1H), 2.82(t, J=7.2 Hz, 2H), 2.75-2.59(m, 2H), 2.47(t, J=7.5 Hz, 2H), 2.24(m, 2H), 1.82(d, J=7 Hz, 3H), 1.58(m, 2H), 0.74(d, J=6.7 Hz, 3H), 0.55(d, J=6.7 Hz, 3H) ppm. MS (EI, m/z): 553 ($M^+$+1).

Embodiment 96 Synthesis of Compound of Formula 6-1

6-1

Ammonia (28.9%, 5 mL) is added into the solution of the compound (0.26 g, 0.43 mmol) of Formula 1-3 prepared in Embodiment 65 in acetonitrile (50 mL). The mixture reacts for 12 h at room temperature. At the end of reaction, the mixture is concentrated in vacuum. The residue is directly purified by column chromatography (ethyl acetate:methanol=10:1) to obtain 0.17 g of the compound of Formula 6-1 with the yield of 79%.

$[\alpha]^{23}D$: 25.4 (c 0.6, $CHCl_3$) $^1$H NMR (400 MHz, $CDCl_3$) δ 7.79(s, 1H), 7.18(d, J=9.2 Hz, 1H), 6.64(dd, J=8.8, 3.2 Hz, 1H), 5.89(ddd, J=15.6, 6.8, 6.8 Hz, 1H), 5.69 (dd, J=6.8, 6.8 Hz, 1H), 5.54(dd, J=15.6, 6.8 Hz, 1H), 5.25(dd, J=17.6, 9.2 Hz, 1H), 4.61(dd, J=9.6, 3.6 Hz, 1H), 4.21(dd, J=17.6, 3.2 Hz, 1H), 4.03(d, J=11.2 Hz, 1H), 3.28(d, J=11.2 Hz, 1H), 2.87(dd, J=16.4, 10.0 Hz, 1H), 2.71(dd, J=6.8, 6.8 Hz, 1H), 2.68-2.75 (m, 1H), 2.44(ddd, J=7.2, 7.2, 7.2 Hz, 2H), 2.07-2.13(m, 1H), 1.86(s, 3H), 0.70(d, J=6.8 Hz, 1H), 0.53(d, J=6.8 Hz, 1H); MS (EI, m/z): 481 ($M^+$+1).

Embodiment 97 Synthesis of Compound of Formula 6-6

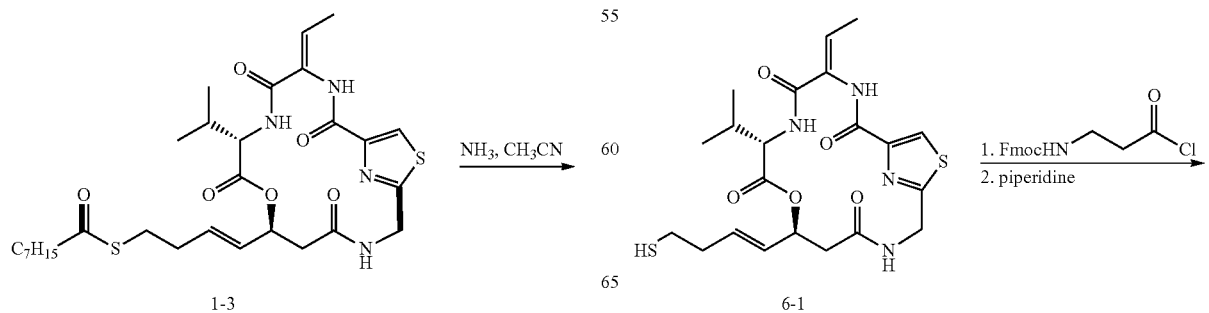

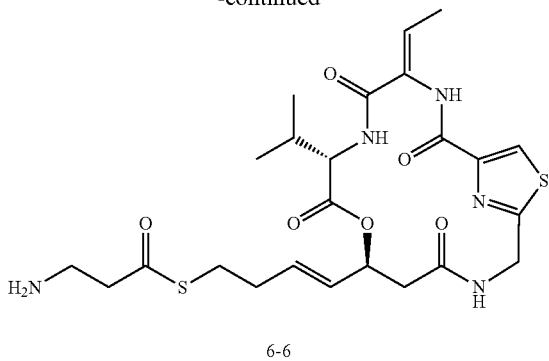

6-6

Triethylamine (1 mL, 4 mmol) and acyl chloride (10 mmol) are added into 200 mL of solution of the compound (0.96 g, 2 mmol) of Formula 6-1 prepared in Embodiment 96 in anhydrous dichloromethane. The mixture reacts for 2 h at room temperature. Piperidine (10 mmol) is added into the mixture for reaction for 1 h. After completely reacted, the mixture is cooled to 0° C., quenched with methanol and purified by column chromatography to obtain 0.88 g of the compound of Formula 6-6 with the yield of 80%.

$[\alpha]^{23}D$: 18.6 (c 0.9, CHCl$_3$). $^1$H NMR (400 MHz, CDCl$_3$): δ 8.69(s, 1H), 8.08(s, 1H), 6.97(q, J=7 Hz, 1H), 6.82(m, 1H), 6.51(d, J=10.1 Hz, 1H), 5.74-5.6(m, 2H), 5.47(dd, J=15.5 Hz 6.8 Hz, 1H), 5.40(dd, J=16 Hz 8.2 Hz, 1H), 4.68(dd, J=10.1 Hz 3.2 Hz, 1H) 4.32(dd, J=17.4 Hz, 3.5 Hz, 1H), 3.86(m, 1H), 3.65(s, 1H), 2.82(t, J=7.2 Hz, 2H), 2.75-2.59(m, 2H), 2.47(t, J=7.5 Hz, 2H), 2.24(m, 2H), 1.82(d, J=7 Hz, 3H), 1.58(m, 2H), 0.74(d, J=6.7 Hz, 3H), 0.55(d, J=6.7 Hz, 3H) ppm. MS (EI, m/z): 552 (M$^+$+1).

Embodiment 98 Measurement of Biochemical Activities of HDAC

1. Measurement principles: the measurement of biochemical activities of compounds is determined according to the degree of the compounds inhibiting the deacylation of HDAC enzyme. After the fluorescently-labeled substrate containing acetylated lysine side chain reacts with the HDAC enzyme, the fluorogenic substrate is deacetylated. After the deacetylated fluorescently-labeled substrate is cracked by the enzyme, a fluorescent substance is released. The fluorescent substance generates emitting light of 460 nm under the excitation of light of 360 nm.

2. Detailed steps: the substrate of HDAC is diluted to 200M (the reaction concentration is 20M) with a reaction buffer. HDAC enzyme is diluted to a proper concentration. The compounds to be detected in different concentrations are added. The mixture reacts for 30 min at 37. Then the developer with the same volume and twice concentration of the substrate is added into the mixture. The mixture is incubated for 15 min at room temperature. Finally, the reading is measured with a micro plate scanner. The excitation light is 360 nm, the emitting light is 460 nm, and the data is processed with Prime 4 software. The commercially available Zolinza (SAHA) is used as a comparison.

3. Detection results and analysis

| sample | IC$_{50}$ (μM) | |
|---|---|---|
| | HDAC1 | HDAC7 |
| SAHA | 0.15 | no activity |
| 1-1 | <0.1 | no activity |
| 1-2 | <0.19 | no activity |
| 1-3 | <10 | no activity |
| 1-4 | <1.0 | no activity |
| 1-5 | <10 | no activity |
| 1-6 | <10 | no activity |
| 1-7 | <10 | no activity |
| 1-8 | <0.102 | no activity |
| 1-9 | <10 | no activity |
| 1-10 | <0.10 | no activity |
| 1-11 | <0.10 | no activity |
| 1-12 | <0.1 | no activity |
| 2-1 | <0.1 | no activity |
| 2-2 | <10 | no activity |
| 2-3 | <10 | no activity |
| 2-4 | <10 | no activity |
| 2-5 | <10 | no activity |
| 2-6 | <10 | no activity |
| 2-7 | <10 | no activity |
| 3-1 | <10 | no activity |
| 3-2 | <10 | no activity |
| 3-3 | <10 | no activity |
| 4-1 | <10 | no activity |
| 4-2 | <0.1 | no activity |
| 4-3 | <10 | no activity |
| 4-4 | <10 | no activity |
| 5-1 | <10 | no activity |
| 5-2 | <10 | no activity |
| 6-1 | <0.1 | no activity |
| 6-2 | <10 | no activity |
| 6-3 | <10 | no activity |
| 6-4 | <10 | no activity |
| 6-5 | <10 | no activity |
| 6-6 | <1.0 | no activity |

IC$_{50}$ in the above table refers to the concentration of inhibitors that are 50% inhibitory (50% inhibitory concentration).

It can be seen from the results in the above table that, in comparison with positive control (SAHA), the above compounds have remarkable activity of inhibiting the deacytelation of the HDAC enzyme.

Embodiment 99 Experiments on Determination of Compounds on Activity of Cancer Cells 1. Experimental principles: the inhibition of cancer cell growth with compounds is detected by an MTT method. The principle of the MTT method is as follows: yellow thiazolyl blue may penetrate through cell membranes and enter into cells, succinate dehydrogenase in living cell mitochondria may reduce exogenous MTT into water-insoluble ianthinus acicular Formazan crystals which deposit in the cells, the crystals can be dissolved with dimethyl sulfoxide (DMSO), the optical density of the crystals is detected with an enzyme-linked immunometric meter at the wavelength of 490 nm/570 nm, and the number of cells can be indirectly reflected.

2. Experimental materials: the used cancer cell lines are Hela (human cervical cancer cells), MCF-7 (human breast cancer cells), BGC-823 (human gastric cancer cells), A549 (human lung cancer cells), HT1080 (human fibrosarcoma cells), A431 (human epidermal squamous cell carcinoma cells), HUVEC (human umbilical vein endothelial cells), DU145 (human prostate cancer cells), K562 (human leukemia cells), U937 (human leukemia cells), Pac-1 (human pancreatic cancer cells), and MOLT-4 (human acute lymphoblastic leukemia cells), which are cultured with a DMEM+10% FBS culture medium or a 1640+10% FBS culture medium, respectively.

3. Experimental methods and analysis of results

Experimental groups: 190 μl cell suspension+10 μl pharmaceuticals in different concentrations (the final concentration is 10$^{-5}$-10$^{-10}$M)

Blank control group: 200 μl PBS

Negative control group: 190 μl cell suspension+10 μl 2% DMSO (the final concentration of DMSO is 0.1%)

Positive control group: 190 μl cell suspension+10 μl compounds in different concentrations a) Cells are inoculated on a 96-pore plate, with 1500 cells and 190 μl for each hole, and cultured overnight in a 5% $CO_2$ incubator at 37.

b) 10 μl of different pharmaceuticals is added into each hole the next day, with the final concentration of the pharmaceuticals of $10^{-5}$-$10^{-10}$M and three parallel holes, and incubated for 72 h in a 5% $CO_2$ incubator at 37.

c) 20 μl of 5 mg/mL MTT is added into each hole, and incubated for 4 h in a 5% $CO_2$ incubator at 37.

d) Supernatant is removed. 100 μl of DMSO is added into each hole and vibrated.

e) The reading is 570 nm. The cell survival rate is calculated. $GI_{50}$ is calculated according to the results, as shown in the following table.

available Zolinza (SAHA) is used as a positive control. The solvents are isopropanol and anhydrous ethanol (mixed in the volume ratio of 1:1). The test sample is dissolved with solvents and physiological saline in the ratio of 1:1 for use, and the above solvents and physiological saline are dissolved in the ratio of 1:1 as a negative control.

The subjects are female BALB/cA nude mice with the weight of 16±2 g and at the age of 4-5 weeks, purchased from Shanghai Institute of Materia Medica, Chinese Academy of Sciences (production certificate NO. SCXK (Shanghai) 2008-0017). The number of mice in each group: 12 mice in the negative control group, and 6 mice in the administration group.

The cell strains of human colon cancer HCT-116 are purchased from the cell bank of Chinese Academy of Sciences. The cell strains are inoculated to the right axilla subcutaneous layer of the nude mice, with $5\times10^6$ per mouse. After formed, the transplanted tumors are passed down two generations in the nude mice and then used.

| | $GI_{50}$ (μM) | | | | | | | | | |
|---|---|---|---|---|---|---|---|---|---|---|
| Sample | Hela | MCF7 | A549 | BGC823 | HT1080 | lncap | Du145 | U937 | PANC-1 | Molt-4 |
| SAHA | 37.8 | 1.8 | 7.70 | 4.50 | 3.80 | 4.56 | NA | 2.31 | 7.46 | NA |
| 1-1 | 0.4 | 0.09 | 0.09 | 0.1 | 0.05 | 0.05 | 0.008 | 0.007 | 0.3 | 0.009 |
| 1-2 | 0.1 | 0.05 | 0.3 | 0.02 | 0.1 | 0.07 | 0.004 | 0.004 | 0.2 | 0.03 |
| 1-3 | 1.0 | 1.2 | 10.0 | 0.06 | 4.0 | 2.0 | 0.3 | 0.5 | 6.0 | 1.0 |
| 1-4 | 1.3 | 0.2 | 2.9 | 2.5 | 0.8 | 0.2 | 0.36 | 0.03 | 1.6 | 0.1 |
| 1-5 | 2.0 | 0.8 | 0.6 | 0.1 | 1.0 | 0.6 | 0.1 | 0.1 | 3.0 | 1.0 |
| 1-6 | 1.0 | 0.6 | 0.5 | 0.4 | 1.3 | 1.2 | 0.05 | 0.2 | 3.0 | 1.0 |
| 1-7 | 5.0 | 0.7 | 0.4 | 0.3 | 0.3 | 0.5 | 0.02 | 0.02 | 1.5 | 0.1 |
| 1-8 | 0.1 | 0.1 | 0.1 | 0.3 | 0.07 | 0.2 | 0.03 | 0.02 | 0.1 | 0.02 |
| 1-9 | 0.05 | 0.05 | 0.03 | 0.05 | 0.04 | 0.03 | 0.003 | 0.005 | 0.6 | 0.01 |
| 1-10 | 0.1 | 0.001 | 0.1 | 0.2 | 0.1 | 0.08 | 0.01 | 0.02 | 1.3 | 0.02 |
| 1-11 | 0.1 | 0.09 | 5.09 | 0.16 | 0.08 | 0.03 | 0.006 | 0.009 | 0.8 | 0.01 |
| 1-12 | 0.9 | 0.8 | 1.2 | 0.06 | 1.0 | 0.3 | 0.1 | 0.1 | 6.0 | 0.1 |
| 2-1 | 0.2 | 0.5 | 0.9 | 5 | 4.1 | 2.01 | 0.05 | 1.3 | 2.06 | 0.1 |
| 2-2 | 0.6 | 2.3 | 2.0 | 1.6 | 4.5 | 23.6 | 56.5 | 10.2 | 0.6 | 26.2 |
| 2-3 | 26.5 | 21.4 | 2.6 | 1.56 | 40.5 | 0.5 | 0.56 | 1.23 | 2.65 | 23.1 |
| 2-4 | 23 | 52.6 | 4.5 | 2.6 | 1.6 | 85.2 | 6.4 | 18.6 | 4.2 | 0.9 |
| 2-5 | 12 | 26 | 2.13 | 20.6 | 1.02 | 0.56 | 5.46 | 21.03 | 26.4 | 1.03 |
| 2-6 | 0.5 | 0.65 | 4.2 | 56.2 | 12.0 | 11.65 | 0.56 | 12.6 | 45.01 | 64.5 |
| 2-7 | 0.1 | 0.09 | 0.09 | 0.1 | 0.08 | 0.65 | 0.006 | 0.009 | 0.8 | 2.1 |
| 3-1 | 0.01 | 2.1 | 0.35 | 1.2 | 1.06 | 5.4 | 2.03 | 21.5 | 10.6 | 0.15 |
| 3-2 | 0.6 | 0.1 | 0.36 | 1.02 | 1.35 | 1.42 | 1.06 | 5.26 | 1.23 | 1.06 |
| 3-3 | 0.45 | 1.20 | 1.09 | 5.94 | 0.06 | 0.45 | 0.05 | 0.14 | 4.13 | 2.12 |
| 4-1 | 0.26 | 0.13 | 0.54 | 0.23 | 0.85 | 1.03 | 1.65 | 1.56 | 1.34 | 4.02 |
| 4-2 | 1.23 | 0.15 | 25.1 | 2.12 | 0.03 | 1.23 | 4.02 | 5.01 | 1.03 | 2.00 |
| 4-3 | 1.06 | 2.55 | 4.66 | 7.12 | 3.03 | 1.02 | 0.14 | 0.65 | 0.01 | 0.03 |
| 4-4 | 1.003 | 0.006 | 0.01 | 1.02 | 0.65 | 4.26 | 2.1 | 10.2 | 3.012 | 0.05 |
| 5-1 | 3.05 | 3.65 | 21.3 | 2.10 | 19.6 | 73.5 | 0.65 | 0.34 | 0.65 | 0.01 |
| 5-2 | 0.35 | 0.69 | 0.24 | 1.3 | 1.05 | 5.03 | 6.41 | 0.02 | 21.36 | 10.26 |
| 6-1 | 0.6 | 0.059 | 0.1 | 0.36 | 0.05 | 0.042 | 0.034 | 0.005 | 0.23 | 0.65 |
| 6-2 | 73.5 | 59.6 | 15.6 | 4.6 | 41.02 | 0.9 | 1.6 | 2.65 | 0.68 | 0.4 |
| 6-3 | 45 | 56.6 | 41.0 | 5.0 | 25 | 12 | 13.6 | 10.1 | 0.89 | 3.64 |
| 6-4 | 0.5 | 0.69 | 4.6 | 2.55 | 1.33 | 0.63 | 0.42 | 6.35 | 1.25 | 2.65 |
| 6-5 | 0.54 | 4.12 | 0.365 | 26.5 | 1.65 | 0.45 | 0.695 | 2.658 | 1.645 | 0.268 |
| 6-6 | 0.86 | 0.952 | 0.001 | 0.065 | 4.16 | 0.65 | 0.3 | 1.29 | 1.653 | 56.4 |

$IC_{50}$ in the above table refers to the concentration of pharmaceuticals required for inhibiting 50% growth of cells (50% growth inhibition).

It can be seen from the results in the above table that, in comparison with the positive control (SAHA), the above pharmaceuticals have the activity for remarkably inhibiting the growth of the tumor cells listed.

Embodiment 100 Inhibition of the Compound I-3 on the Growth of Subcutaneously Transplanted Tumors Obtained by Inoculating Human Colon Cancer HCT-116 to Nude Mice 1. Experimental Materials The compound 1-3 is powder and includes three dosage groups: 20 mg/kg, 10 mg/kg and 5 mg/kg. The commercially 2. Experimental Methods and Analysis of Results Tumor tissues in the vigorous growth period are cut into about 1.5 $mm^3$, and inoculated to the right axilla subcutaneous layer of the nude mice under aseptic conditions. For the subcutaneously transplanted tumors of the nude mice, the diameter of the transplanted tumors is measured by a vernier caliper. The mice are randomly grouped after the tumors grow to 100-200 $mm^3$. 20 mg/kg, 10 mg/kg and 5 mg/kg of the compound 1-3 is administrated to the mice by caudal veins three times each week, for three successive weeks. 50 mg/kg of positive control pharmaceutical SAHA is administrated to the mice once every day, for three successive weeks. The diameter of the transplanted tumors is measured twice per week in the whole experimental process, and meanwhile the weight of the mice is weighed. The calculation formula of tumor volume (TV) is $TV = \frac{1}{2} \times a \times b^2$, where a and b represent length and width, respectively.

The relative tumor volume (RTV) is calculated according to the measured results, with the following calculation formula: $RTV = V_t/V_0$, where $V_0$ is the tumor volume obtained by measurement during administration in different cages (i.e., $d_0$), $V_t$ is the tumor volume obtained by measurement at each time. The evaluation indexes of the antitumor activity are: 1) the relative tumor proliferation ratio T/C (%), the calculation formula of the relative tumor proliferation ratio is as follows: $T/C(\%) = (T_{RTV}/C_{RTV}) \times 100\%$, where $T_{RTV}$ is the treatment group RTV, and $C_{RTV}$ is the negative control group RTV; 2) the tumor volume growth inhibition ratio GI %, the calculation formula of the tumor volume growth inhibition ratio is as follows: $GI\% = [1-(TVt-TV_0)/(CVt-CT_0)] \times 100\%$, where TVt is the tumor volume of the treatment group measured at each time, $TV_0$ is the tumor volume of the treatment group obtained during administration in different cages, CVt is the tumor volume of the control group measured at each time, and $CV_0$ is the tumor volume of the control group obtained during administration in different cages; and 3) the tumor weight inhibition ratio, the calculation formula of the tumor weight inhibition ratio is as follows: the tumor weight inhibition ratio. $(Wc-W_T)Wc \times 100\%$, where Wc is the tumor weight of the control group, and $W_T$ is the tumor weight of the treatment group.

All mice in the administration groups survive in the experimental process, and the results are as shown in tables 1.1-1.3.

TABLE 1.1

Experimental Therapy of the Compound 1-3 on the Transplanted tumors Obtained by Inoculating Human Colon Cancer HCT-116 to Nude Mice

| Groups | Dosages and methods of administration | | Number of mice | | Weight (g) | | TV (mm³) (mean ± SD) | | RTV (mean ± SD) | 1-T/C (%) |
|---|---|---|---|---|---|---|---|---|---|---|
| | | | $d_0$ | $d_{21}$ | $d_0$ | $d_{21}$ | $d_0$ | $d_{21}$ | | |
| Solvent control | 0.3 ml per mice q3d × 3w | iv | 12 | 12 | 16.1 | 13.4 | 120 ± 17 | 1246 ± 262 | 10.38 ± 2.95 | |
| SAHA | 50 mg/kg qd × 3w | iv | 6 | 6 | 16.6 | 13.3 | 116 ± 27 | 566 ± 221 | 4.87 ± 1.68* | 52.99 |
| 1-3 | 20 mg/kg q3d × 3w | iv | 6 | 6 | 16.7 | 13.1 | 116 ± 26 | 358 ± 201 | 3.09 ± 3.14* | 70.26 |
| | 10 mg/kg q3d × 3w | iv | 6 | 6 | 17.5 | 13.5 | 120 ± 19 | 751 ± 244 | 6.26 ± 3.33* | 39.71 |
| | 5 mg/kg q3d × 3w | iv | 6 | 6 | 16.7 | 13.3 | 122 ± 25 | 1166 ± 201 | 9.56 ± 2.44 | 7.92 | t student's test vs solvent control group,

*p is < 0.05

TABLE 1.2

Influence of the Compound 1-3 on the Tumor Volume of Transplanted tumors Obtained by Inoculating Human Colon Cancer HCT-116 to Nude Mice

| | Tumor Volume TV(mean ± SD) | | | | | | |
|---|---|---|---|---|---|---|---|
| Groups | 2011 Sep. 03 d 0 | 2011 Sep. 05 d 3 | 2011 Sep. 09 d 7 | 2011 Sep. 12 d 10 | 2011 Sep. 16 d 14 | 2011 Sep. 19 d 17 | 2011 Sep. 23 d 21 |
| Solvent Control | 120 ± 17 | 178 ± 29 | 328 ± 90 | 522 ± 150 | 735 ± 213 | 914 ± 203 | 1246 ± 262 |
| SAHA 50 mg/kg | 116 ± 27 | 146 ± 38 | 191 ± 25 | 283 ± 41 | 326 ± 45 | 417 ± 140 | 566 ± 221 |
| 1-3 20 mg/kg | 116 ± 26 | 129 ± 10 | 155 ± 28 | 193 ± 68 | 245 ± 117 | 275 ± 112 | 358 ± 201 |
| 1-3 10 mg/kg | 120 ± 19 | 163 ± 38 | 217 ± 67 | 302 ± 105 | 408 ± 70 | 571 ± 175 | 751 ± 244 |
| 1-3 5 mg/kg | 122 ± 25 | 179 ± 15 | 343 ± 58 | 454 ± 41 | 605 ± 60 | 895 ± 138 | 1166 ± 201 |

TABLE 1.3

Influence of the Compound 1-3 on the Weight of Mice with Tumors Obtained by Inoculating Human Colon Cancer HCT-116 to Mice

| | Weight (g) (mean ± SD) | | | | | | |
|---|---|---|---|---|---|---|---|
| Groups | 2011 Sep. 03 d 0 | 2011 Sep. 05 d 3 | 2011 Sep. 09 d 7 | 2011 Sep. 12 d 10 | 2011 Sep. 16 d 14 | 2011 Sep. 19 d 17 | 2011 Sep. 23 d 21 |
| Solvent Control | 16.1 ± 0.8 | 15.3 ± 1.1 | 14.8 ± 1.5 | 14.4 ± 1.3 | 13.9 ± 1.3 | 13.6 ± 1.2 | 13.4 ± 1.5 |
| SAHA 50 mg/kg | 16.6 ± 1.5 | 15.9 ± 1.5 | 14.9 ± 1.8 | 14.6 ± 1.4 | 14.1 ± 1.3 | 13.6 ± 1.3 | 13.3 ± 1.1 |
| 1-3 20 mg/kg | 16.7 ± 0.5 | 16.1 ± 0.4 | 14.6 ± 0.4 | 14.7 ± 0.4 | 13.7 ± 0.3 | 13.0 ± 0.3 | 13.1 ± 0.6 |
| 1-3 10 mg/kg | 17.5 ± 1.6 | 16.6 ± 1.9 | 15.8 ± 2.0 | 15.7 ± 2.0 | 14.8 ± 1.8 | 14.2 ± 1.7 | 13.5 ± 1.6 |
| 1-3 5 mg/kg | 16.7 ± 0.6 | 15.9 ± 0.7 | 15.0 ± 0.9 | 14.5 ± 1.2 | 14.1 ± 1.0 | 13.5 ± 0.9 | 13.3 ± 1.0 |

It can be seen from the results of the above tables that, after the mice are administered for three weeks, the tumor inhibition rate (1−T/C) of the positive control pharmaceutical SAHA on the subcutaneously transplanted tumors obtained by inoculating human colon cancer HCT-116 to the nude mice is 52.99%, the tumor inhibition rate (1−T/C) of 20 mg/kg of the compound 1-3 is 70.26%, the effect is obviously better than that of the positive control pharmaceutical SAHA.

Embodiment 101 Inhibition of the Compounds 1-4, 1-6, 1-7 and 1-8 on the Growth of Subcutaneously Transplanted Tumors Obtained by Inoculating Human Colon Cancer HCT-116 to Nude Mice The experimental methods and processes are the same as Embodiment 100. A dosage of 20 mg/kg is respectively set for the compounds 1-4, 1-6, 1-7 and 1-8. The tumor inhibition rate is calculated according to the method in Embodiment 100. The experimental results are as shown in tables 2.1-2.3.

TABLE 2.1

Experimental Therapy of the Compounds 1-4, 1-6, 1-7 and 1-8 on the Transplanted tumors Obtained by Inoculating Human Colon Cancer HCT-116 to Nude Mice

| Groups | Dosages and methods of administration | | number of mice $d_0$ | $d_{21}$ | Weight (g) $d_0$ | $d_{21}$ | TV (mm$^3$) (mean ± SD) $d_0$ | $d_{21}$ | RTV (mean ± SD) | 1-T/C (%) |
|---|---|---|---|---|---|---|---|---|---|---|
| Solvent Control | 0.3 mL per mouse q3d × 3w | iv | 12 | 12 | 16.5 | 13.2 | 119 ± 17 | 1238 ± 233 | 10.40 ± 1.95 | |
| SAHA | 50 mg/kg qd × 3w | iv | 6 | 6 | 16.9 | 13.4 | 118 ± 25 | 536 ± 203 | 4.54 ± 1.72* | 56.32 |
| 1-4 | 20 mg/kg q3d × 3w | iv | 6 | 6 | 16.6 | 13.0 | 116 ± 23 | 308 ± 198 | 2.65 ± 1.70* | 74.46 |
| 1-6 | 20 mg/kg q3d × 3w | iv | 6 | 6 | 16.9 | 13.1 | 121 ± 28 | 326 ± 221 | 2.69 ± 1.82* | 74.09 |
| 1-7 | 20 mg/kg q3d × 3w | iv | 6 | 6 | 16.6 | 13.2 | 115 ± 20 | 332 ± 186 | 2.89 ± 1.62* | 72.24 |
| 1-8 | 20 mg/kg q3d × 3w | iv | 6 | 6 | 16.1 | 12.9 | 116 ± 22 | 368 ± 241 | 3.17 ± 2.08* | 69.49 | t student's test vs solvent control group,
*p < 0.05

TABLE 2.2

Influence of the Compounds 1-4, 1-6, 1-7 and 1-8 on the Transplanted tumors Obtained by Inoculating Human Colon Cancer HCT-116 to Nude Mice

| | Tumor Volume TV (mean ± SD) | | | | | | |
|---|---|---|---|---|---|---|---|
| Groups | 2011 Dec. 12 d 0 | 2011 Dec. 15 d 3 | 2011 Dec. 19 d 7 | 2011 Dec. 22 d 10 | 2011 Dec. 26 d 14 | 2011 Dec. 29 d 17 | 2012 Jan. 2 d 21 |
| Solvent Control | 119 ± 17 | 175 ± 26 | 322 ± 88 | 512 ± 153 | 716 ± 222 | 928 ± 211 | 1238 ± 233 |
| SAHA 50 mg/kg | 120 ± 25 | 146 ± 36 | 189 ± 20 | 263 ± 33 | 300 ± 35 | 402 ± 146 | 536 ± 203 |
| 1-4 20 mg/kg | 118 ± 23 | 126 ± 12 | 157 ± 26 | 189 ± 52 | 234 ± 103 | 262 ± 132 | 308 ± 198 |
| 1-6 20 mg/kg | 120 ± 28 | 129 ± 15 | 156 ± 23 | 195 ± 58 | 249 ± 110 | 265 ± 122 | 326 ± 221 |
| 1-7 20 mg/kg | 116 ± 21 | 131 ± 11 | 158 ± 26 | 199 ± 68 | 245 ± 107 | 275 ± 132 | 332 ± 186 |
| 1-8 20 mg/kg | 118 ± 22 | 139 ± 15 | 165 ± 28 | 203 ± 69 | 265 ± 127 | 305 ± 142 | 368 ± 241 |

TABLE 2.3

Influence of the Compounds 1-4, 1-6, 1-7 and 1-8 on the Weight of Mice with tumors Obtained by Inoculating Human Colon Cancer HCT-116 to the Mice

| | Weight (g) (mean ± SD) | | | | | | |
|---|---|---|---|---|---|---|---|
| Groups | 2011 Dec. 12 d 0 | 2011 Dec. 15 d 3 | 2011 Dec. 19 d 7 | 2011 Dec. 22 d 10 | 2011 Dec. 26 d 14 | 2011 Dec. 29 d 17 | 2012 Jan. 2 d 21 |
| Solvent Control | 16.5 ± 0.8 | 15.2 ± 1.0 | 14.6 ± 1.3 | 14.2 ± 1.3 | 13.9 ± 1.3 | 13.5 ± 1.2 | 13.2 ± 1.3 |
| SAHA 50 mg/kg | 16.8 ± 1.0 | 15.7 ± 1.2 | 14.9 ± 1.6 | 14.6 ± 1.5 | 14.2 ± 1.4 | 13.8 ± 1.3 | 13.4 ± 1.1 |
| 1-4 20 mg/kg | 16.6 ± 1.2 | 16.2 ± 1.4 | 14.8 ± 1.2 | 14.5 ± 1.0 | 13.8 ± 0.9 | 13.3 ± 0.9 | 13.0 ± 1.0 |
| 1-6 20 mg/kg | 16.9 ± 1.0 | 16.6 ± 1.8 | 15.9 ± 1.6 | 15.5 ± 1.6 | 14.8 ± 1.8 | 14.2 ± 1.7 | 13.1 ± 1.6 |
| 1-7 20 mg/kg | 16.6 ± 1.1 | 15.9 ± 0.7 | 15.1 ± 0.9 | 14.5 ± 1.2 | 14.0 ± 1.0 | 13.5 ± 1.0 | 13.2 ± 1.0 |
| 1-8 20 mg/kg | 16.3 ± 1.0 | 15.8 ± 1.1 | 15.1 ± 0.9 | 14.5 ± 1.2 | 14.0 ± 1.0 | 13.5 ± 0.9 | 12.9 ± 0.9 |

It can be known from the results in the above tables that, after the mice are administrated for three weeks, the tumor inhibition rates (1−T/C) of 20 mg/kg of compounds 1-4, 1-6, 1-7 and 1-8 on the subcutaneously transplanted tumors obtained by inoculating human colon cancer HCT-116 to nude mice are 74.46%, 74.09%, 72.24% and 69.49%, respectively, and the effect is 52.99% better than that of the positive control pharmaceutical SAHA.

Embodiment 102 Comparison on the Tumor Inhibition Rates of the Compounds 1-3, 1-6 and 1-8 on Tumors The experimental methods are the same as Embodiment 100. The inoculated cells are respectively shown in the following table. Solvents, SAHA (50 mg/kg), the compound 1-3 (20 mg/kg), the compound 1-6 (20 mg/kg) and the compound 1-8 (20 mg/kg) are administrated to mice with different tumors, respectively. The tumor inhibition rates are calculated according to the methods in Embodiment 100. The results are shown in table 3.1.

TABLE 3.1

Comparison on the Compounds 1-3, 1-6 and 1-8 on Different Tumor Inhibition Rates

| Inoculated Cells | Source of Cells | Tested Drugs | Tumor Inhibition Rate (1 − T/C) × 100% |
|---|---|---|---|
| Human Lymphoma Cell Ramos | American Type Culture Collection(ATCC) | Solvent | — |
| | | SAHA(50 mg/kg) | 57.81 |
| | | 1-3 (20 mg/kg) | 70.08 |
| | | 1-6(20 mg/kg) | 60.94 |
| | | 1-8(20 mg/kg) | 58.33 |
| Human Blood Acute Monocytic Leukemia U937 | Cell Bank of Chinese Academy of Sciences | Solvent | — |
| | | SAHA (50 mg/kg) | 63.22 |
| | | 1-3 (20 mg/kg) | 65.21 |
| | | 1-6(20 mg/kg) | 66.37 |
| | | 1-8 (20 mg/kg) | 68.32 |
| Human Lung Caner Cell NCI-H1975 | Cell Bank of Chinese Academy of Sciences | Solvent | — |
| | | SAHA (50 mg/kg) | 58.03 |
| | | 1-3 (20 mg/kg) | 56.40 |
| | | 1-6 (20 mg/kg) | 59.19 |
| | | 1-8 (20 mg/kg) | 53.23 |
| Human Gastric Adenocarcinoma Cell BGC-823 | Cell Bank of Chinese Academy of Sciences | Solvent | — |
| | | SAHA (50 mg/kg) | 54.89 |
| | | 1-3(20 mg/kg) | 59.38 |
| | | 1-6(20 mg/kg) | 60.26 |
| | | 1-8(20 mg/kg) | 56.83 |
| Human Melanoma Cell A875 | Cell Bank of Chinese Academy of Sciences | Solvent | — |
| | | SAHA (50 mg/kg) | 62.01 |
| | | 1-3(20 mg/kg) | 63.89 |
| | | 1-6(20 mg/kg) | 66.64 |
| | | 1-8(20 mg/kg) | 68.07 |

It can be seen from the results in the above table that, the compounds 1-3, 1-6 and 1-8 have excellent inhibition effects on the growth of the subcutaneously transplanted tumors obtained by inoculating human lymphoma cells Ramos, human blood acute monocytic leukemia U937, human lung caner cells NCl-H1975, human gastric adenocarcinoma cells BGC-823, human melanoma cells A875 to nude mice. Except that the tumor inhibition rates of the compounds 1-3 and 1-8 are slightly lower than those of SAHA when administrated to the human lung caner cell NCl-H1975, the tumor inhibition rates of other groups are all higher than those of the SAHA group.

It should be noted that the above embodiments are just used for explaining, instead of limiting, the technical solutions of the invention.

The invention claimed is:

1. A cyclopeptide compound with a chemical structure shown as Formula I:

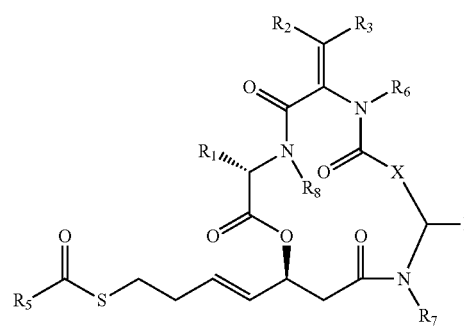

wherein,
$R_1$ is selected from the group consisting of hydrogen, $C_{1-12}$ alkyl, —$CH_2$—O—($C_{1-12}$ alkyl), —$CH_2$—NH—($C_{1-12}$ alkyl), —$CH_2$—S—($C_{1-12}$ alkyl), $C_{6-12}$ aryl, heteroaryl, —$CH_2$—($C_{6-12}$ aryl) and —$CH_2$-heteroaryl;
wherein the $C_{6-12}$ aryl, the heteroaryl, the —$CH_2$—$C_{6-12}$ aryl or the —$CH_2$-heteroaryl optionally contains one or more substituents selected from the group consisting of halogen, amino, hydroxyl, nitro, cyano, $C_{1-12}$ alkyl, $C_{1-12}$ alkoxy, amino $C_{1-12}$ alkyl, acyl, acyloxy, thio $C_{1-12}$ alkyl, carboxyl and phenyl;
$R_2$ is hydrogen;
$R_3$ is methyl;
*** is a double bond;
$R_4$ is hydrogen or $C_{1-12}$ alkyl;
$R_5$ is hydrogen, $C_{1-12}$ alkyl or $C_{3-12}$ cycloalkyl;
$R_6$, $R_7$, and $R_8$ are hydrogen;
X is selected from the group consisting of,

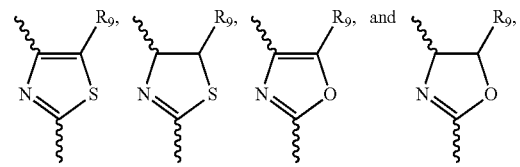

wherein $R_9$ is hydrogen.

2. The cyclopeptide compound according to claim 1, wherein the compound is selected from the following compounds:

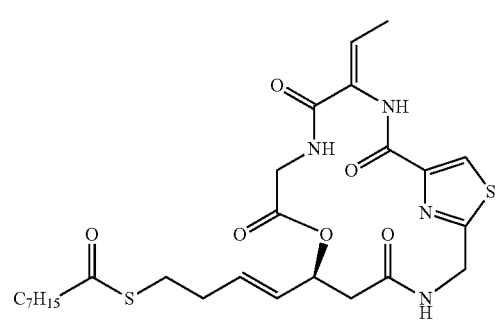

1-1

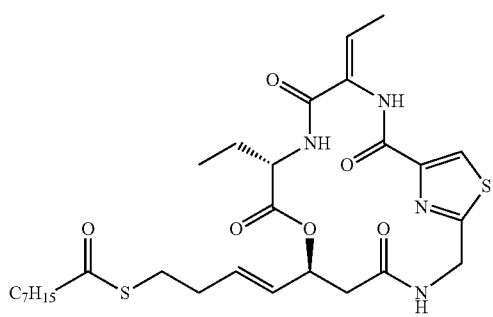
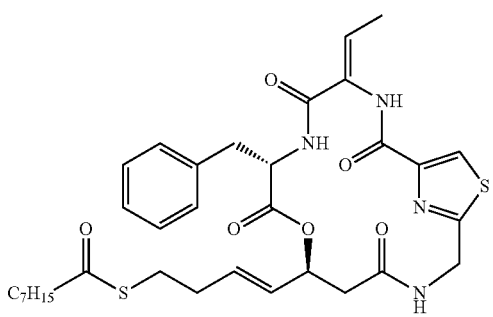
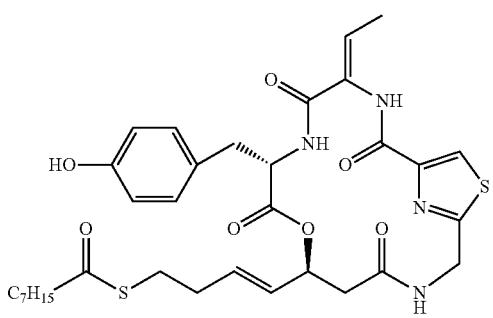
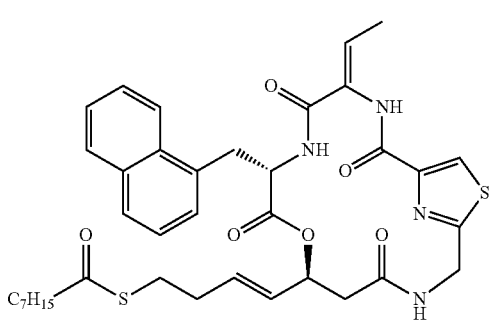
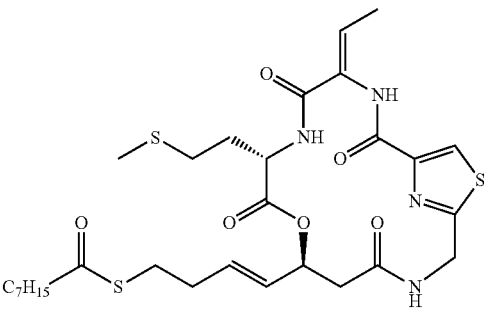
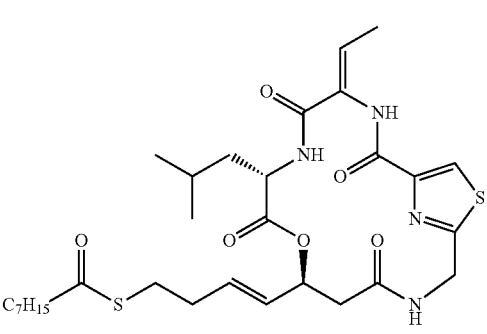

1-12
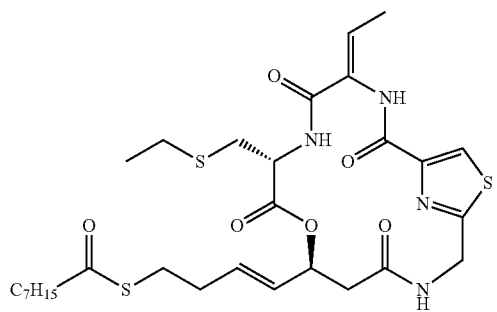
2-1
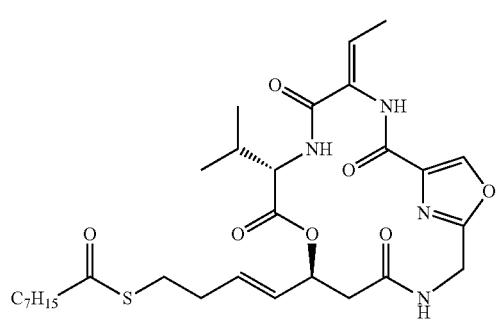
2-2
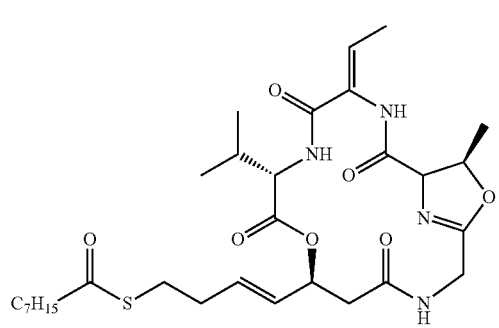
2-3
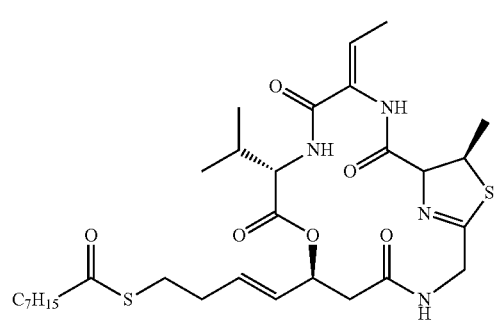
3-3
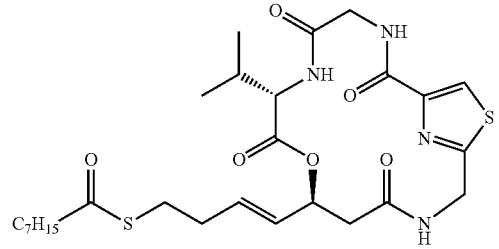
4-1
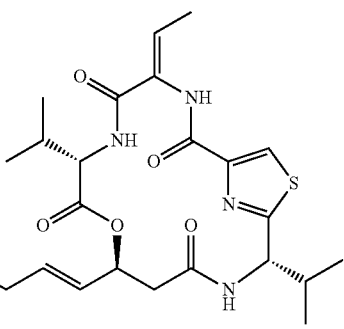
4-2
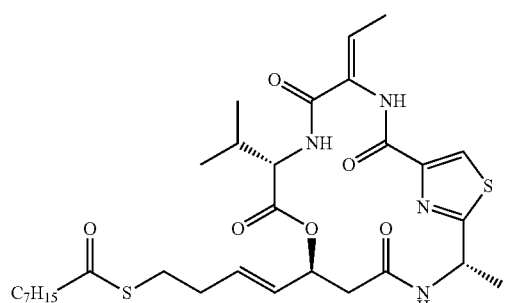
6-2
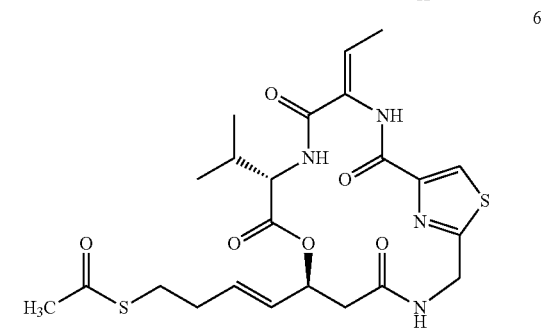
6-3
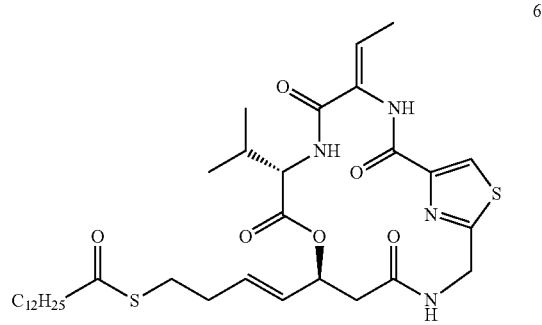
6-4
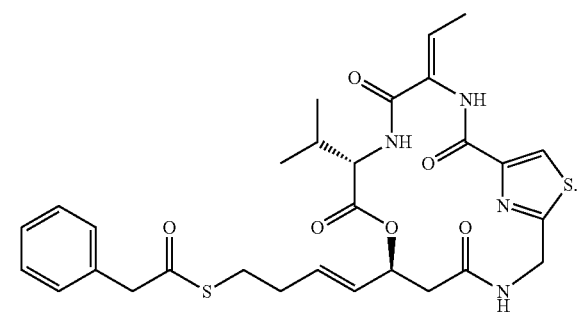
* * * * *